US012588912B2

(12) United States Patent
Walen et al.

(10) Patent No.: US 12,588,912 B2
(45) Date of Patent: Mar. 31, 2026

(54) SURGICAL SAW FOR ACTUATING A SAW BLADE WITH AN OSCILLATING HEAD, THE SAW HAVING A COUPLING ASSEMBLY FOR RELEASABLY HOLDING THE SAW BLADE

(71) Applicant: Stryker European Operations Holdings LLC, Kalamazoo, MI (US)

(72) Inventors: James G. Walen, Portage, MI (US); Robert Brindley, Delton, MI (US); Liam C. Cosgrove, County Clare (IE); Trevor Land, Richland, MI (US)

(73) Assignee: Stryker European Operations Holdings LLC, Portage, MI (US)

( * ) Notice: Subject to any disclaimer, the term of this patent is extended or adjusted under 35 U.S.C. 154(b) by 0 days.

(21) Appl. No.: 18/737,358

(22) Filed: Jun. 7, 2024

(65) Prior Publication Data

US 2024/0325029 A1      Oct. 3, 2024

Related U.S. Application Data

(60) Continuation of application No. 17/514,329, filed on Oct. 29, 2021, now Pat. No. 12,029,436, which is a
(Continued)

(51) Int. Cl.
*A61B 17/14* (2006.01)
*A61B 34/20* (2016.01)
*A61B 17/00* (2006.01)

(52) U.S. Cl.
CPC ............ *A61B 17/142* (2016.11); *A61B 34/20* (2016.02); *A61B 2017/00526* (2013.01);
(Continued)

(58) Field of Classification Search
CPC ....... A61B 17/14; A61B 17/142; A61B 17/00; A61B 17/141; A61B 17/148; A61B 34/20
See application file for complete search history.

(56) References Cited

U.S. PATENT DOCUMENTS

| | | |
|---|---|---|
| 306,285 A | 10/1884 | Rigby et al. |
| 683,924 A | 10/1901 | Fraser |

(Continued)

FOREIGN PATENT DOCUMENTS

| | | |
|---|---|---|
| AU | 2005292140 B2 | 7/2012 |
| CH | 654196 A5 | 2/1986 |

(Continued)

OTHER PUBLICATIONS

English Language abstract and computer-generated English language translation for FR 2651114 B1 extracred from espacenet.com databse on Dec. 3, 2020, 9 pages.

(Continued)

*Primary Examiner* — Christopher J Beccia
(74) *Attorney, Agent, or Firm* — Howard & Howard Attorneys PLLC

(57) ABSTRACT

A method of navigating a surgical saw with a navigation system having a navigation processor. The method comprising attaching a saw blade to a head of the surgical saw and determining a position of the surgical saw. The method also comprises touching a tracked pointer to one or more reference points on the saw blade and tracking the position and orientation of the tracked pointer as the tracked pointer is touched to the one or more reference points on the saw blade. The method further comprises determining an angular orientation of the saw blade based on the tracked pointer and the one or more reference points on the saw blade, and the navigation system determining the position and orientation of the saw blade relative to saw based on the position and
(Continued)

orientation of the saw, the angular orientation of the saw blade, and a characteristic of the saw blade.

18 Claims, 41 Drawing Sheets

Related U.S. Application Data continuation of application No. 16/381,552, filed on Apr. 11, 2019, now Pat. No. 11,179,163, which is a continuation of application No. 15/814,109, filed on Nov. 15, 2017, now Pat. No. 10,278,710, which is a continuation of application No. 15/267,845, filed on Sep. 16, 2016, now Pat. No. 9,820,753, which is a division of application No. 14/744,420, filed on Jun. 19, 2015, now Pat. No. 9,445,822, which is a division of application No. 14/134,152, filed on Dec. 19, 2013, now Pat. No. 9,060,783, which is a division of application No. 13/739,110, filed on Jan. 11, 2013, now Pat. No. 8,696,673, which is a division of application No. 12/622,944, filed on Nov. 20, 2009, now Pat. No. 8,444,647, which is a division of application No. 11/504,945, filed on Aug. 16, 2006, now Pat. No. 7,704,254.

(60) Provisional application No. 60/715,821, filed on Sep. 10, 2005.

(52) U.S. Cl.
CPC ............... *A61B 2017/00734* (2013.01); *A61B 2034/2051* (2016.02); *A61B 2034/2068* (2016.02); *Y10T 29/49826* (2015.01); *Y10T 29/49947* (2015.01)

(56) References Cited

U.S. PATENT DOCUMENTS

| | | | |
|---|---|---|---|
| 1,201,467 A | 10/1916 | Hogland | |
| 1,543,195 A | 6/1925 | Thugesen et al. | |
| 1,708,133 A | 4/1929 | Comparetto | |
| 2,138,862 A | 12/1938 | Johnston | |
| 2,702,550 A | 2/1955 | Rowe et al. | |
| 2,854,981 A | 10/1958 | Morrison | |
| 3,495,590 A | 2/1970 | Zeiller | |
| 3,642,002 A | 2/1972 | Otterstrom | |
| 3,678,934 A | 7/1972 | Warfield et al. | |
| 3,734,652 A | 5/1973 | Barnett | |
| 3,797,497 A | 3/1974 | Crim et al. | |
| 3,835,859 A | 9/1974 | Roberts et al. | |
| 3,882,737 A | 5/1975 | Crim et al. | |
| 3,905,105 A | 9/1975 | Tuke | |
| 3,978,862 A | 9/1976 | Morrison | |
| 4,019,408 A | 4/1977 | Idel | |
| 4,184,804 A | 1/1980 | Inagaki et al. | |
| 4,203,444 A | 5/1980 | Bonnell et al. | |
| 4,217,964 A | 8/1980 | Eaton | |
| 4,246,902 A | 1/1981 | Martinez | |
| 4,273,169 A | 6/1981 | Baenen | |
| 4,274,414 A | 6/1981 | Johnson et al. | |
| 4,461,296 A | 7/1984 | Hodge | |
| 4,502,184 A | 3/1985 | Karubian | |
| 4,513,742 A | 4/1985 | Arnegger | |
| 4,584,999 A | 4/1986 | Amegger | |
| 4,637,391 A | 1/1987 | Schlein | |
| 4,683,924 A | 8/1987 | Cornelius | |
| 4,700,702 A | 10/1987 | Nilsson | |
| 4,708,133 A | 11/1987 | Comparetto | |
| 4,892,093 A | 1/1990 | Zarnowski et al. | |
| 4,941,466 A | 7/1990 | Romano | |
| 5,014,430 A | 5/1991 | Wortham | |
| 5,092,869 A | 3/1992 | Waldron | |

| | | | |
|---|---|---|---|
| 5,100,506 A | 3/1992 | Sturtevant et al. | |
| 5,122,142 A | 6/1992 | Pascaloff | |
| 5,133,728 A | 7/1992 | Petersen | |
| 5,135,533 A | 8/1992 | Petersen et al. | |
| 5,178,626 A | 1/1993 | Pappas | |
| 5,265,343 A | 11/1993 | Pascaloff | |
| 5,306,285 A | 4/1994 | Miller et al. | |
| 5,349,754 A | 9/1994 | Wuensch et al. | |
| 5,403,318 A | 4/1995 | Boehringer et al. | |
| 5,423,822 A | 6/1995 | Hershberger et al. | |
| 5,439,472 A | 8/1995 | Evans et al. | |
| 5,468,247 A | 11/1995 | Matthai et al. | |
| 5,496,325 A | 3/1996 | McLees | |
| 5,591,170 A | 1/1997 | Spievack et al. | |
| 5,609,603 A | 3/1997 | Linden | |
| 5,697,158 A | 12/1997 | Klinzing et al. | |
| 5,725,530 A | 3/1998 | Popken | |
| 5,735,866 A | 4/1998 | Adams et al. | |
| 5,817,097 A | 10/1998 | Howard et al. | |
| 5,846,244 A | 12/1998 | Cripe | |
| 5,897,570 A | 4/1999 | Palleva et al. | |
| 6,001,115 A | 12/1999 | Ahola et al. | |
| 6,105,535 A | 8/2000 | Atamian et al. | |
| 6,106,535 A | 8/2000 | Dross et al. | |
| 6,113,618 A | 9/2000 | Nic | |
| 6,860,886 B1 | 3/2005 | Lee | |
| 6,875,222 B2 | 4/2005 | Long et al. | |
| 6,949,110 B2 | 9/2005 | Ark et al. | |
| 6,960,894 B2 | 11/2005 | Carusillo et al. | |
| 7,362,228 B2 | 4/2008 | Nycz et al. | |
| 7,497,860 B2 | 3/2009 | Carusillo et al. | |
| 7,638,958 B2 | 12/2009 | Philipp et al. | |
| 7,691,106 B2 | 4/2010 | Schenberger et al. | |
| 7,704,254 B2 | 4/2010 | Walen | |
| 7,744,616 B2 | 6/2010 | O'Donoghue | |
| 7,748,308 B2 | 7/2010 | Anderson et al. | |
| 8,043,292 B2 | 10/2011 | Carusillo | |
| 8,323,285 B2 | 12/2012 | Walen et al. | |
| 8,403,932 B2 | 3/2013 | Carusillo et al. | |
| 8,444,647 B2 | 5/2013 | Walen et al. | |
| 8,685,028 B2 | 4/2014 | Kim | |
| 8,696,673 B2 | 4/2014 | Walen et al. | |
| 8,702,710 B2 | 4/2014 | Carusillo | |
| 9,060,783 B2 | 6/2015 | Walen et al. | |
| 9,072,526 B2 | 7/2015 | Carusillo | |
| 9,192,390 B2 | 11/2015 | delRio et al. | |
| 9,439,655 B2 | 9/2016 | Cosgrove et al. | |
| 9,445,822 B2 | 9/2016 | Walen | |
| 9,554,808 B2 | 1/2017 | Carusillo | |
| 9,820,753 B2 | 11/2017 | Walen et al. | |
| 9,848,887 B2 | 12/2017 | Carusillo et al. | |
| 10,251,651 B2 | 4/2019 | Carusillo | |
| 10,278,710 B2 | 5/2019 | Walen et al. | |
| 10,687,823 B2 | 6/2020 | Mac an Tuile et al. | |
| 11,090,061 B2 | 8/2021 | Walen et al. | |
| 11,179,163 B2 | 11/2021 | Walen et al. | |
| 2002/0116022 A1 | 8/2002 | Lebouitz et al. | |
| 2002/0198556 A1 | 12/2002 | Ark | |
| 2003/0093103 A1 | 5/2003 | Malackowski et al. | |
| 2005/0020909 A1 | 1/2005 | Moctezuma de la Barrera et al. | |
| 2006/0009796 A1 | 1/2006 | Carusillo et al. | |
| 2006/0111723 A1 | 5/2006 | Chapolini et al. | |
| 2007/0068399 A1 | 3/2007 | Anderson et al. | |
| 2007/0083209 A1 | 4/2007 | Schenberger et al. | |
| 2007/0085496 A1 | 4/2007 | Philipp et al. | |
| 2007/0119055 A1 | 5/2007 | Walen et al. | |
| 2008/0119860 A1 | 5/2008 | McCarthy | |
| 2010/0292701 A1 | 11/2010 | Fisher et al. | |
| 2014/0163558 A1 | 6/2014 | Cosgrove et al. | |
| 2014/0194882 A1 | 7/2014 | Walen et al. | |
| 2019/0201003 A1 | 7/2019 | Carusillo | |
| 2019/0231364 A1 | 8/2019 | Walen et al. | |
| 2020/0315632 A1 | 10/2020 | Mac An Tuile et al. | |
| 2022/0047274 A1 | 2/2022 | Walen et al. | |

FOREIGN PATENT DOCUMENTS

| | | | |
|---|---|---|---|
| CN | 1045026 A | 9/1990 | |
| CN | 101791235 A | 8/2010 | |

(56)                    References Cited

FOREIGN PATENT DOCUMENTS

| CN | 102826549 | A  | 12/2012 |
|----|-----------|----|---------|
| CN | 103505259 | A  | 1/2014  |
| CN | 103860232 | A  | 6/2014  |
| DE | 354343    | C  | 6/1922  |
| DE | 478354    | C  | 6/1929  |
| DE | 2400696   | B2 | 8/1976  |
| DE | 2615301   | A1 | 10/1977 |
| DE | 2628131   | A1 | 12/1977 |
| DE | 2611720   | B2 | 5/1978  |
| DE | 2640267   | A1 | 5/1978  |
| DE | 2935732   | A1 | 3/1981  |
| DE | 3640516   | C1 | 4/1988  |
| DE | 3638404   | A1 | 5/1988  |
| DE | 8906511   | U1 | 7/1989  |
| DE | 4140395   | A1 | 6/1993  |
| DE | 102008062880 | A1 | 6/2010 |
| EP | 1880682   | A2 | 1/2008  |
| FR | 2651114   | B1 | 10/1991 |
| GB | 2317510   | A  | 3/1998  |
| RU | 2218112   | C2 | 12/2003 |
| WO | 03013371  | A1 | 2/2003  |
| WO | 2004105623 | A1 | 12/2004 |
| WO | 2006017066 | A2 | 2/2006  |
| WO | 2006063156 | A1 | 6/2006  |
| WO | 2007030793 | A2 | 3/2007  |
| WO | 2007045993 | A2 | 4/2007  |
| WO | 2008024717 | A2 | 2/2008  |

OTHER PUBLICATIONS

English Language abstract and machine-assisted English language translation for FR 2 651 114 B1 extracred from espacenet.com databse on Feb. 27, 2021, 9 pages.

English language abstract and machine-assisted English translation for CN 101791235 extracted from espacenet.com database on Jul. 20, 2020, 6 pages.

English language abstract and machine-assisted English translation for CN 102826549 extracted from espacenet.com database on Jul. 20, 2020, 5 pages.

English language abstract and machine-assisted English translation for CN 103505259 extracted from espacenet.com database dated Mar. 4, 2020, 7 pages.

English language abstract and machine-assisted English translation for CN 1045026 extracted from espacenet.com database on Jul. 20, 2020, 5 pages.

English language abstract and machine-assisted English translation for DE 2008 062 880 extracted from espacenet.com database on Dec. 11, 2017, 28 pages.

English language abstract and machine-assisted English translation for DE 2611720 B2 extracted from espacenet.com database on Feb. 17, 2021, 6 pages.

English language abstract and machine-assisted English translation for DE 2628131 A1 extracted from espacenet.com database on Feb. 17, 2021, 5 pages.

English language abstract and machine-assisted English translation for DE 2640267 A1 extracted from espacenet.com database on Feb. 17, 2021, 4 pages.

English language abstract and machine-assisted English translation for DE 2935732 A1 extracted from espacenet.com database on Feb. 17, 2021, 10 pages.

English language abstract and machine-assisted English translation for DE 3638404 A1 extracted from espacenet.com database on Feb. 17, 2021, 9 pages.

English language abstract and machine-assisted English translation for DE 3640516 C1 extracted from espacenet.com database on Feb. 17, 2021, 6 pages.

English language abstract and machine-assisted English translation for EP 1 880 682 A2 extracted from espacenet.com database on Aug. 29, 2018, 33 pages.

English language abstract and machine-assisted English translation for RU 2218112 C2 extracted from espacenet.com database on Feb. 17, 2021, 5 pages.

English language abstract and machine-assisted English translation for WO 2004/105623 A1 extracted from espacenet.com database on Feb. 17, 2021, 14 pages.

English language abstract for CN 103860232 extracted from espacenet.com database on Jul. 20, 2020, 1 page.

English language abstract for DE 4140395 A1 extracted from espacenet.com database on Feb. 17, 2021, 2 pages.

English language abstract for WO 03/013771 A1 extracted from espacenet.com database on Feb. 17, 2021, 1 page.

English language abstract not found for CH 654196 A5; however, see English language equivalent U.S. Pat. No. 4,513,742. Original document extracted from espacenet.com database on Feb. 17, 2021, 4 pages.

English language abstract not found for DE 2400696 B2; however, see English language equivalent U.S. Pat. No. 3,905,105. Original document extracted from espacenet.com database on Feb. 17, 2021, 20 pages.

EPO, "PCT International Search Report and Written Opinion for PCT/US2005/023769," dated Feb. 22, 2006.

International Search Report and ISA Written Opinion for PCT App. No. PCT/US2006/035204, Jul. 2007.

International Search Report and Written Opinion for PCT/US2005/023769, dated Feb. 22, 2006.

International Search Report for Application No. PCT/US2016/031407 dated Jan. 10, 2017, 6 pages.

International Search Report for PCT App. No. PCT/US2006/035204, Jul. 2007.

ISA Search Report and Written Opinion for PCT/US2016/031407, dated Oct. 1, 2017.

Machine-Assisted English translation for DE 2615301 A1 extracted from the espacenet.com database on Feb. 17, 2021, 6 pages.

Machine-Assisted English translation for DE 354343 C extracted from the espacenet.com database on Feb. 17, 2021, 3 pages.

Machine-Assisted English translation for DE 478354 C extracted from the espacenet.com database on Feb. 17, 2021, 4 pages.

Machine-Assisted English translation for DE 8906511 U1 extracted from the espacenet.com database on Feb. 17, 2021, 10 pages.

Stryker Corporation, Opposition Against EP Pat. No. 1 880 682 B1, dated Jan. 2011, 10 pages.

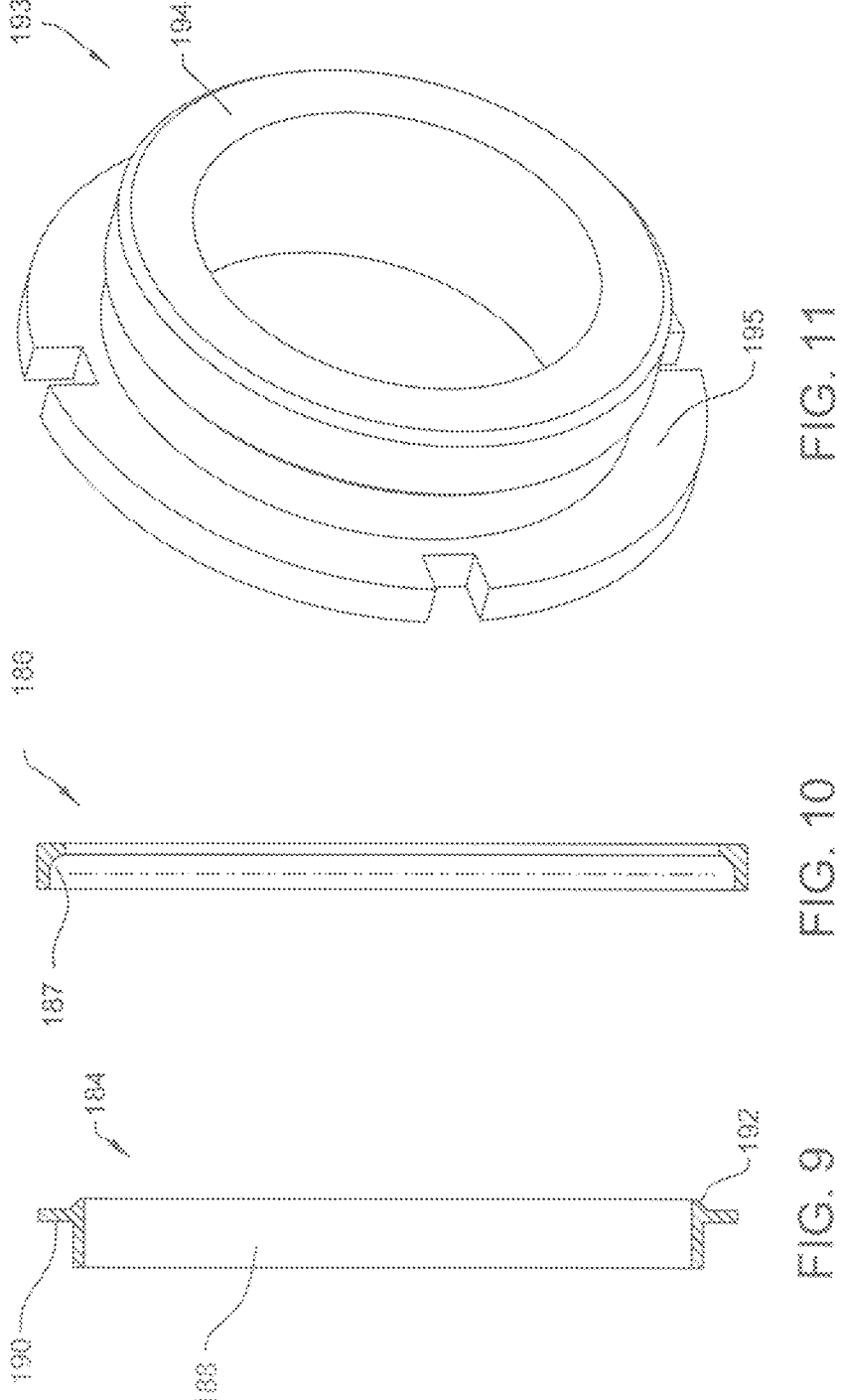

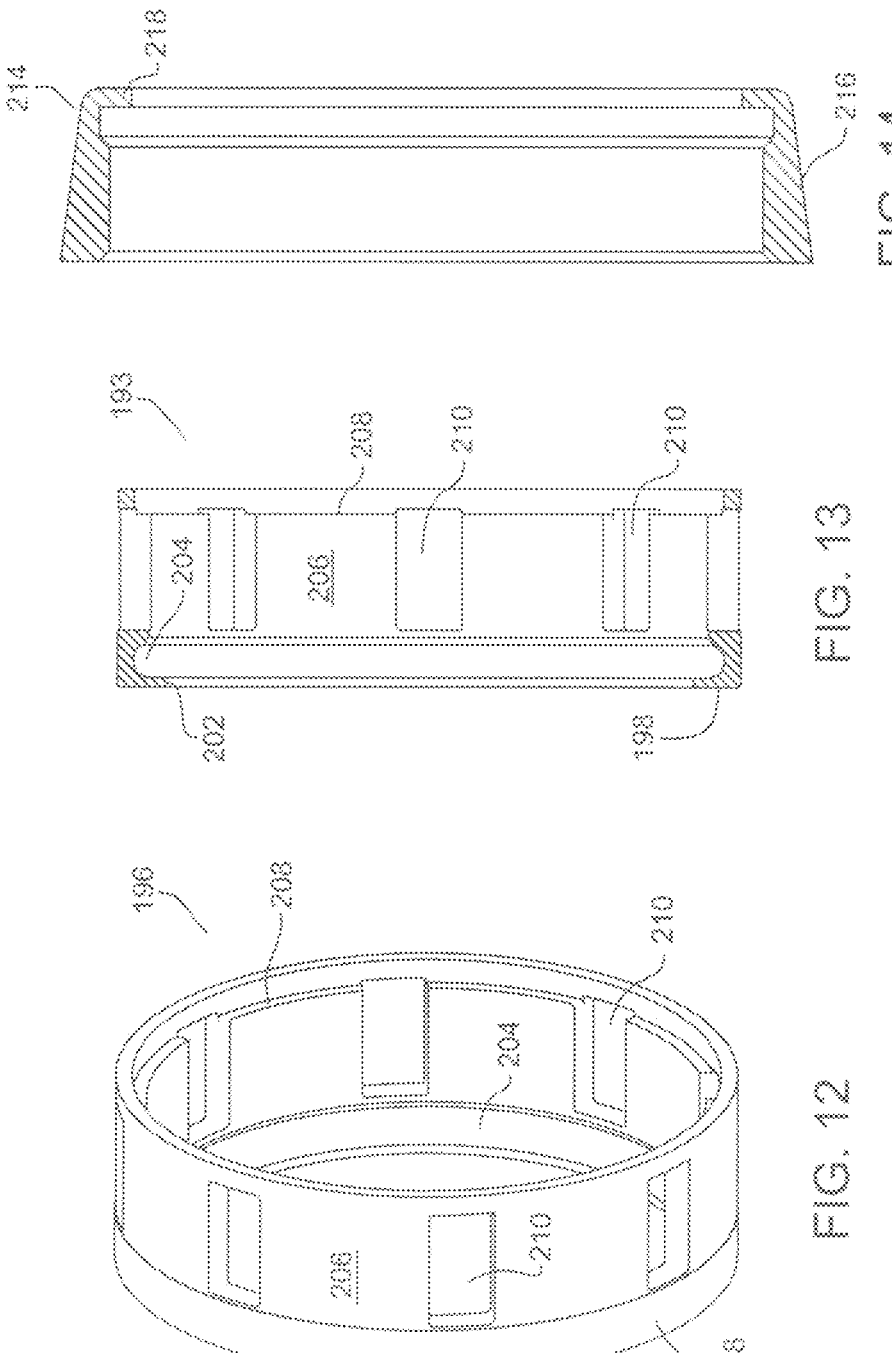

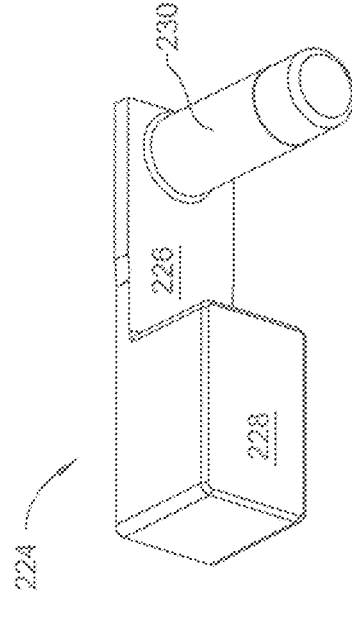
FIG. 15
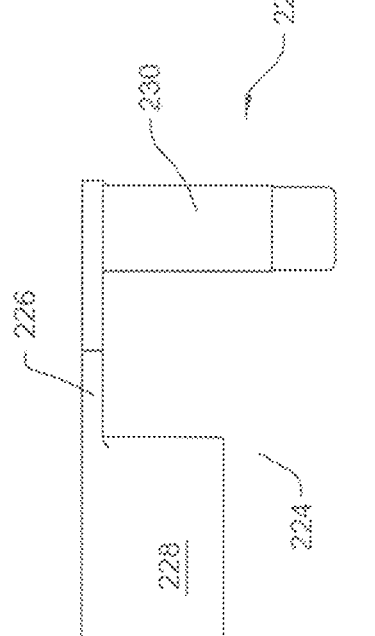
FIG. 16

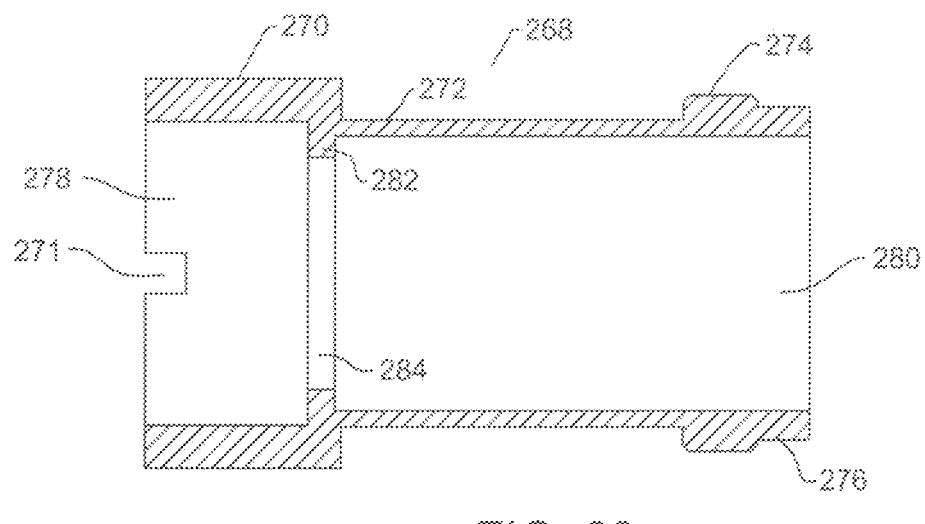
FIG. 20
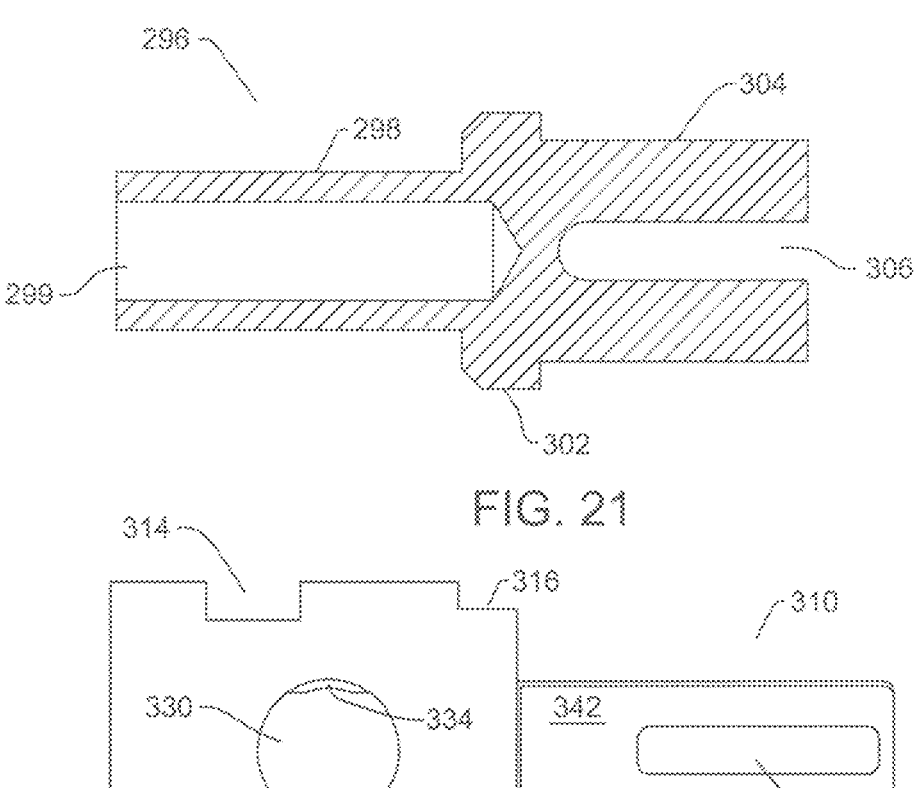
FIG. 21
FIG. 22

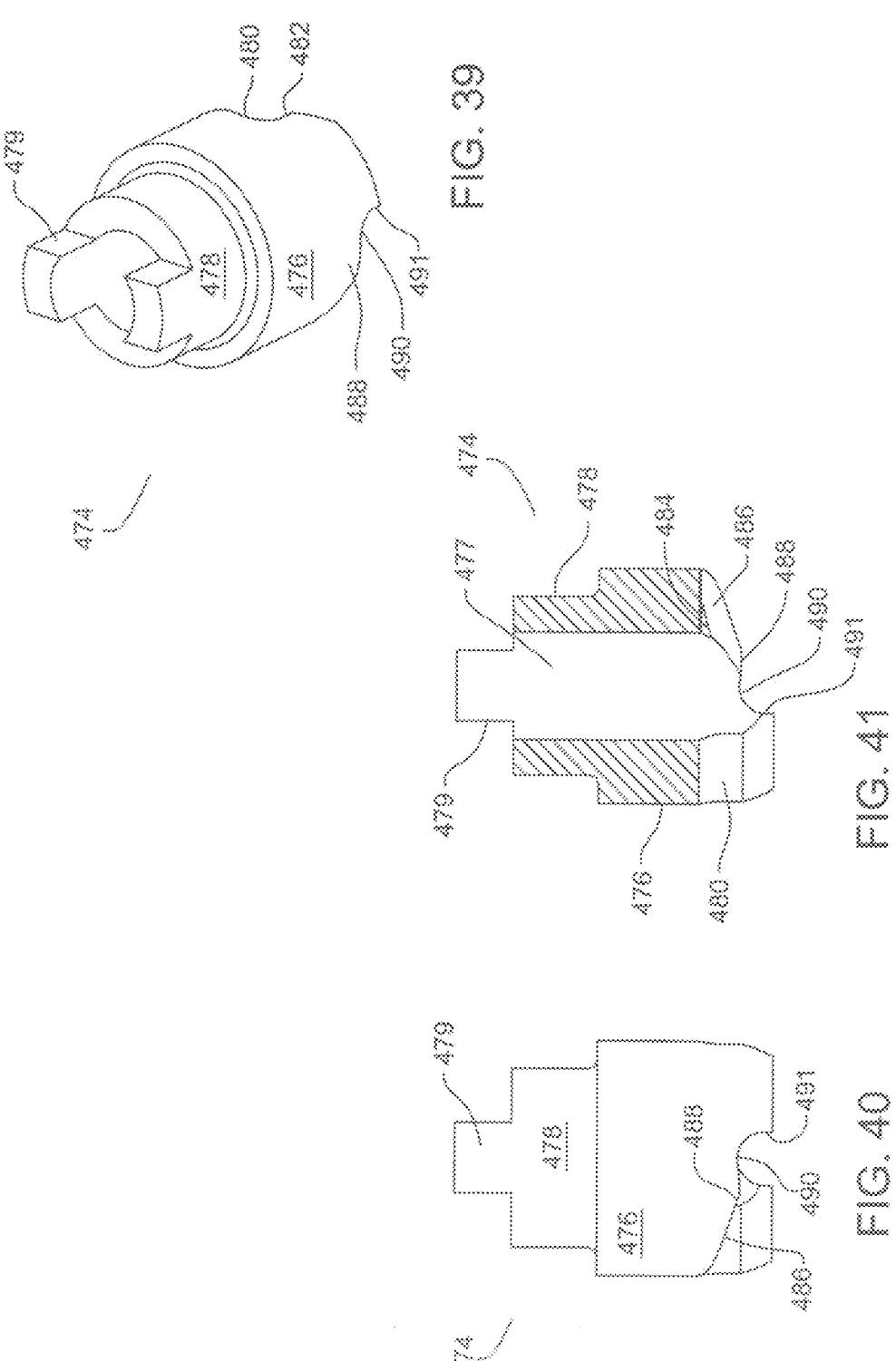

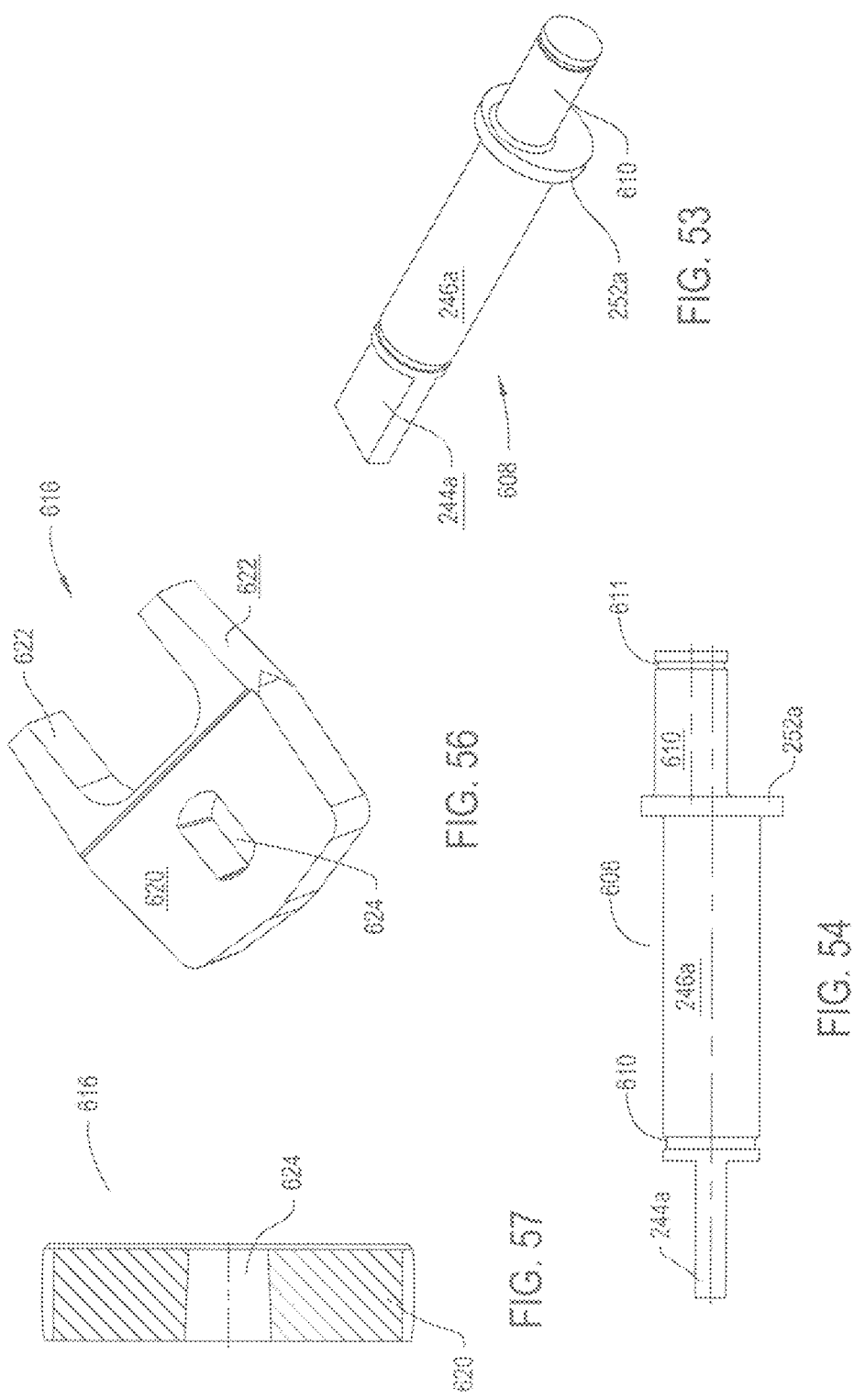

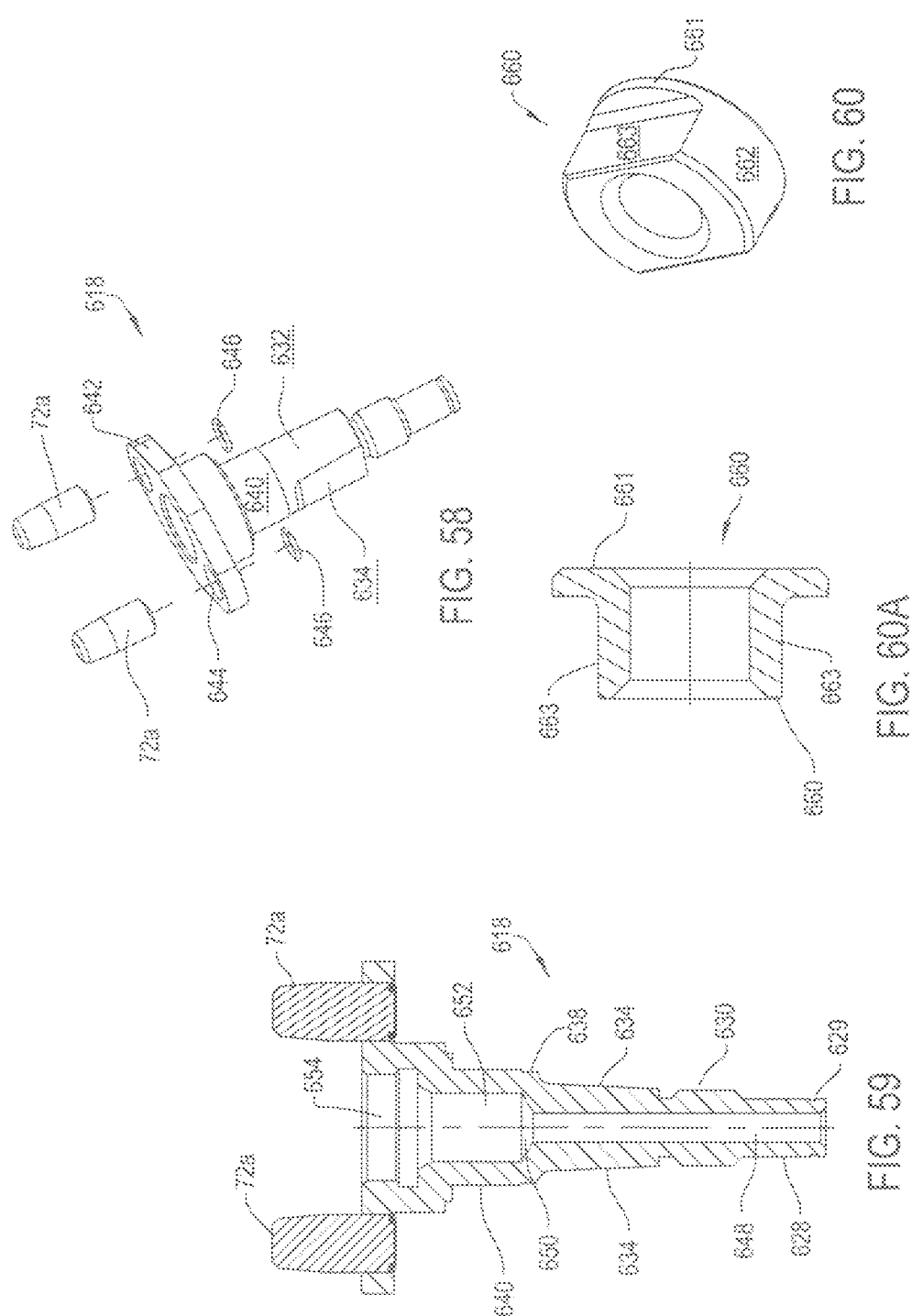

| BLADE LENGTH |
| BLADE GEOMETRY |
| TEETH GEOMETRY |
| DEFAULT OPERATING SPEED |
| MAXIMUM OPERATING SPEED |
| USE HISTORY |
| TIME STAMP |

DETERMINE
POSITION
OF SAW
832

MOUNT BLADE ASSY.
TO SAW
834

TOUCH POINTER TO
BLADE REFERENCE
POINT(S)
836

DETERMINE
ANGULAR ORIENTATION
OF BLADE ASSEMBLY
844

READ BLADE ASSY.
RFID DATA
846

FORWARD
BLADE GEOMETRY DATA
TO NAV. PROCESSOR
848

GENERATE BLADE
POSITION & ORIENTATION
DATA
850

SURGICAL SAW FOR ACTUATING A SAW BLADE WITH AN OSCILLATING HEAD, THE SAW HAVING A COUPLING ASSEMBLY FOR RELEASABLY HOLDING THE SAW BLADE

RELATED APPLICATIONS

This application is a continuation of U.S. patent application Ser. No. 17/514,329 filed 29 Oct. 2021. Application Ser. No. 17/514,329 is a continuation of U.S. patent application Ser. No. 16/381,552 filed 11 Apr. 2019, now U.S. Pat. No. 11,179,163. Application Ser. No. 16/381,552 is a continuation of U.S. patent application Ser. No. 15/814,109 filed 15 Nov. 2017, now U.S. Pat. No. 10,278,710. Application Ser. No. 15/814,109 is a continuation of U.S. patent application Ser. No. 15/267,845 filed 16 Sep. 2016, now U.S. Pat. No. 9,820,753. Application Ser. No. 15/267,845 is a divisional of U.S. patent application Ser. No. 14/744,420 filed 19 Jun. 2015, now U.S. Pat. No. 9,445,822. Application Ser. No. 14/744,420 is a divisional of U.S. patent application Ser. No. 14/134,152 filed 19 Dec. 2013 now U.S. Pat. No. 9,060,783. Application Ser. No. 14/134,152 is a divisional of U.S. patent application Ser. No. 13/739,110 filed 11 Jan. 2013, now U.S. Pat. No. 8,696,673. Application Ser. No. 13/739,110 is a divisional of application Ser. No. 12/622,944 filed 20 Nov. 2009 now U.S. Pat. No. 8,444,647. Application Ser. No. 12/622,944 is a divisional of application Ser. No. 11/504,945 filed 16 Aug. 2006, now U.S. Pat. No. 7,704,254. Application Ser. No. 11/504,945 claims priority under 35 U.S.C. Sec. 119 from U.S. Pat. App. No. 60/715,821 filed 10 Sep. 2005. The contents of the priority applications are incorporated herein by reference.

FIELD OF THE INVENTION

This invention is related generally to a surgical saw and, more particularly, a surgical sagittal saw and a complementary saw blade assembly.

BACKGROUND OF THE INVENTION

A sagittal saw is a powered surgical tool that is typically used in an orthopedic surgical procedure. A sagittal saw generally includes a handpiece that houses a motor and the complementary control circuit that regulates actuation of the motor. Extending forward, distally, from the handpiece is a head. Internal to the head is an oscillating shaft. Removably attached to the oscillating shaft is a saw blade. The exposed distal front edge of the blade is formed with teeth. The teeth cut the tissue against which the blade is applied. A drive mechanism internal to the housing generates power. This power is applied to actuate the oscillating shaft so that the shaft and the attached blade move in a back-and-forth pattern in which the blade is aligned. When the saw is so actuated, the blade teeth move in a back-and-forth pattern against the tissue against which they are applied. Due to the forward pressure applied by the surgeon holding the saw, the teeth cut and separate the hard tissue against which the blade is applied.

A sagittal saw is often used in an orthopedic surgical procedure to selectively remove bone. One particular type of orthopedic surgical procedure in which the saw is used is a joint replacement procedure. As implied by the name, in this type of procedure, the surgeon resects the bone between the joints in the patient and substitutes an artificial joint.

In an orthopedic surgical procedure it is important to ensure that, when the section to be resected is separated from the remaining bone, the section is removed along precise lines. Accuracy is mandatory because the substitute joint typically has a component designed to precisely fit in the space left by the cut line of the bone left in place.

The Applicant's Assignee's U.S. patent application Ser. No. 10/887,642, SURGICAL SAGITTAL SAW AND METHOD OF USING SAME, filed 9 Jul. 2004, U.S. Patent Publication No. 2006/0009796 A1, now U.S. Pat. No. 7,497, 860, incorporated herein by reference, discloses an exemplary saw and complementary saw blade. The blade assembly of this invention includes a bar to which a blade head is pivotally mounted. Drive rods disposed in the bar extend proximally rearward. The blade bar is removably attached to a head that is part of that is part of the saw of this invention. The drive rods are coupled to an oscillating shaft integral with saw head. When the saw of this invention is actuated, the oscillating shaft moves back and forth. This movement, in turn, causes the drive rods to reciprocate.

However, it may be desirable to have a sagittal saw with an assembly that allows the saw head to be rotated and/or indexed. It may also be desirable to track the position and/or orientation of the sagittal saw and/or blade assembly.

SUMMARY OF THE INVENTION

This disclosure generally relates to a surgical sagittal saw and a complementary blade assembly designed for use with the saw. The sagittal saw of this invention has a head with a tool-less coupling assembly for releasably holding the blade assembly in place. The coupling assembly also does not include components that are removed from the head. The saw head is also capable of being rotated, indexed, around the longitudinal axis of the head. This is because often it is desirable to position the head so that the complementary blade assembly is disposed in a plane that is not simply perpendicular to the axis that extends top-to-bottom through the saw. Therefore, this type of saw normally includes an indexing assembly that allows the saw head to be rotated, indexed, to a select angular orientation and locked in place. The head of the disclosed saw assembly is relatively easy to release from a locked indexed position, rotate to a new index position and then lock in the new index position.

The surgical sagittal saw and complementary blade assembly may also be configured to communicate with a navigation system including a navigation processor. The navigation processor may be configured to determine the position and orientation of the saw, the angular orientation of the blade assembly, and a characteristic of the blade assembly.

More specifically, cutting system for executing a surgical procedure, said cutting system comprising a saw assembly and a blade assembly. The saw assembly may comprise a housing, a saw head coupled to said housing, at least one coil, a first transceiver in communication with the at least one coil, and a saw processor for processing data received from the first transceiver. The blade assembly may be removably coupled to the saw assembly and comprise a blade bar, a blade head, and a tag. The blade bar may include a distal end and opposing proximal end. The blade head may be disposed at the distal end of the blade bar. The tag may comprise a memory containing data related to one or more characteristics of the blade assembly. The tag may be in communication with a blade coil, wherein the blade coil is configured to communicate data from the memory of the tag to the saw processor of the saw assembly via the at least one coil and said first transceiver.

The disclosure may also relate to a method of navigating a surgical saw with a navigation system having a navigation processor. The method may comprise a step of attaching a saw blade to a head of the surgical saw. The method may also comprise a step of touching a pointer including a first tracking device to one or more reference points on the saw blade. The method may further comprise a step of determining a position and orientation of the surgical saw. The method may comprise a step of tracking the position and orientation of the first tracking device as the pointer is touched to the one or more reference points on the saw blade. The method may also comprise a step of determining an angular orientation of the saw blade based on the position and orientation of the first tracking device when touching the one or more reference points on the saw blade. The method may further comprise a step of determining the position and orientation of a distal end of the saw blade relative to surgical saw using the navigation processor based on the position and orientation of the saw, the angular orientation of the saw blade, and a characteristic of the saw blade.

The disclosure may also relate to a method of navigating a surgical saw with a navigation system having a navigation processor. The method comprise a step of indexing the head of a surgical saw about a longitudinal axis of the surgical saw. The method may also comprise a step of attaching a saw blade assembly to the indexed head of the surgical saw. The method may further comprise a step of touching a pointer including a first tracking device to one or more reference points on the saw blade assembly. The method may also comprise a step of determining a position and orientation of the surgical saw. The method may comprise a step of tracking the position and orientation of the first tracking device as the pointer is touched to the one or more reference points on the saw blade assembly. The method may further comprise a step of determining an angular orientation of the saw blade assembly based on the position and orientation of the first tracking device when touching the one or more reference points on the saw blade assembly. The method may also comprise a step of determining the position and orientation of a distal end of the saw blade relative to surgical saw using the navigation processor based on the position and orientation of the saw, the angular orientation of the saw blade assembly, and a length of the saw blade assembly.

BRIEF DESCRIPTION OF THE DRAWINGS

The above and further features and benefits of this invention are understood from the Detailed Description below taken in conjunction with the attached drawings in which:

FIG. 9 is a cross sectional view of the inner race of the proximally located bearing assembly disposed around the saw head;

FIG. 10 is a cross sectional view of the outer race of the proximally located bearing assembly disposed around the saw head;

FIG. 11 is a perspective view of the retainer ring fitted to the proximal end of the saw head;

FIG. 12 is a perspective view of the outer race of the distal located bearing assembly disposed around the saw head;

FIG. 13 is a cross sectional view of the outer race of FIG. 12;

FIG. 14 is a cross sectional view of the threaded ring that holds the moor housing to the saw;

FIG. 15 is a perspective view of the indexing assembly lock link;

FIG. 16 is a side view of the indexing assembly lock link;

FIG. 20 is a cross sectional view of the rear inner housing;

FIG. 21 is a cross sectional view of the rotor drive coupler;

FIG. 22 is a top plan view of the front inner housing internal to the saw head;

FIG. 39 is a perspective view of the blade coupling assembly cam;

FIG. 40 is a side plan view of the cam;

FIG. 41 is a cross sectional view of the cam;

FIG. 53 is a perspective view of the bearing retainer;

FIG. 54 is a side view of the drive shaft;

FIG. 55 is a perspective view of the bearing retainer;

FIG. 56 is a perspective view of the oscillating yoke;

FIG. 57 is a cross sectional view through the oscillating yoke;

FIG. 58 is an exploded view of the oscillating head and the components attached thereto;

FIG. 59 is a cross sectional view of the oscillating head;

FIG. 60 is perspective view of the nut that hold the oscillating yoke and oscillating head together;

FIG. 60A is a cross sectional view of the nut of FIG. 60;

FIG. 66 is a perspective view of another alternative oscillating yoke;

It should be appreciated that the above drawings that illustrate mechanical elements of this invention should be understood to generally show the relative proportions of the individual features of the element components and of the elements to each other.

DETAILED DESCRIPTION

I. Overview

Figure 1:
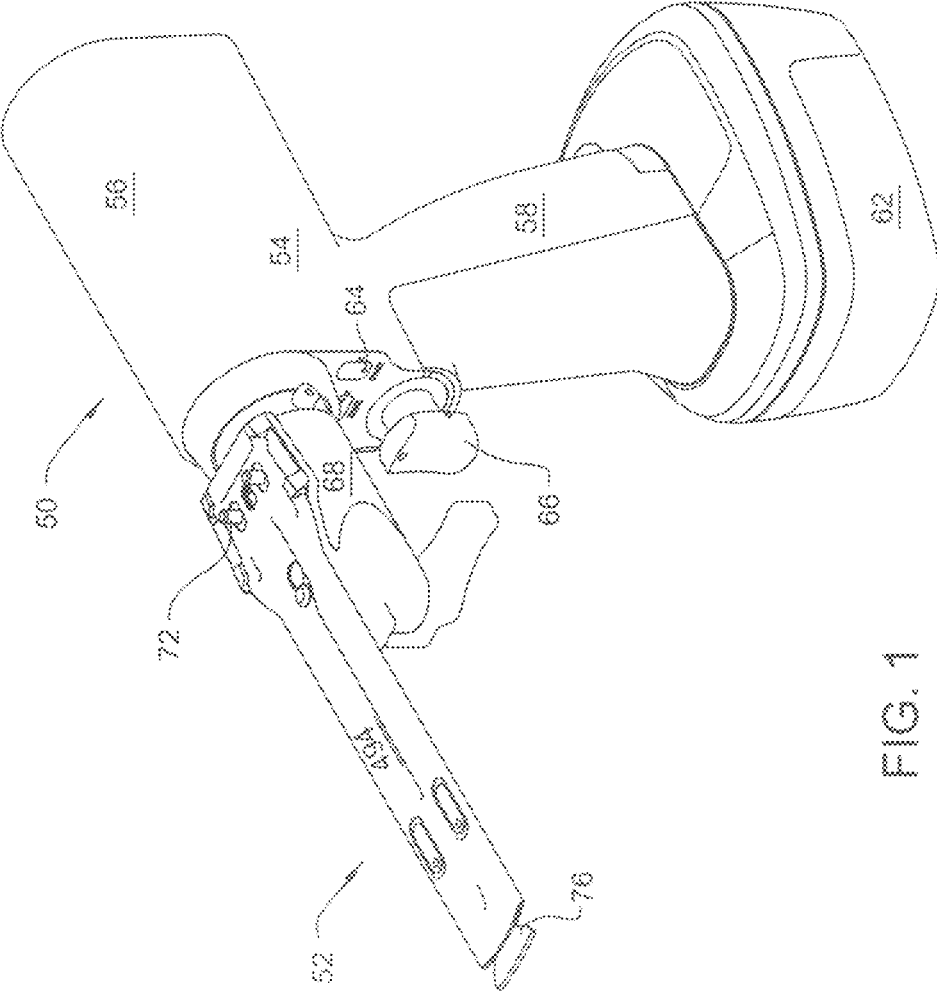
FIG. 1 is a perspective view of a surgical sagittal saw with saw blade attached that is constructed in accordance with this invention.
Figure 2:
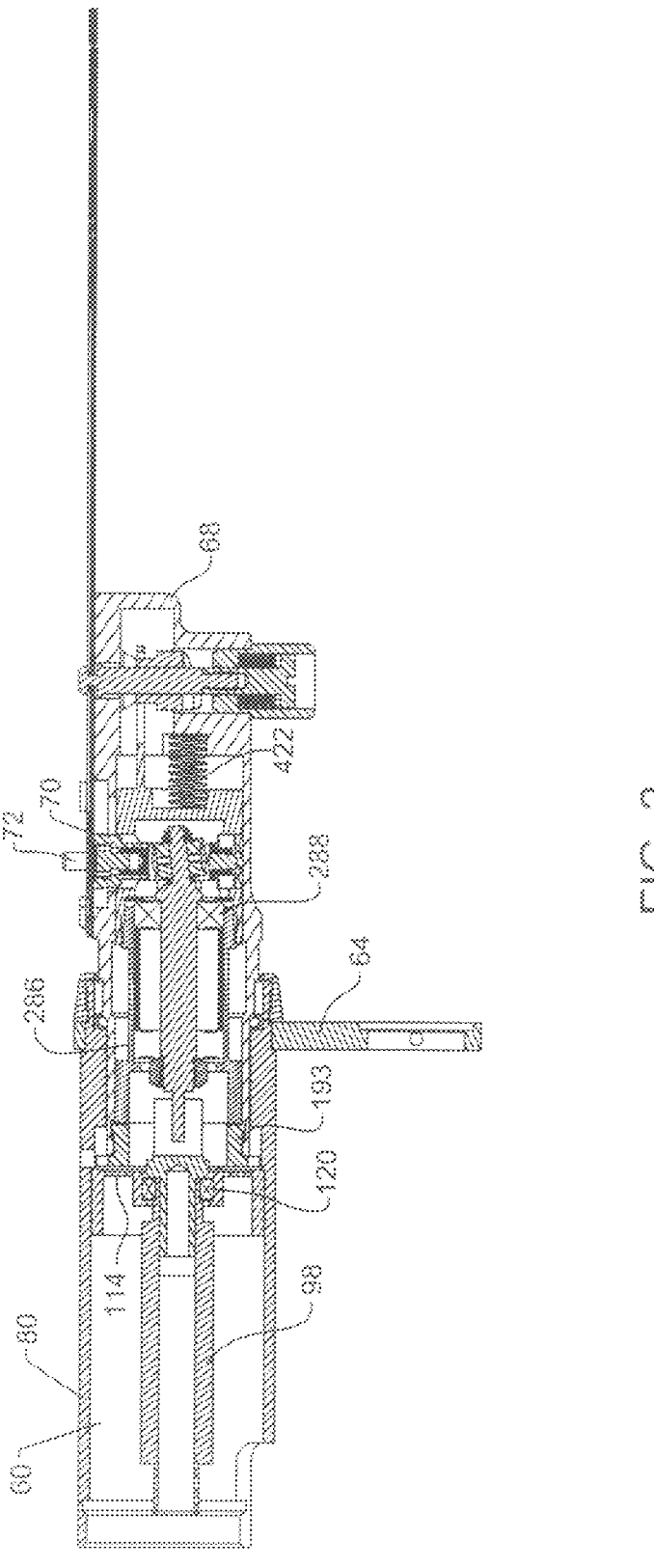
FIG. 2 is a cross sectional view of the motor and saw distal end with attached blade of this invention.

FIGS. 1 and 2 depict the surgical saw 50 of this invention and the blade assembly 52 used with the saw. Saw 50 includes a housing 54. The housing 54 has an elongated, top-located barrel section 56. A pistol-grip shaped handle 58, also part of housing 54, extends downwardly from barrel section 56. A motor 60 is disposed inside the housing barrel section 56. In some versions of the invention, motor 60 is a brushless, sensorless DC motor. This is exemplary, not limiting. In other versions of the invention, the motor 60 may be a DC motor with brushes and/or sensors, an AC driven motor or a motor that is pneumatically or hydraulically driven. In the illustrated version of the invention, saw 50 is a cordless power tool. A battery 62 removably attached to the butt end of handle 58 contains a charge for energizing the motor. Again, it should be understood that the invention is not so limited. In alternative versions of the invention, a power cord, an air line or a fluid line is connected to the housing 54 for providing the power needed to actuate the motor 60.

Figure 28:
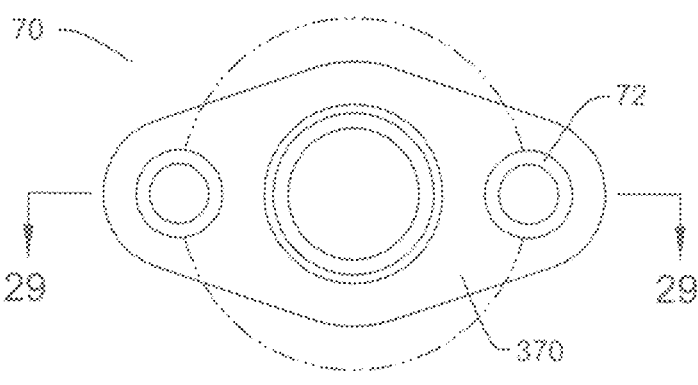
FIG. 28 is a top view of the oscillating head.

A front plate 64 is fitted over the distal end opening of the housing barrel section 56. ("Distal", it shall be understood, means toward the surgical site to which the handpiece 30 is directed. "Proximal" means away from the surgical site.) A trigger 66 is moveably mounted to the front plate 64 and extends forward of the front plate. A control circuit internal to the housing handle 58, not illustrated and not part of this invention, monitors actuation of the trigger 66. Based on the extent to which the trigger 66 is actuated, the control circuit selectively energizes motor 60 to cause a motor rotor 98 to rotate at the desired speed A head 68 extends forward from the front plate 64 above the trigger 66. The proximal end of blade assembly 52 is removably fitted to the head 68. Internal to the saw head 68 is an oscillating head 70 (FIGS. 2 and 28). Oscillating head 70 includes a pair of pins 72. When the blade assembly 52 is mounted to the saw head 68, drive rods 74 (FIG. 43), part of the blade assembly 52, engage the pins. When the saw motor 60 is actuated, the oscillating head 70 and pins 72 oscillate. The movement of the pins 72 causes the drive rods 74 to reciprocate. A blade head 76 forms the most distal end of the blade assembly 52. The drive rods 74 are attached to the blade head 76. The reciprocal movement of the drive rods 74 causes the blade head 76 to oscillate back and forth in a cutting motion.

II. Saw Motor, Saw Head and Indexing Assembly

Figure 3:
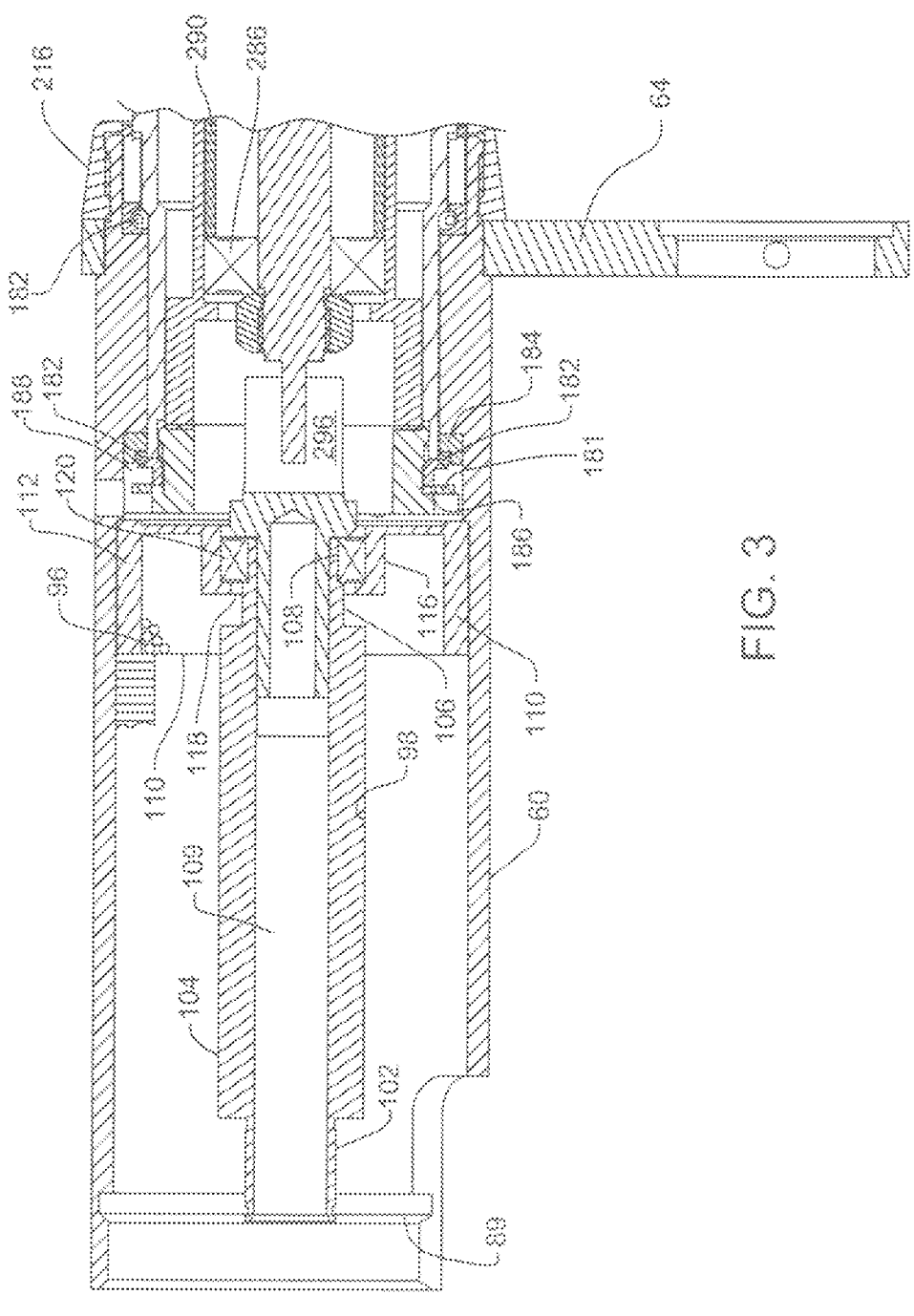
FIG. 3 is an enlarged cross sectional view of the proximal portion of the assembly illustrated in FIG. 2.
Figure 4:
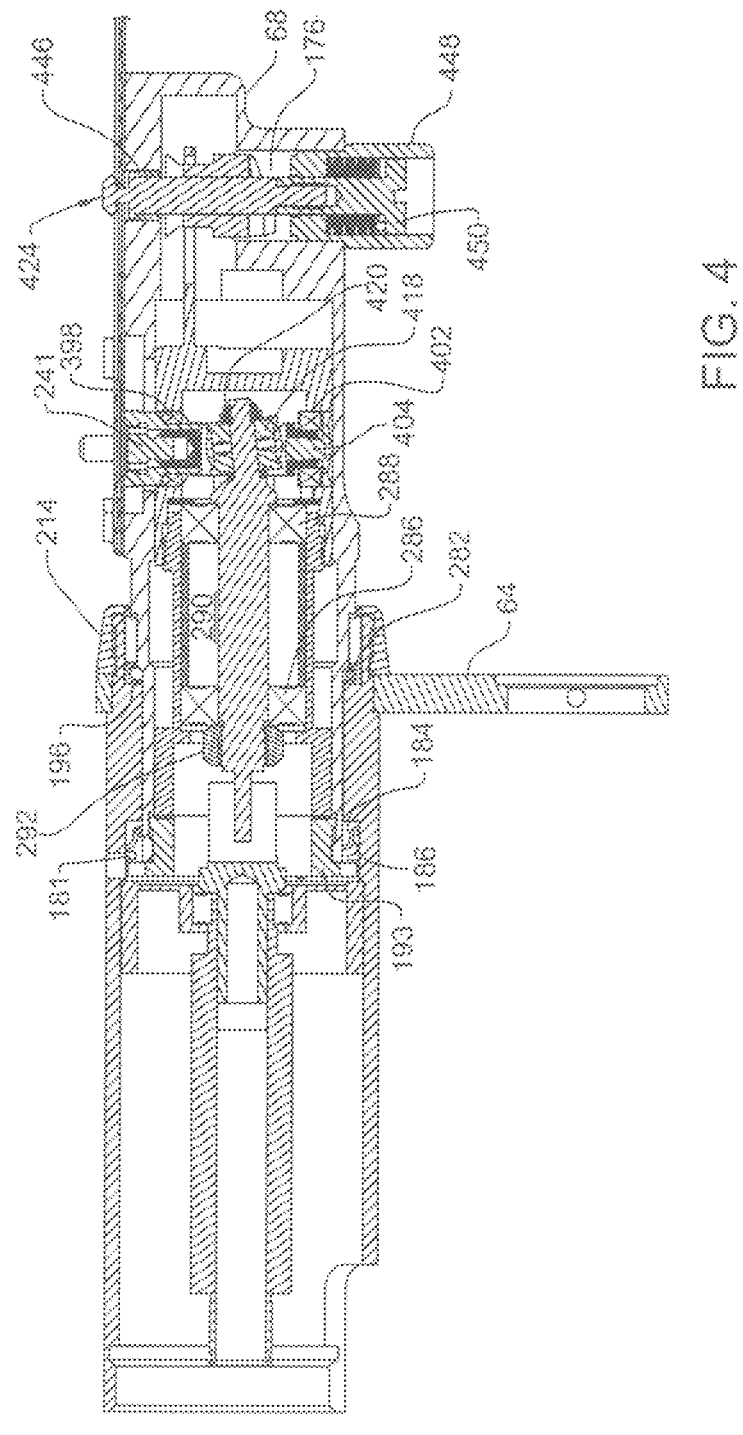
FIG. 4 is an enlarged cross sectional view of the distal portion of the assembly illustrated in FIG. 2.
Figure 5:
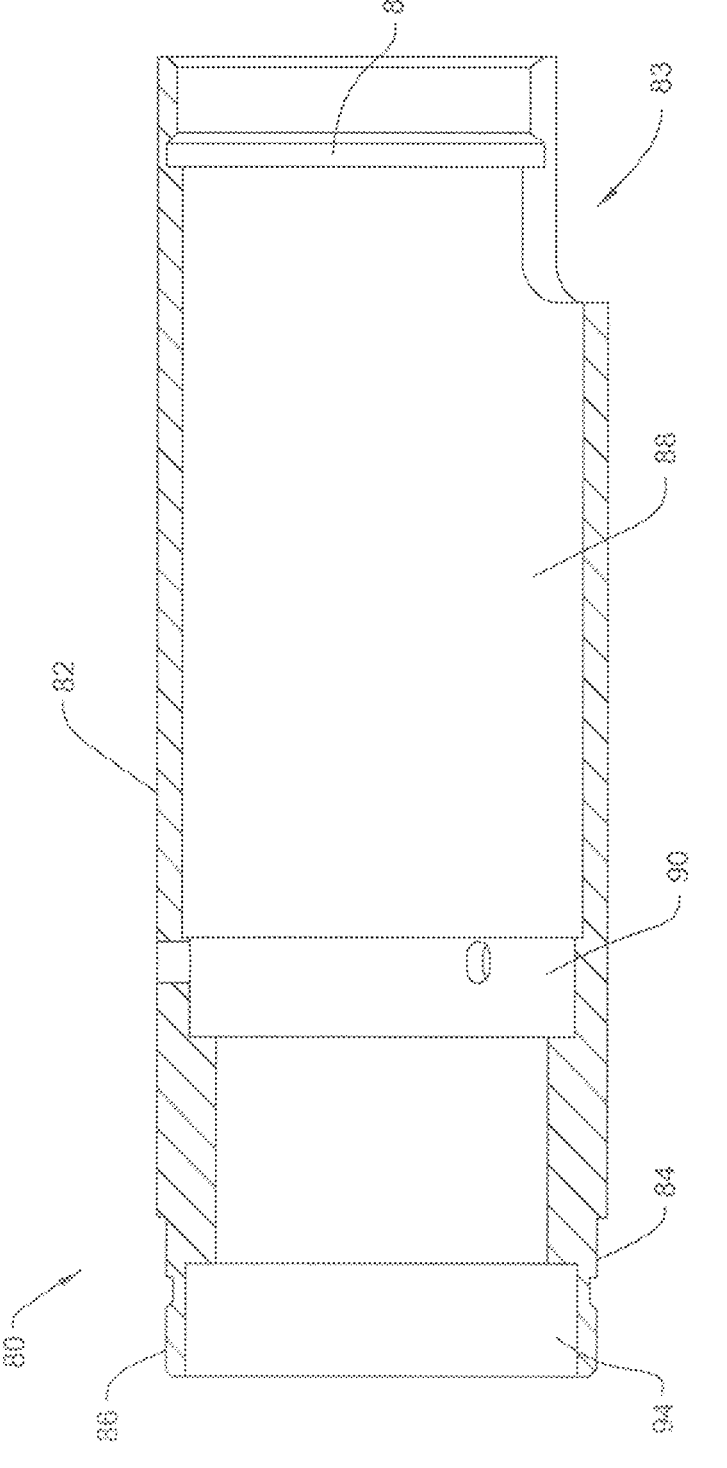
FIG. 5 is a cross sectional view of the saw motor housing.

FIGS. 2, 3 and 4 illustrate how motor 60 and saw head 68 are mounted to the rest of the saw 50, more particularly, the front plate 64. The motor 60 includes a tube-like motor housing 80 now described by reference to FIG. 5. The motor housing 80 is formed to have a main section 82 of constant diameter that extends distally forward from the proximal rear end of the housing. Main section 82 extends along approximately 80% of the length of the housing. Motor housing main section 82 is primarily cylindrical. Nevertheless, the main section 82 is formed to define a notch 83 that extends forward from the main section proximal end. Notch 83 functions as void space through which electrical connectors not illustrated and not part of this invention extend to the motor 60.

Forward of main section 82, the motor housing 80 has a first collar 84 with a smooth outer wall. Collar 84 has a diameter less than that of main section 82. A second collar 86 forms the most distal end of the motor housing 80. Second collar 86 has an outer diameter approximately equal to that of first collar 84. The outer surface of the motor housing 80 forming the second collar 86 is threaded, (threading not illustrated).

Motor housing 80 is formed to have a first bore 88 that extends distally forward from the proximal rear end of the housing. The motor housing 80 is further formed to define a groove 89 that extends circumferentially around a portion of the proximally located inner wall of the housing that defines the first bore. More particularly, the groove 89 is formed in the section of the main housing 80 interrupted by notch 83. Extending coaxially forward from the first bore 82, the motor housing is formed to have a second and third bores 90 and 92, respectively. Second bore 90 has a diameter less than that of the first bore 88. Third bore 92 has a diameter less than that of the second bore 90. Collectively, bores 88 and 90 are located in the housing main section 82. The third bore 92 extends from the main section 82 and into the space subtended by the first collar 84. A fourth bore 94, coaxial with bores 88, 90 and 92, forms the open distal end of the motor housing 80. Bore 94 extends through the motor housing second collar 86 and partially into the first collar 84.

Motor 60 includes a stator is represented in FIG. 3 by a number of wires 96 motor cap 110 and part of a lamination stack 97 in the housing first bore 88. The motor 60 is completed by a rotor 98 that is rotatably fitted in the housing first bore 88 and that is centered along the longitudinal axis of the motor housing 80. As seen by FIG. 3, rotor 98 is formed to have a proximal end stem 102. Not shown in the Figures is the bearing assembly that extends between the rotor stem 102 and the adjacent inner wall of the motor housing 80 that defines the first bore 88. Also not seen is the snap clip seated in groove 89 holds the bearing assembly and stator 96 in position.

Forward of stem 102, motor rotor 98 has a main section 104 with a diameter larger than that of the stem 102. The rotor main section 104 includes the motor magnets, (not explicitly illustrated). Forward of the motor main section 104 there is a neck 106 that has a diameter approximately equal to that of the stem. A circular head 108 forms the distalmost, forwardmost section of the rotor 98. Rotor head 108 has an outer diameter less than that of the adjacent neck 106. The rotor 98 is further formed with an axially extending bore 109 that extends between the proximal and distal ends of the rotor.

The rotor head 108 is rotatably mounted to a cap 110, seen best in FIG. 3, disposed in the distal most portion of the motor housing first bore 88. Cap 110 has a sleeve shaped outer skirt 112. A disc-like base 114 extends over the forward section of skirt 112. It will be observed that the distally directed face of cap base 114 is slightly recessed relative to the annular front surface of the skirt 112. The cap 110 is further formed to have a circumferential flange 116 that extends proximally rearward around the center of the cap base 114. Flange 116 has an L-shaped cross-sectional profile. The inwardly directed circumferential edge of flange 116 defines an opening 118 through the cap base 114.

Cap 110 is fit in the distal end base of the motor housing first bore 88. The rotor neck 106 extends through the cap opening 118; rotor head 108 is seated in the void space defined by the cap circumferential flange 116. A bearing assembly 120 extends between the rotor head 108 and the flange 114 to rotatably couple the rotor 98 to the cap 110.

Figure 6:
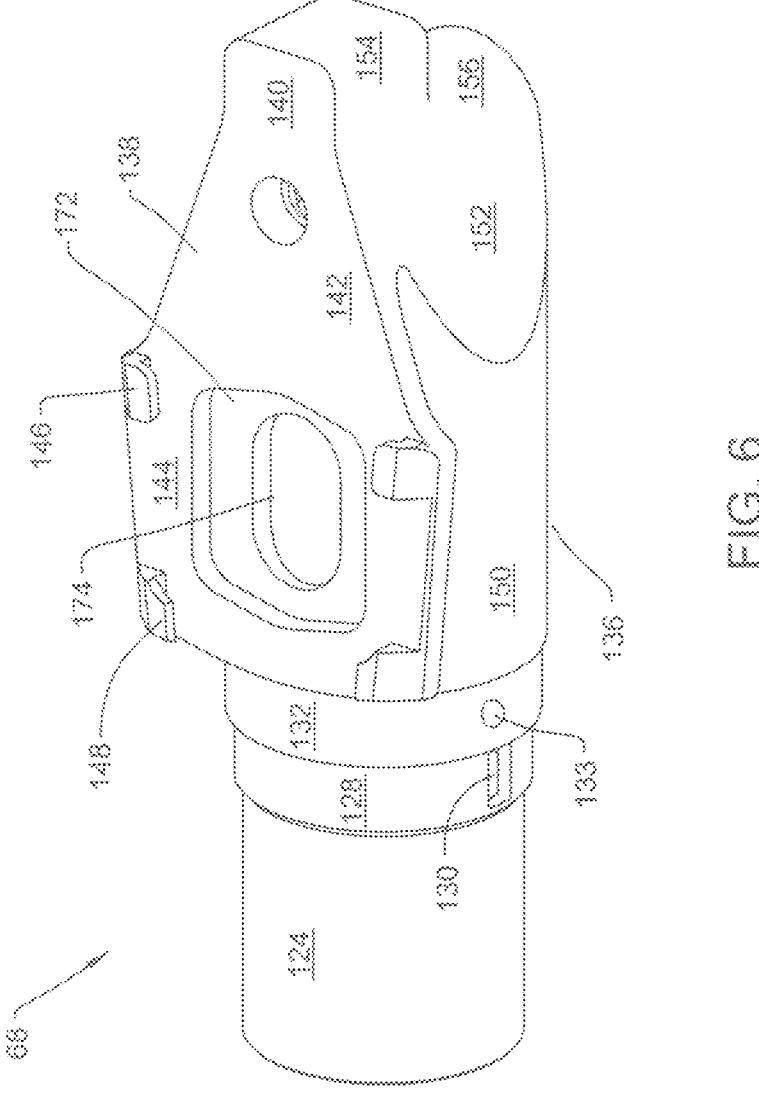
FIG. 6 is a perspective view of the saw head.
Figures 7, 7A:
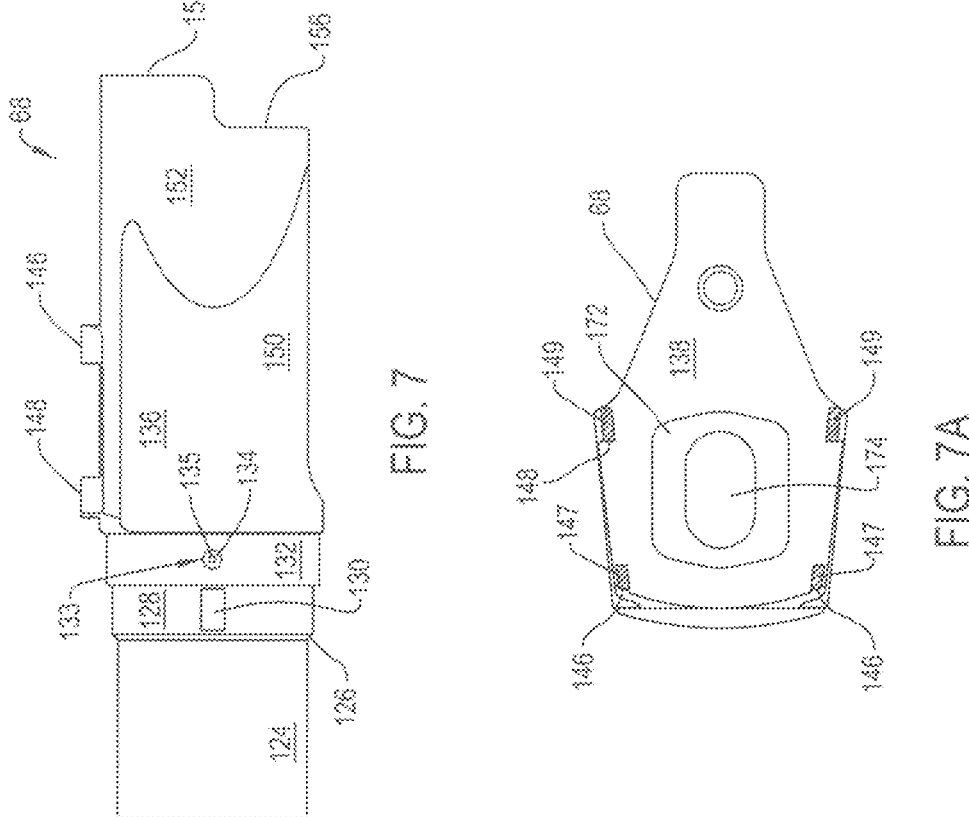
FIG. 7 is a side view of the saw head.
FIG. 7A is a top view of the saw head.
Figure 8:
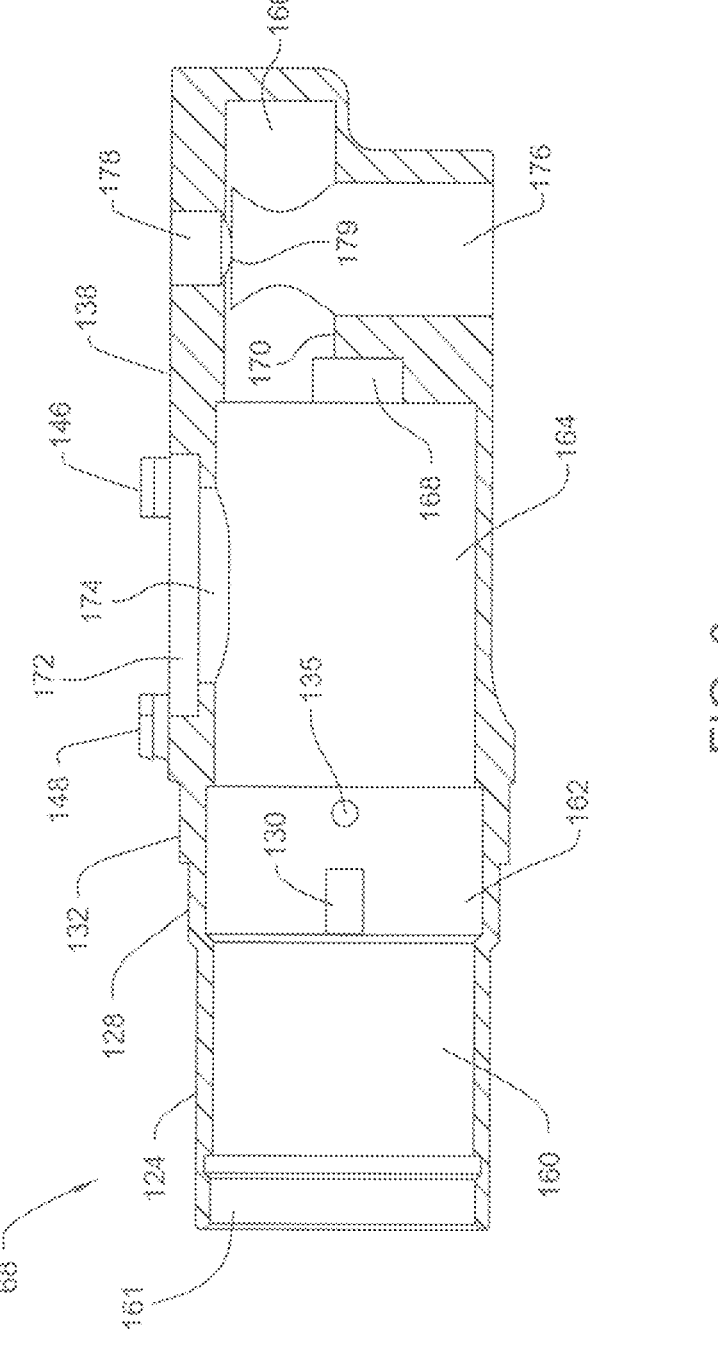
FIG. 8 is a cross sectional view of the saw head.

The saw head 68, now described by reference to FIGS. 6-8, is formed from a single piece of metal. The saw head 68 is formed to define a cylindrically shaped proximal end section 124. More specifically, proximal end section 124 has an outer diameter dimensioned to allow the section to freely rotate when fitted in the motor housing third bore 92. Forward of the proximal end section 124, there is a cylindrical first intermediate section 128. First intermediate section 128 has an outer diameter greater than that of the proximal end section and less than that of the motor housing fourth bore 94. Saw head 68 is formed so that between the proximal end section 124 and the first intermediate section 128 there is tapered surface 126. Saw head first intermediate section 128 is further shaped to define two rectangularly shaped, diametrically opposed through openings 130 into the center of the saw head 68.

A second intermediate section 132, also having a cylindrical cross-sectional profile, extends distally forward from the first intermediate section 128. Second intermediate section 132 has a diameter greater than that of the first intermediate section 128. The second intermediate section 132 is formed with a circular bore 133. Bore 133 is positioned so that center of the opening is located on a line that is an extension of the longitudinal axis of one of the saw head openings 130. A circular lip 134 formed integrally with saw head 68 defines the base of opening 134. Lip 134 also defines an opening 135 from bore 133 into the center of the saw head 68.

Saw head 68 also has a distal end section 136. The distal end section 136 has a planar top surface 138. The most forward section of top surface 138, section 140, has a rectangular profile. Extending proximally rearward, top surface 138 has a section 142 with opposed outwardly extending side edges such that width of the surface increases extending proximally rearwardly from section 140. Rearward from section 142, head top surface 138 has a section 144. The opposed side edges of section 144 taper inwardly such that the width of section 144 decreases extending proximally rearward along the section.

Saw head 68 is provided with two pairs of L-shaped brackets 146 and 148 that extend upwardly from and over top surface section 144. The brackets forming each bracket pair 146 and 148 are opposed from and directed inwardly towards each other so that the end of each bracket extends over the top surface 138. The brackets forming pair 146 are located in the forward part of top surface section 144 immediately proximal to where top surface 138 transitions from section 142 to section 144. The brackets forming bracket pair 148 are located immediately forward of the proximal edge of top surface section 144.

From FIG. 7A it can be appreciated that the brackets 146 and 148 are formed to have inner vertical surfaces 147 and 149, respectively, that extend up from saw head top surface 138. The brackets 146 and 148 are oriented so that surfaces 147 and 149 are angled inwardly along lines that are angled relative to the longitudinal axis of the saw head. Thus each pair of surfaces 147 and pair of surfaces 149 are on lines that intersect at points that are proximal extensions of the saw head longitudinal axis. In the illustrated version of the invention, brackets 146 and 148 are further oriented so that the surfaces 147 and 149 on each side of the saw head are collinear.

Below top surface section 144 and the proximal half of portion 142, saw head 68 has a curved surface 150 with a constant radius. Below the distal half of top surface section 142 and top surface section 140, the saw head 68 is shaped so that surface 150 merges into two opposed generally planar side checks 152. Immediately below top surface distal end portion 140, the saw head 68 is shaped to form a nose 154. Nose 154 has a cross sectional profile that, extending downwardly from top surface portion 140 approximates the shape of the top surface portion 140. Below nose 154, saw head 68 is shaped so that a curved chin 156 extends between side checks 152. The saw head 68 is further shaped so that chin 156 is recessed relative to nose 154.

Saw head 68 is further shaped to define five longitudinally extending contiguous bores 160, 162, 164, 166 and 168. Bore 160 is the most proximal of the saw head bores and forms a proximal end opening into the saw head 68. The bore 160 is located in the saw head proximal end section 124. Bore 160 is axially centered along the longitudinal center axis of the saw head 68. The saw head 68 is shaped to have an inner wall section 161 that forms the proximal end opening into bore 160 that is provided with threading (threading not illustrated). Not identified is the groove between inner wall section 161 and the more distal portions of the inner wall that defines bore 160. This groove is present for manufacturing purposes.

Bore 162 is contiguous with, coaxial with and extends distally forward from bore 160. Bore 162 is located within the first and second saw head intermediate sections 128 and 132, respectively. The bore 162 has a diameter larger than that of bore 160. Both saw head openings 130 and the opening 135 open into bore 162. The bore 164 is contiguous and coaxial with and projects distally forward from the bore 162. The saw head 68 is shaped so that bore 164 has a diameter equal to the diameter of bore 160. Bore 164 is formed in the portion of the saw head subtended by curved surface 150.

Bores 166 and 168 are partially overlapping closed end bores that both extend longitudinally distally forward from the front of bore 164. Bore 166 is the longer of the two bores 166 and 168. Bore 166 extends into the saw head nose 154. Thus, bore 166 is not coaxial with bores 160, 162 and 164. The bore 168 is located below and partially overlaps bore 166. Bore 168 only extends a relatively short distance forward of bore 164. Bore 168 terminates at the surface of a web 170 internal to the saw head 68.

The saw head 68 is further formed to have two contiguous openings 172 and 174 in the top surface portion 144. Opening 172 forms a recess in the top surface. The opening 172 is approximately rectangularly shaped such that the longitudinal axis of is parallel with the longitudinal axis of the saw head 68. While opening 172 is generally rectangularly shaped, the longitudinally extending sides do have outwardly extending apices (not identified) that are centered on the longitudinal axis of the opening. The apex of the proximally directed edge is directed proximally; the apex of the distally directed edge is directed distally. Opening 174 extends downwardly from the base of opening 172 into saw head bore 164. Opening 174 is oval shaped and subtends less area than opening 172.

A bore 176 extends upwardly from the bottom of the saw head 68 at a location proximal to distal facing chin 156. Bore 176 opens into the longitudinally extending bore 166. A bore 178 extends downwardly from the saw head top surface portion 140 into bore 166. The bore 178 is coaxial with and has a smaller diameter than bore 176. It will further be noted that saw head 68 is formed to have a small annular inwardly directed lip 179 projects into bore 176. Lip 179 forms the base of bore 178.

When saw 50 is assembled, the saw head 68 is fit into the motor housing 80 so that the proximal end section 124 fits in the motor housing third bore 92 as best seen in FIG. 3. Two sets of ball bearings 182 facilitate the rotation of the saw head 68 relative to the motor housing 80. A first set of bearings 182 extend around the saw head proximal end section 124 in a circle that is immediately distal to the proximal end of the saw head. These bearings 182 are sandwiched between an inner race 184 and an outer race 186. The inner race 184, seen in FIG. 9, has a ring shaped main body 188. A flange 190 extends radially outwardly from the main body 188. The flange 190 is located closer to the distal end of the race main body 188 than the proximal end. The inner race 188 is further formed to have a distally facing, outwardly tapered surface 192 that extends from flange 190 to the distal end of the main body 188.

FIG. 10 illustrates outer race 186. Generally, outer race 186 is in the form of a ring. The outer race 186 is further formed to define a circumferential groove 187 that is located proximal of the distally directed front end of the race and that extends around the inner perimeter of the race.

When the saw 50 of this invention is assembled, the outer race 186 is seated against the circular stepped inner surface of the motor housing 80 that defines the transition between the second and third bores 90 and 92, respectively. Ball bearings 182 are fitted in annular groove 187. Inner race 184 is fitted over the saw head proximal end section 124 so that tapered surface 192 presses against the ball bearings 182.

A wave spring 181, seen in FIG. 3, extends between the proximally directed face of inner race flange 190 and a head retainer ring 193. As seen in FIG. 11, head retainer ring 193 has a sleeve like main body 194 the outer surface of which is threaded (threading not illustrated). An annular lip 195 extends radially outwardly from the distal end of ring main body 194. Ring lip 195 is formed with notches (not identified) to facilitate use of a fastening tool. During assembly of the saw 50, the head retainer ring main body 194 is screw secured to the complementary threading around proximal end section 161 of saw head bore 160. The proximal end of the wave spring 181 seats against the static, forward facing surface of ring lip 195.

Wave spring 181 thus imposes a forward directed force on the inner race that presses the flange tapered surface 192 against the ball bearings 182. The lip 195 of the head retainer ring 193 functions as the structural member that holds the saw head 68 to the motor housing 80.

The forwardly-located set of ball bearings 182 seat against the annular tapered surface 126 of the saw head. An outer race 196 disposed in the motor housing distal most, fourth bore 94 of the motor housing 80 also surrounds this set of ball bearings 182. The outer race 196, best seen in FIGS. 12 and 13 has a circular, proximally located base ring 198. The outer race base ring 198 is shaped to tightly press fit in the motor housing fourth bore 94. Base ring 198 is further shaped to have a circumferentially extending lip 202. When the saw 50 is assembled, the outer race 196 is positioned in motor housing bore 94 so that the outer surface of lip 202 seats against the inner surface of the motor housing that defines bore 94. Collectively, lip 202 and the adjacent inner surface of the race base ring 198 are shaped to define a groove 204 that has an inwardly shaped profile. The outer race 196 is shaped so that groove 204 has a radius that accommodates the seating of ball bearings 182.

Outer race 196 is further formed to have a cylindrical skirt 206 that extends distally forward of the base ring 198. The skirt 206, which is integral with the base ring 198, has an outer diameter less than that of the base ring. Outer race skirt 206 is further formed so that the most forward section thereof has inner wall that is outwardly stepped relative to the remaining proximally located section. In the Figures, annular, radially extending step 208 defines the transition between the two wall sections. Step 208 thus divides the race skirt 206 into a thick walled section and a smaller thin walled section. The outer race is further formed to define a number of circumferentially equangularly spaced apart openings 210. Each opening 210 has a rectangular cross section and extends longitudinally through a thick walled portion of the skirt 206 and a small portion of the adjacent outwardly stepped thin walled section.

When the saw 30 is assembled, the distal most ball bearings 182, in addition to seating against saw head tapered surface 126, seat in outer race groove 204.

During assembly, motor housing 80 is fitted to the saw front plate 64. Specifically, the motor housing is fitted to the front plate 64 so that the housing first collar 84 seats in an opening 212 formed in the front plate 64. A threaded ring 214, best seen in FIGS. 4 and 14, is fitted over the housing second collar 86 to hold the motor housing to the front plate 64. Ring 214 is formed with a circular skirt 216 that forms the main body of the ring. The inner cylindrically shaped wall of ring skirt 216 is formed with threading, not illustrated. The ring 214 is further formed so that skirt 216 has an outwardly flared outer wall. A circular lip 218 extends inwardly from the distal end face of skirt 216.

While not illustrated, it should be understood that an anti-rotation pin may be fitted in a groove formed in the outer surface of the motor housing 80. This pin extends beyond the perimeter of the cylindrical motor housing 80 into a complementary notch formed in the front plate 64. This notch is contiguous with and extends beyond the perimeter of plate opening 212. The pin thus prevents rotation of the motor housing 80 relative to the front plate 64.

At assembly, the ring 214 is screw fitted over the motor housing second collar 86. The proximally facing base of ring skirt 216 bears against the adjacent distally directed face of the front plate 64. This action causes the motor housing 80 to move forward until the laterally extending stepped surface of the housing 80 between main section 82 and the first collar 84 bears against the inner, proximally directed face of the front plate 64. The motor housing 80 is thus compression locked to the front plate 64 by the annular step around the motor housing first collar 84 and ring 214.

During the process of assembling saw 50, blade drive assembly and blade coupling assembly components described below are assembled into the saw head 68. Saw head proximal end section 124 is then fitted to the motor housing 80 to extend through the housing third bore 92 so as to project a short distance into the second bore 90. Retaining ring 193 is screw fitted to the complementary threading around the saw head inner wall section 161. Prior to the coupling of the retaining ring 193 in position, the proximal located ball bearings 182, the inner race 184 and wave spring 181 are positioned around the saw head proximal end section 124.

An indexing lock link 224, now described by reference to FIGS. 15 and 16, holds the saw head 68, and the components disposed therein, at a fixed angular orientation relative to the longitudinal axis of the motor housing 80. Lock link 224 includes a base 226 in the form of a rectangular bar. At the proximal end, a lock tongue 228 extends upwardly from base 226. Lock link tongue 228 is in the form of rectangular block dimensioned to closely slip fit into one of the rectangular openings 210 of outer race 196. The lock link 224 is further shaped to have a post 230 that extends upwardly from the base 226 at a location proximal to the distal end of the base.

Figure 17:
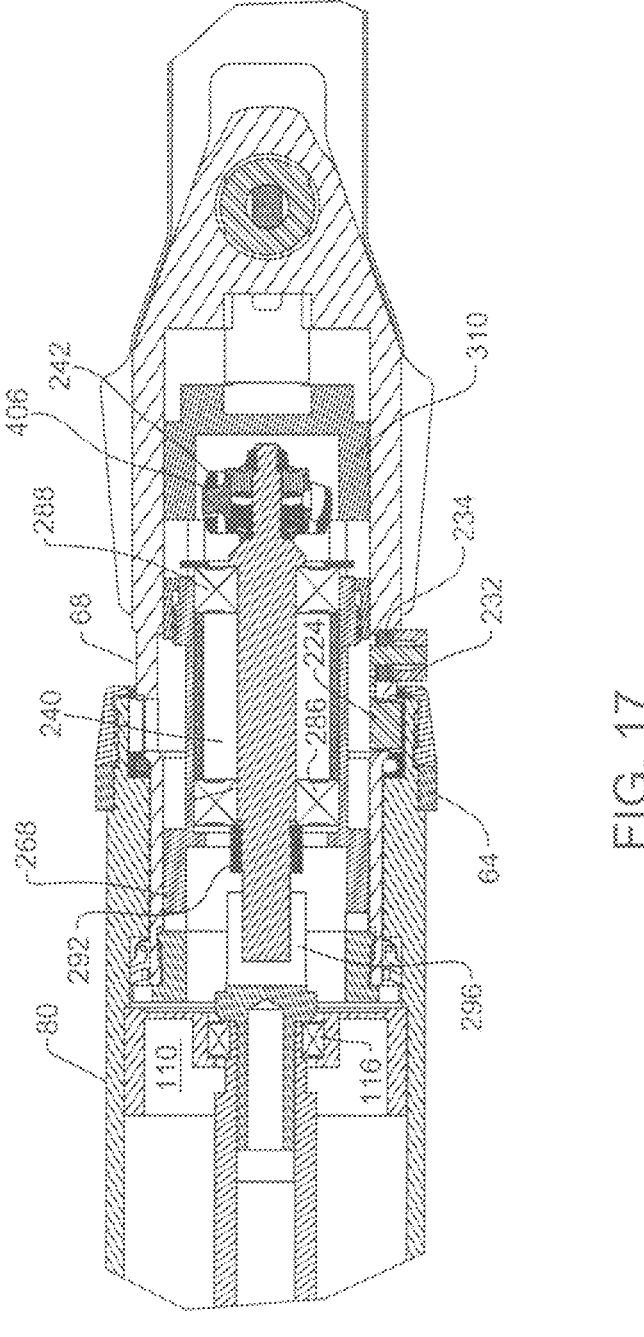
FIG. 17 is an enlarged cross sectional view of illustrating how the indexing lock link holds the saw head in a select orientation.

As seen in FIG. 17, the lock link 224 is seated in saw head bore 162. Lock link 224 is positioned so that post 230 extends through opening 135 into bore 133. Lock link tongue 228 extends through the adjacent opening 130 formed in the saw head 68. A release button 232 is secured over the exposed end of post 230. A coil spring 234 extends between the underside of the release button 232 and the adjacent static annular lip 134 of the saw head 68 that defines the base of bore 133. Spring 234, by working against button 232, exerts an outward force on the lock link 224. This force normally causes base 226 to seat against the inner surface of the saw head that defines bore 162 so that tongue 228 normally projects through opening 130.

When the saw 50 is assembled, the saw head openings 130 are aligned with the cross sectional slice section of the motor housing 80 in which the openings 210 of outer race 196 are located. Lock link tongue 228, when it extends through the saw head opening 130, seats in one of the race openings 210. This engagement of the lock link 224 with the outer race 196 locks the saw head 68 in a fixed angular orientation relative to the longitudinal axis of the motor housing. The depression of button 234 causes lock link 224 to move towards the center of saw head 68. This causes the link tongue 228 to retract out of the race opening 210 in which it is seated so as to release the saw head from the locked position. The surgical personnel can then rotate, index, the saw head 68 to the desired angular orientation. Once the saw head 68 is so positioned, button 232 is released. Spring 234 moves the lock link back to the locked state so the tongue 228 seats in the adjacent race opening 210 to again hold the saw head in position.

III. Blade Drive Assembly

An output shaft 240 disposed in the saw head 68 receives the rotation moment output by the motor rotor 98. A bearing assembly, also internal to saw head 68, converts the rotary moment into motion that oscillates oscillating shaft 242 also located in the saw head. Oscillating head 70 is coupled to the oscillating shaft 242 to move in unison with the oscillating shaft.

Figures 18, 19:
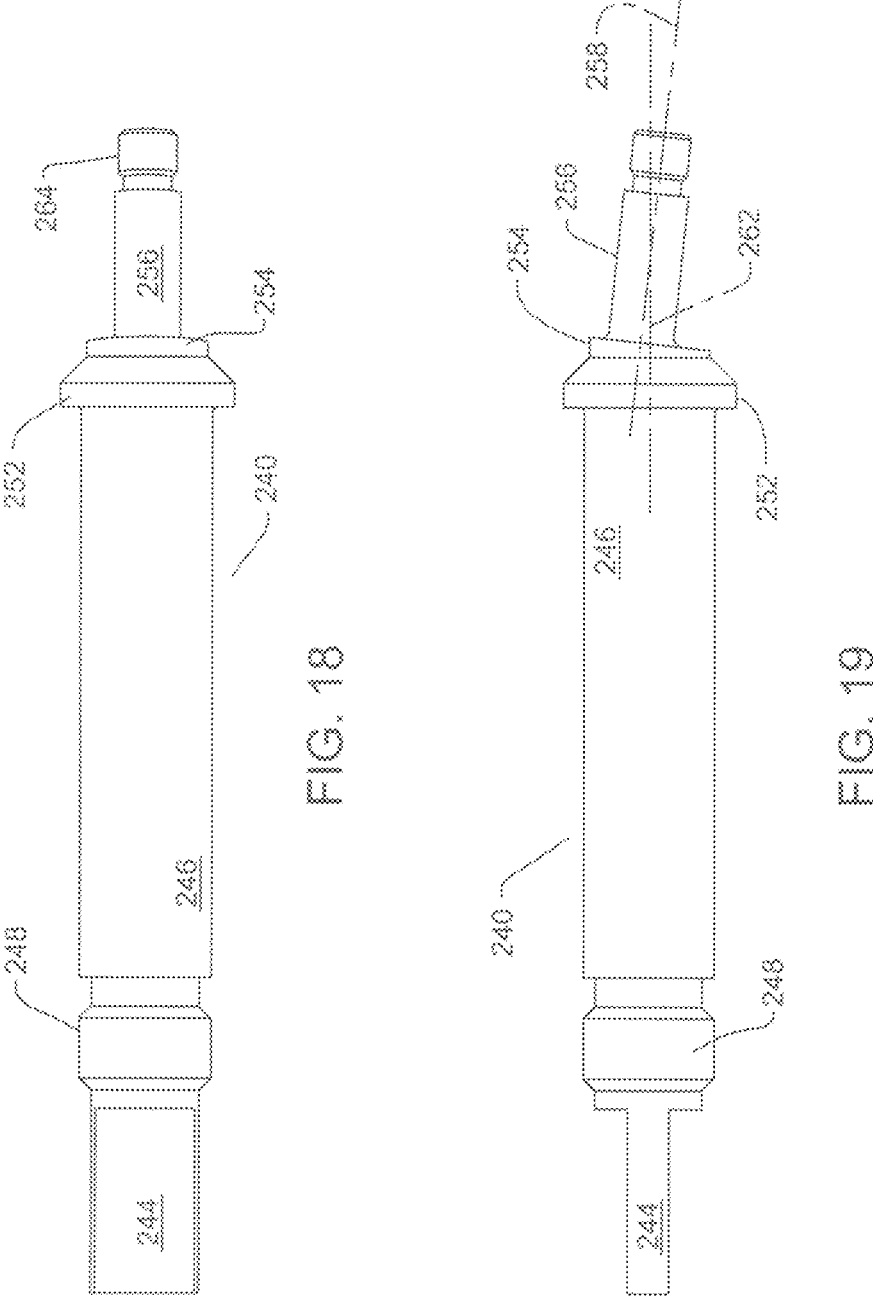
FIG. 18 is a first plan view of the saw output shaft.
FIG. 19 is a second plan view of the saw output shaft at position different from that shown in the first plan view.

In more detail, the output shaft 240, seen best in FIGS. 18 and 19, is a single elongated solid piece of metal. At the most proximal end, output shaft 240 is shaped to have a generally rectangularly shaped stem 244. Forward of stem 244, output shaft 240 has a cylindrical main section 246. The center axis of the main section is aligned with the center longitudinal axis of stem 244. The main section 246 is formed to have a proximal end portion 248 that is provided with threading (not illustrated). Not identified is the annular groove between the shaft proximal end portion and the remaining more distally located portion. The groove facilitates manufacture of the output shaft 240.

Forward of and coaxial with the main section 246, the output shaft 240 is formed to have a collar 252 Collar 252 has an outer diameter greater than that of main section 246. A neck 254 with a diameter less than that of shaft main section 246 extends forward from the collar 252.

A shaft head 256 projects forward of the collar 252. The output shaft 240 is formed so that head 256 is not coaxial with the more proximally located sections of the shaft. Instead, shaft head 256, which is cylindrical in shape, is centered on an axis that is between approximately 5 and 7° off set from the longitudinal axis through the shaft main section. Further, shaft head 256 extends forward from neck 254 at a such that, as seen in FIG. 19, the longitudinal axis of the head, represented by line 258, does not extend from the distal end terminus of the longitudinal axis that extends through the shaft main section 246, collar 252 and neck 254, (line 258). Instead, shaft head 256 is positioned so that the head longitudinal axis intersects a line, dashed line 262, representative of the extension of the primary longitudinal axis at a point forward of the shaft neck section 254.

A nose 264 extends forward from the free distal end of the shaft head 256. Threading, not illustrated is formed over the outer cylindrical surface of nose 264.

Output shaft 240 is rotatably mounted in a rear inner housing 268 that is slidably fitted in the saw head bore 160. As seen in FIG. 20, the rear inner housing 268 is a multi-section structure. The most proximal section of the rear inner housing is a base 270. The base 270 has an outer diameter that facilitates the close sliding movement of the base in the saw head proximally-located bore 160. One or more notches 271 (one seen) extend distally inward from the proximal end of the base 270. Notches 271 facilitate the use of an assembly/disassembly tool (not illustrated).

Extending forward from base 270, rear inner housing 268 has a generally cylindrical stem 272. The stem 272 has an outer diameter that is less than that of the base 270. While not illustrated, the rear inner housing stem 272 may be formed with windows to reduce the overall weight of the rear inner housing 268. The rear inner housing 268 is formed to have a head 274 located immediately distally forward of the stem 272. Head 274 has an outer diameter between that of the base 270 and the stem 272. The outer surface of the rear inner housing head 274 is provided with threading (not illustrated). A nose 276 forms the most distal section of the rear inner housing 268. Nose 276, which is located immediately forward of head 274, has a diameter between that of the stem 272 and the head 274.

Rear inner housing 268 is further formed to have proximal and distal bores 278 and 280, respectively. Proximal bore 278 is located within the housing base 270. The distal bore 280 extends through the housing stem 272, head 274 and nose 276. Distal bore 280 has a diameter less than that of the proximal bore 278. The rear inner housing is further formed so that, within the base 268 at the distal end of the base, there is an annular, inwardly extending ledge 282. Ledge 282 separates the distal end base of proximal bore 278 between the proximal end base of the distal bore 280. The inner edge of ledge 282 defines an opening 284 in the rear inner housing 268 between the proximal and distal bores 278 and 280, respectively. Opening 284 has a diameter less than that of the distal bore 280.

Two bearing assemblies 286 and 288, seen best in FIG. 4, rotatably hold output shaft 240 in the rear inner housing 268. Bearing assembly 286, the proximal of the two assemblies, is disposed over the smoothed walled portion of the shaft main section 246 immediately forward of proximal end portion 248. Bearing assembly 288, the distal-located bearing assembly, is positioned over the shaft main section 246 immediately proximal to the shaft collar 252. A sleeve-shaped spacer 290 extends between the outer races of the bearing assemblies 286 and 288 to hold the assemblies apart. (The individual races of bearing assemblies 286 and 288 not illustrated.)

A retaining nut 292 holds the bearing assemblies 286 and 288 and spacer 290 to the output shaft 240. Nut 292 threads over the threading formed on the shaft main section partial end portion 248 to abut the inner race of bearing assembly 286. When saw 50 is assembled, the outer race of bearing assembly 286 seats against the distally directed face of rear inner housing ledge 282. The shaft stem 244 extends through the rear inner housing bore proximal bore 278 and a short distance into the center void of the head retainer ring main body 194.

A drive coupler 296 attached to the motor rotor 98 couples the output shaft 240 to the rotor so the two components rotate in unison and the shaft 240 can longitudinally move relative to the rotor 98. As seen in FIG. 21, drive coupler 296 is formed from a single piece of metal and is formed to have a tubular stem 298. Stem 298 is dimensioned to be press fit in rotor bore 109 so that the rotor 98 and drive coupler 296 function as a single unit. The stem 298 is formed with a bore 299. Bore 299 is present to relieve the stress associated with the press fitting of the stem 298 in motor rotor bore 109. Forward of stem 298, the drive coupler 296 has a collar 302. Collar 302 has a diameter greater than that of rotor bore 109 to limit the extent to which the drive coupler 296 is press fit into the rotor bore.

Forward of collar 302, drive coupler 296 has a cylindrical head 304. While the drive coupler head 304 is generally solid, the head is formed define a slot 306 that extends diametrically across the head. Slot 306 has a width that allows the output shaft stem 244 to slidably move within the slot. Upon assembly of the saw 50, the output shaft stem 244 is slidably fitted in drive coupler slot 306 so that, upon rotation of the motor rotor 98, the output shaft 240 rotates with the rotor.

Figures 23, 24:
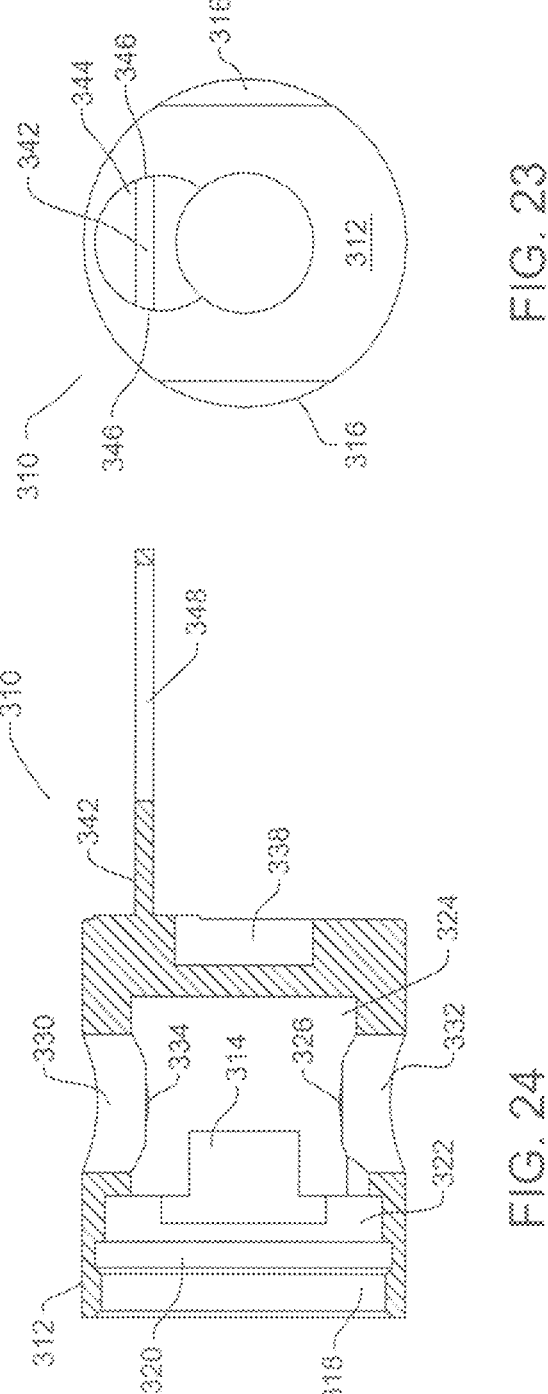
FIG. 23 if a front plan view of the front inner housing.
FIG. 24 is a cross sectional view of the front inner housing taken along line 24-24 of FIG. 22.
Figures 25, 26, 27:
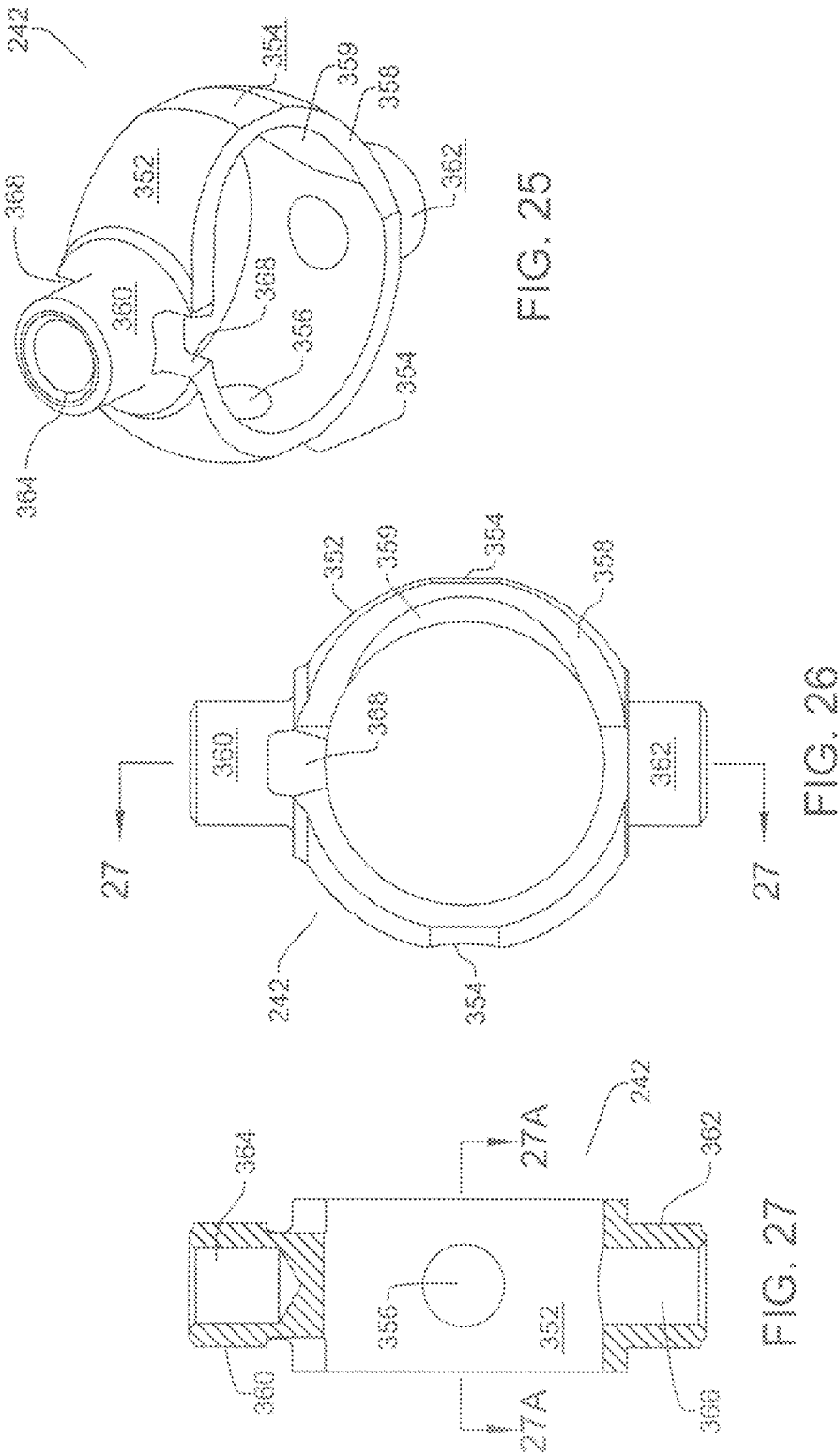
FIG. 25 is a perspective view of the oscillating shaft.
FIG. 26 is side plan view of the oscillating shaft.
FIG. 27 is a cross sectional view of the oscillating shaft taken along line 27-27 of FIG. 26.
Figure 27A:
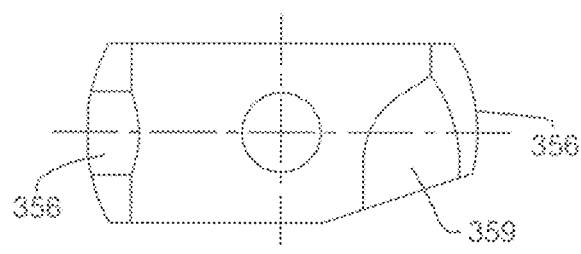
FIG. 27A is a cross sectional view of the oscillating shaft taken along line 27A-27A of FIG. 27.

A front inner housing 310 surrounds the distal end of the rear inner housing 268 and the portions of the output shaft 240 forward of the rear inner housing. Front inner housing 310 is the component to which the oscillating head 70 and oscillating shaft 242 are rotatably mounted. As best seen in FIGS. 22-24, front inner housing 310 includes a base 312. Generally, base 312 has a cylindrical shape. The outer diameter of the front inner housing base 312 is dimensioned to allow the base to slidably fit in saw head bore 164. Base 312 is further shaped so that, forward the proximal end, the base defines two windows 314 into the center of the base. Base 312 is further formed to have two opposed notches 316 that extend inwardly from distally directed front face of the base. Both windows 314 and notches 316 are provided to facilitate manufacture of the saw 50.

Front inner housing base 312 is further formed to have a number of bores and openings. A first bore 318 extends forwardly inward from the proximal end of the base 312. The circular inner wall of base 312 that defines bore 318 is provided with threading, (not identified). More specifically, the inner housing base 312 is formed so that the threading around bore 318 can screw secure this bore-defining section of the inner housing 268 to the adjacent rear inner housing head 274. Immediately in front of bore 318, front inner housing 310 has a second bore 320. Bore 320 has a diameter greater than that of bore 318. Bore 320 exists as a result of the manufacturing processes and is not otherwise material to this invention.

Forward of bore, 320, the front inner housing base 312 is shaped to have a bore 322. Bore 322 has a diameter less than that of the proximal end bore 318. More specifically, the front inner housing 310 is formed so that base 312 is shaped so that the rear inner housing nose 276 can snugly fit in bore 322. A closed end bore 324 extends distally forward of bore 322. Bore 324 has a diameter less than that of bore 322. It should be appreciated that bores 320, 322 and 324 are coaxial with the longitudinal axis of the rear inner housing base 312. Windows 314 open into bores 322 and 324.

The front inner housing base 312 is formed with opposed, axially aligned top and bottom openings 330 and 332, respectively, which extend into bore 324. During manufacture of front inner housing 310, material is left to define around the bases of opening 330 and 332 arcuately shaped, diametrically opposed ledges 334 and 336, respectively. Ledges 334 extend into the space immediately below the base of opening 330. Ledges 336 extend into the space immediately above the base of opening 332.

Front inner housing 310 is further formed to have a bore 338 that extends inwardly, proximally rearward from the distally directed front face of base 312. Bore 338 is closed ended and terminates on the opposite side of the interior wall of the housing base at which bore 324 terminates.

Formed integrally with and extending forward from base 312, front inner housing has a nose 342. In FIG. 23, the nose 342 is shown extending forward from a generally circular boss 344 that itself extends forward from the front face of the base 312. Bore 338 intersects boss 344. Boss 344 exists as a result of the processes employed to machine the front inner housing 310 and is not otherwise relevant to this invention.

Nose 342 is in the form of an elongated plate. Nose 342 is further formed to have opposed longitudinally extending side edges 346 that are symmetrical inwardly curved. The radius of curvature of the race nose side edges 346 matches the radius of surrounding saw head bore 166 and the nose is free to move in bore 166. The front inner housing nose is also formed to have a longitudinally extending oval through slot 348. Opening 348 is centered on the longitudinal axis of the nose 342.

As best seen in FIGS. 25-27 and 27A, oscillating shaft 242 includes a ring shaped center section 352. The outer surface of shaft center section 352 is generally in form of slice section through the center of a sphere; the outer surface is curved along two perpendicular radii. Center section 352 is further formed to have two opposed surfaces 354 on the outside of the section 352 along the middle of the section. Surfaces 354 have outer surfaces that are curved along a single radius that extends perpendicularly from the longitudinal axis of the shaft. Shaft center section 352 is further formed to define an opening 356 that extends through one of the surfaces 354. Shaft center section 352 is also shaped so to define a chamfer 358 on the side opposite the side in which opening 356 is formed. Chamfer 358 extends outwardly from the inner wall of the cylindrical inner wall that defines the opening through the center section 352.

Center section 352 is further formed to have a recessed surface 359 that extend inwardly from the generally cylindrical inner wall of the center section. The recessed surface 359 is formed by a ball mill cut process. Recessed surface 359 is formed to facilitate assembly of the components forming the blade drive assembly.

Oscillating shaft 242 is further formed to have diametrically opposed, axially aligned, cylindrically shaped head 360 and stem 362 that extend outwardly from the center section 352. Head 360 is formed with a downwardly extending closed end threaded bore 364. Stem 362 is formed with a threaded through bore 366 (threading not shown) that extends into the enclosed circular space defined by the center section. The oscillating shaft 242 is further formed to define notches 368 that extend inwardly from one of the outer faces of the center section to head 360. The shaft is formed so that the surfaces that define the side walls of notches 368 taper inwardly toward each other.

Figure 29:
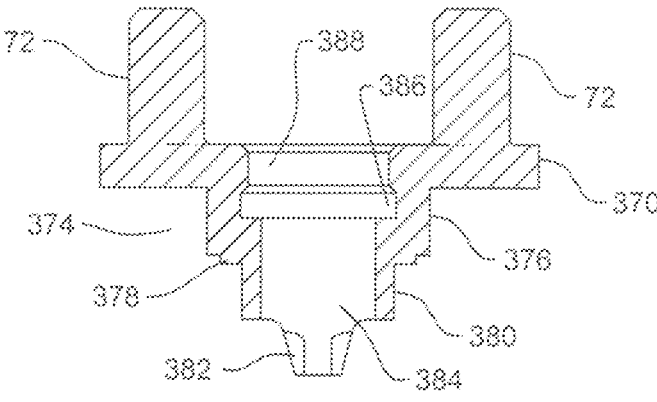
FIG. 29 is a cross sectional view of the oscillating head taken along line 29-29 of FIG. 29.

As seen in FIGS. 28 and 29, the oscillating head 70 is formed to have an elongated top plate 370. Top plate 370 is shaped to be widest along the lateral axis of the plate and narrowest at the opposed ends. The ends of top plate 70 are curved. Pins 72 extend upwardly from the opposed sides of the top plate 70. Oscillating head 70 is further formed to have a circular boss 374 that extends downwardly from the center of the top plate 370. Boss 374 has a first section 376 immediately adjacent the top plate 70 with a first diameter.

Below the first section 376 there is a boss second section 378. The boss second section 378 has a diameter less than that of the first section 376. Boss 374 is further formed to have a third section 380 immediately below the second section. Below the boss third section 380, oscillating head 70 is formed to have a pair of diametrically opposed, spaced apart feet 382 (one shown in FIG. 29).

Oscillating head 70 is further formed to have a bore 384 that extends upwardly between feet 382 and through boss 374. The oscillating head bore 384 is shaped to facilitate therein in close sliding fit, if not compression fit, the oscillating shaft head 360. More particularly, the oscillating head 70 is formed to define first and second counterbores 386 and 390, respectively, located above bore 384. First counterbore 386 is formed in the portion of the boss first section 376 immediately below the head top plate 370. First counterbore 386 has a diameter greater than that of bore 384. Second counterbore 388 forms the opening into bore 384 through the top plate 370. The second counterbore 388 has a diameter between that of bore 384 and first counterbore 386. Second counterbore 388 is provided with threading to facilitate attachment of a disassembly tool (threading and tool not illustrated).

Figures 30, 31, 32:
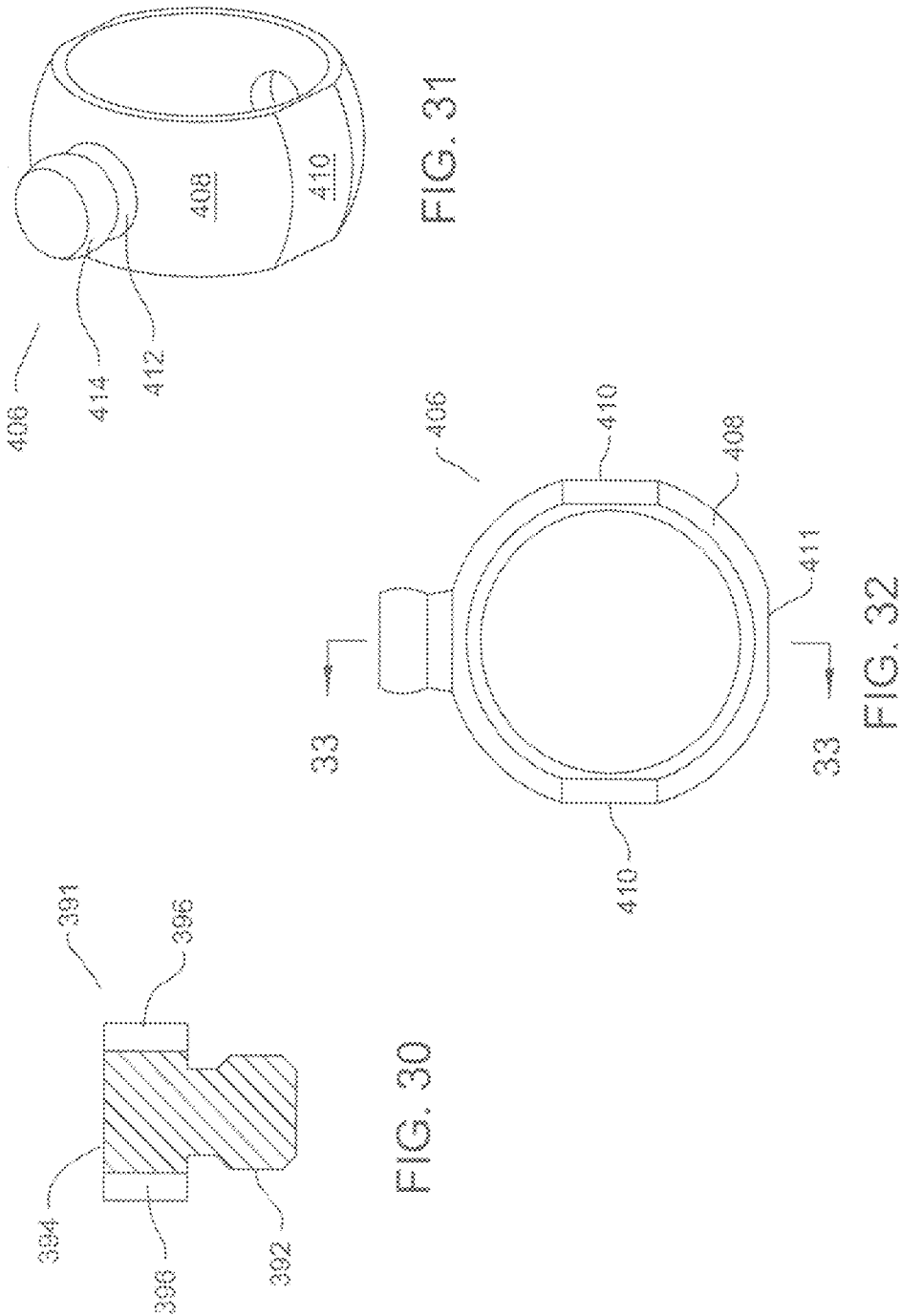
FIG. 30 is a cross sectional view of the shaft screw fitted to the oscillating shaft.
FIG. 31 is a perspective view of the wobble ring.
FIG. 32 is a plan view of the wobble ring.

The oscillating head 70 and oscillating shaft 242 are coupled together by fitting the shaft head 360 in the oscillating head bore 384. The oscillating head feet 382 are seated separate oscillating shaft notches 368. The seating of the feet 382 in notches 368 blocks the rotation of the oscillating head 70 relative to the shaft 242. A shaft screw 391 is screw secured in the oscillating shaft head bore 364. As seen in FIG. 30, shaft screw 391 has a cylindrical shaft 392. The outer surface of screw shaft 391 is provided with threading, (not illustrated) to screw secure the shaft into the oscillating shaft head bore 364. Above foot 392, shaft screw 391 is formed with a head 394 that is the widest diameter portion of the screw. More particularly, the shaft screw 391 is formed so that the downwardly directed annular outer face of the head 394 disposed around the shaft 392 the adjacent annular stepped surface of that defines the base of the oscillating head first counterbore 386.

Notches 396 (two shown in FIG. 30) are formed in screw head 394 to extend longitudinally along the outer perimeter of the head. Notches 396 are provided to receive a fastening tool.

Returning to FIG. 4, it can be seen that the oscillating shaft and oscillating head sub-assembly extends through front inner housing top opening 330, bore 324 and bottom opening 332. A bearing assembly 398 rotatably holds the oscillating head 70 in the front inner housing opening 330. More particularly, the outer race of bearing assembly 398 (races not explicitly identified) fits against the inner circular wall of the front inner housing 310 that defines opening 330. The inner race of the bearing assembly 398 surrounds the third section 380 of boss 374 integral with oscillating head 70. Downward movement of the bearing assembly 398 is limited by the abutment of the assembly outer race against the opposed ledges 334. The annular, downwardly directed face of the second section 378 of the oscillating head boss 374 presses against the top surface of the inner race of bearing assembly 398. Thus, front inner housing ledges 334 and oscillating head boss 374 collectively cooperate to prevent longitudinal movement of bearing assembly 398.

A bearing assembly 402 rotatably couples the oscillating shaft 242 in front inner housing opening 332. The outer race of bearing assembly 402 is disposed around the perimeter wall of opening 330. The inner race of bearing assembly 402 (races not explicitly identified) seats over oscillating shaft stem 362. The upwardly directed face of the outer race abuts against the opposed front inner housing ledges 336. A screw 404 is threaded into bore 366 integral with the oscillating shaft stem 362. The head of screw 404 bears against the downwardly directed face of the inner race of bearing assembly 402. Thus front inner housing ledges 336 and screw 404 collectively cooperate to prevent longitudinal movement of the bearing assembly 402.

Collectively, bearing assemblies 398 and 402 hold the oscillating head and shaft 70 and 242, respectively, to the saw head 68 so that these components can rotate about their colinear longitudinal axes.

A wobble ring 406 is part of the assembly that transfers the rotational moment of the output shaft 240 into motion that oscillates the oscillating shaft 242. The wobble ring 406 is disposed over the output shaft head 256 and seated in the oscillating shaft center section 352. Wobble ring 406, seen in FIGS. 31-33, output includes a ring shaped base 408. The inner circular surface of the ring base 408 has a linear profile. The outer circular surface of the ring base 408 has a profile of a slice section through the center of a sphere. Wobble ring base 408 is further formed to have on the sides, two diametrically opposed surfaces 410. Surfaces 410 have single curvature, around a radius perpendicular to the longitudinal axis of the wobble ring. Wobble ring base 408 is further formed to have a flat 411 located between opposed surfaces 410. Surfaces 410 and flat 411 exist for manufacturing reasons.

The wobble ring 406 is further formed to have a head 414 that is disposed above the base 408. The head 414 is connected to the base by a post 412. In the illustrated version of the invention, post 412 has a generally conical shape. The post 412 extends upwardly from the base at a position diametrically opposite flat 411. Head 414 is shaped to have geometry that equal to that of a truncated sphere. Opposite post 412, wobble ring base 408 is formed to have an opening 416 through flat 41. Opening 416 is provided for assembly purposes.

A bearing assembly 418, seen in FIG. 4, is disposed over the output shaft head 256 rotatably couples wobble ring 406 to the shaft head. A fastener 420 disposed over the output shaft nose 264 holds the wobble ring 406 and bearing assembly 418 to the output shaft 240.

Upon assembly, the wobble ring 406 is seated in the oscillating shaft center section 352 so that wobble ring head 414 seats in shaft opening 356. As a result of this engagement, when the output shaft 240 rotates, the wobble ring is prevented from rotating with the output shaft 240. Instead, the wobble ring 406 oscillates back and around the point where the line that extends from intersection of axis of the main body of the output shaft 240 and the axis of the shaft head 256. This oscillatory movement is transferred through the wobble ring 414 to oscillating shaft 240.

A coil spring 422, (seen only in FIG. 2) is disposed in the saw head 68. One end of the spring 422 seats against the interior wall of the saw head 68 that defines the base of saw head bore 168. (While not shown, it should be appreciated that the distal end of spring 422 may seat against a back plate disposed against the base of saw head bore 168.) The opposed end of spring 422 seats in the bore 338 that extends inwardly from the distally directed face of the front inner housing 310. Spring 422 urges the front inner housing 310 and the components attached thereto rearwardly away from the saw head nose 342. The components urged proximally rearwardly with the front inner housing include the oscillating head 70, output shaft 240, oscillating shaft 242 and rear inner housing 268. Spring 422 is selected so that the force imposed by the spring can be overcome by manual force. Further design considerations that contribute to the selection of spring 422 are discussed below.

IV. Blade Coupling Assembly

Figures 33, 34, 35:
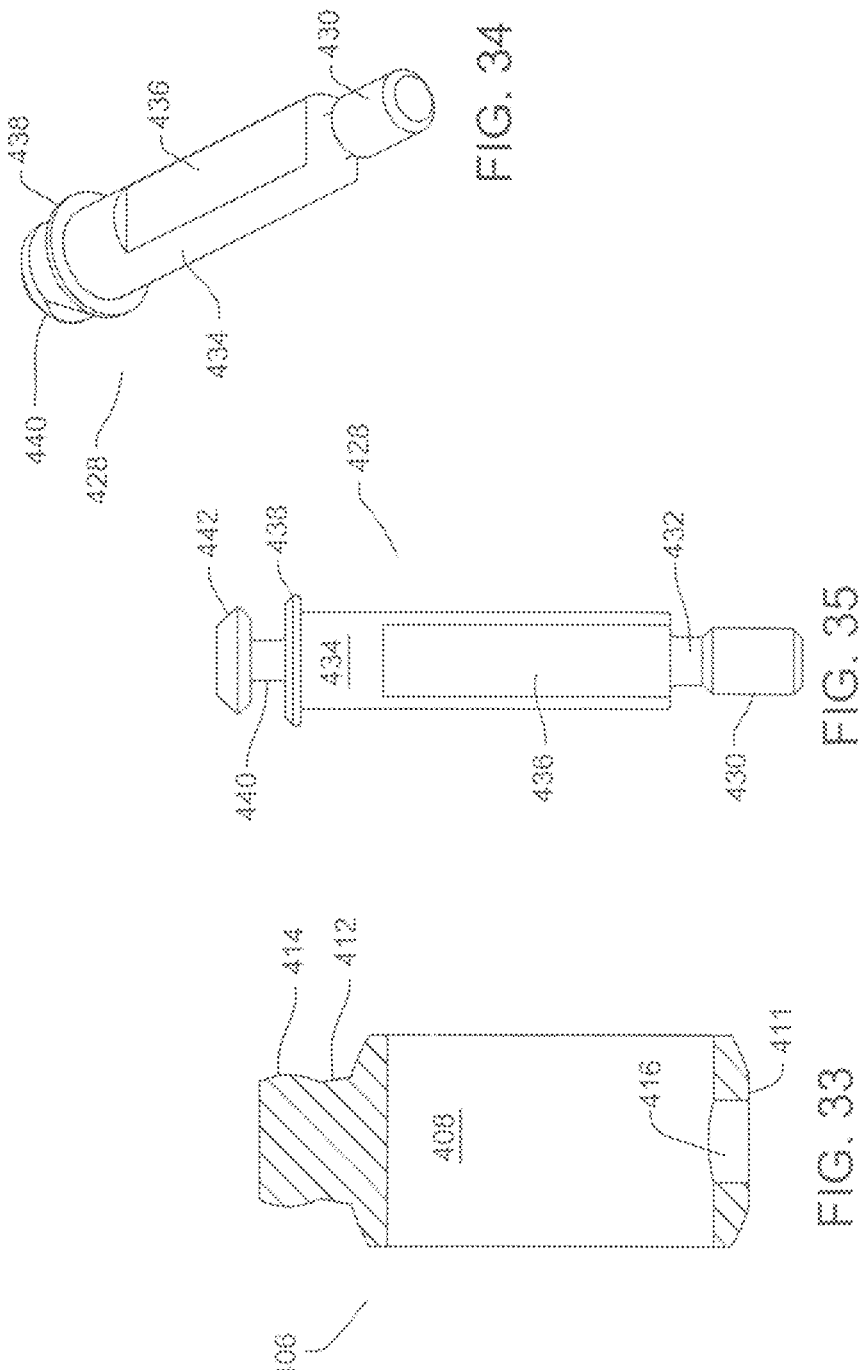
FIG. 33 is a cross sectional view of the wobble ring taken along line 32-32 of FIG. 32.
FIG. 34 is a perspective view of the blade coupling rod.
FIG. 35 is a plan view of the blade coupling rod.

A coupling rod 428 slidably mounted to the saw head 68 releasably holds the blade assembly 52 to the saw. As seen in FIGS. 34 and 35, coupling rod 428 is formed to have a cylindrical, bottom located stem 430. The outer circumferential surface of stem 430 is formed with threading (not illustrated). Above stem 430, rod 428 has a leg 432 with a diameter less than that of the stem. Located immediately above leg 432, rod 428 has a main body 434. The main body 434 generally has a circular cross sectional shape with a diameter greater than that of the stem 430. Coupling rod 428 is further formed so that the rod main body 434 has two diametrically opposed longitudinally extending flats 436 (one shown). Each flat 436 extends upwardly from the lower base of the rod main body 434 to have overall length approximately 65 to 85% the length of the main body.

Above main body 434, coupling rod 428 has a circular collar 438. The collar 438 has an outer diameter greater than that of the main body 434. A neck 440 projects above collar 438. Neck 440 has a diameter less than that of the collar 438. A circular head 442 forms the top most section of the coupling rod 428. The head 440 has a diameter greater than that of neck 440 and slightly less than that of the rod collar 438. In the illustrated version of the invention, the outer perimeter surface of the head 442 located above the neck 440 extends outwardly, the outer perimeter surface of the head that extends downwardly from the top of the head similarly tapers outwardly, (tapered surfaces not identified.)

Coupling rod 428 extends through saw head bores 178 and 166 and into saw head bore 176. The coupling rod 428 also extends through slot 348 formed in the front inner housing nose 342. More specifically, the coupling rod 428 is dimensioned so that the distance between the main body flats 436 is slightly less than the width across slot 348. This allows the coupling rod 428 to move within the slot 348; the limited slot width blocks rotation of the coupling rod.

A spring 446 (seen only in FIG. 4) is disposed around the upper end of the coupling rod main body disposed in saw head bore 178. One end of spring 444 seats in the lip 179 that forms the base of bore 178. The opposed end of the spring 444 presses against the downwardly directed annular surface of the coupling rod collar 438 that surrounds the main body 434.

Figures 36, 37:
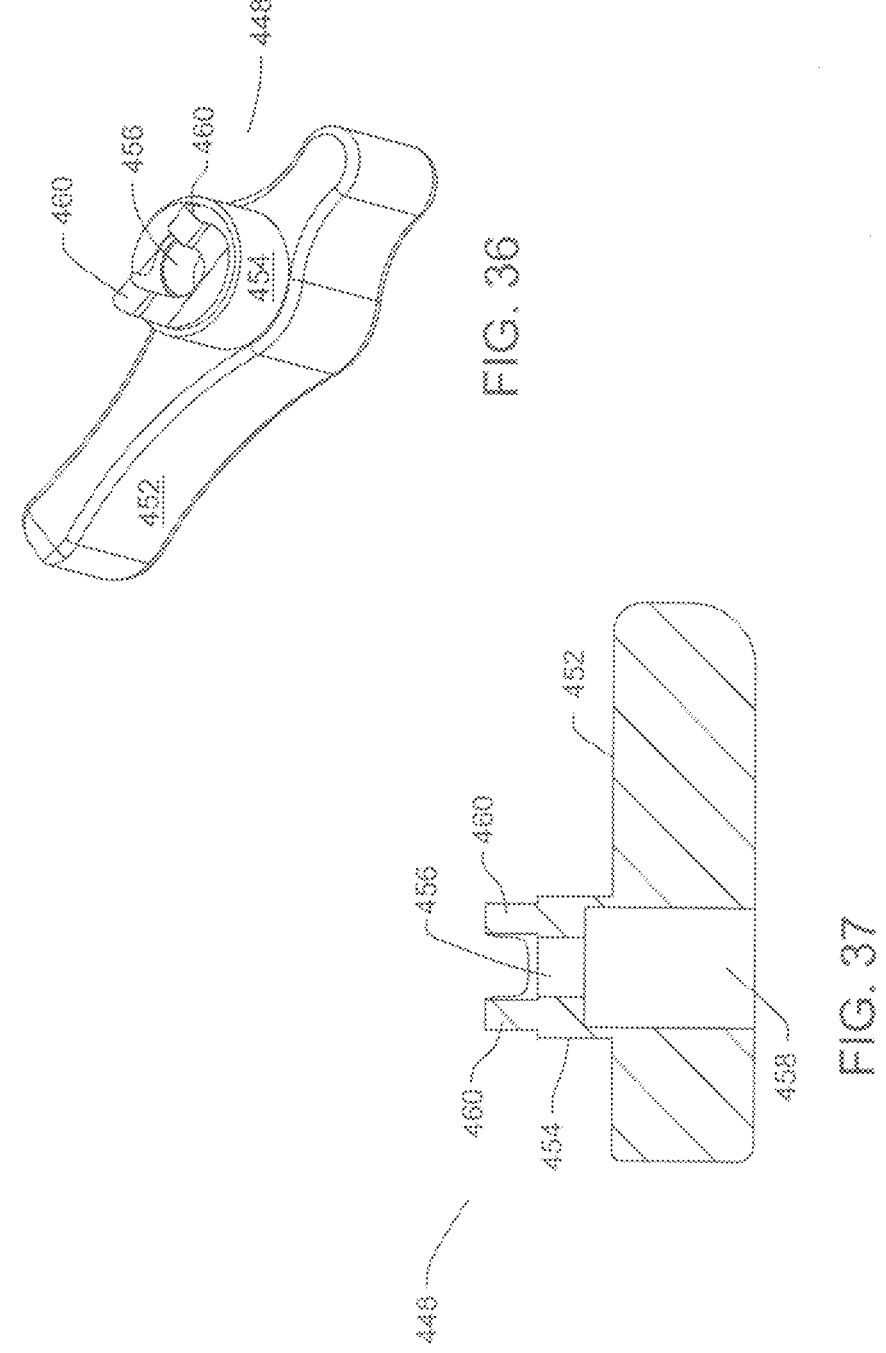
FIG. 36 is a perspective view of the wing nut.
FIG. 37 is a cross sectional view of the wing nut.

A wing nut 448 and a wing nut retainer 450 surround the end of the coupling rod 428 disposed in saw head bore 176. As seen best in FIGS. 36 and 37, wing nut 448 includes an elongated bar 452. Not identified are the concave opposed surfaces on the bar 452 that function as finger/thumb grasping surfaces. A circular boss 454 extends upwardly from one of the side edges of the bar into saw head bore 176. Boss 454 is dimensioned to rotate in saw head bore 176. The wing nut 448 is further formed to have a bore 456 that extends through boss 454 and partially into the underlying section of wing nut bar 452. Bore 456 opens into a coaxially extending bore 458 that extend through to the opposite edge of bar 452. Bore 458 has a larger diameter than bore 456.

Wing nut 448 is further formed so that two diametrically opposed tabs 460 extend upwardly from the exposed annular face of boss 454. Tabs 460 are shaped to have heads with a semi-circular cross sectional shape (tab heads not identified)
.

Figure 38:
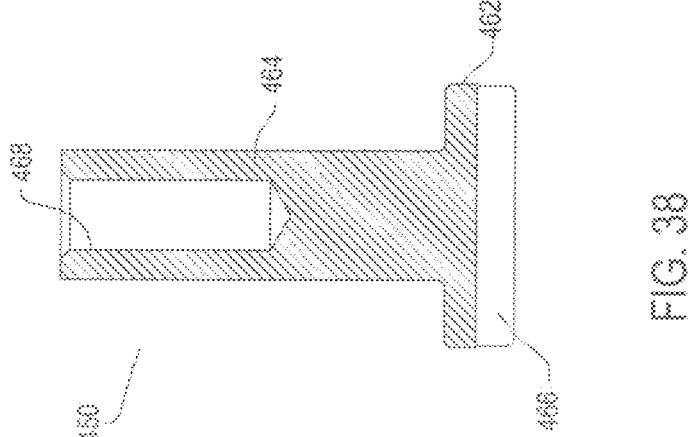
FIG. 38 is a cross sectional view of the wing nut retainer.

The wing nut retainer 450, seen best in cross section in FIG. 38, has a head 462 from which an elongated shaft 464 extends. Head 462 is formed with a diametrically extending slot 466 for receiving the blade of screw driver. The outer surface of shaft 464 is smooth walled and dimensioned to slidably fit in wing nut bore 456. A bore 468 extends inwardly from the free end of the shaft towards head 462. The inner wall of the wing nut retainer that defines bore 468 is provided with threading (not illustrated).

Figure 44:
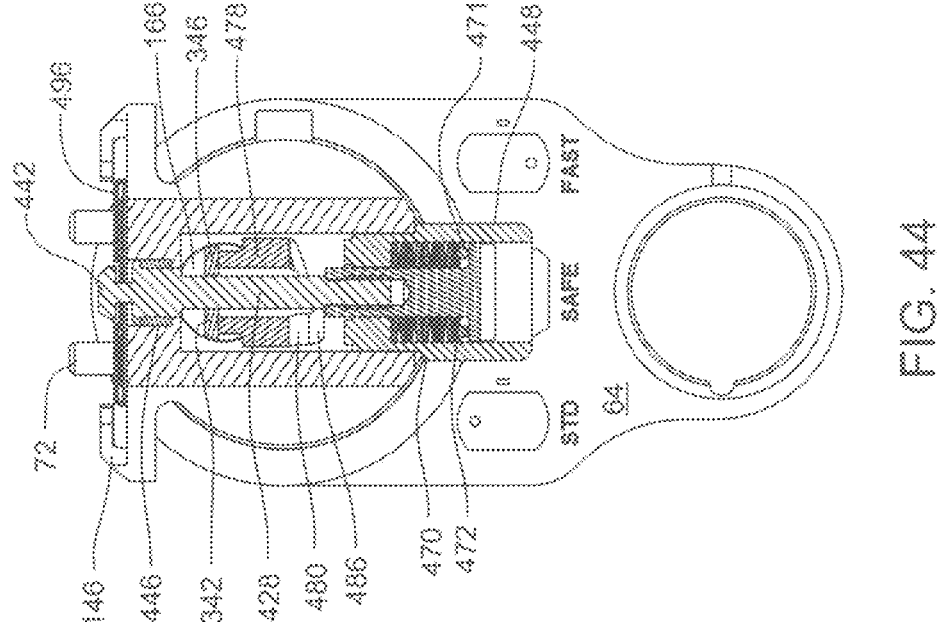
FIG. 44 is a cross sectional view of the blade coupling assembly depicting the position of the components when the assembly in the run, locked, state.

When saw 50 is assembled the coupling rod stem 430 is screw secured in wing nut bore 468 as seen in FIG. 44. As part of the assembly process, a set of Bellville washers 470 are seated in wing nut bore 458 around wing nut retainer shaft 464. The Bellville washers 470 extend between the internal annular surface of the wing nut 448 that defines the base of bore 458 and head 462 of the wing nut retainer 450. In the illustrated version of the invention, ball bearings 471 are disposed between the bottommost Bellville washer 470 and the wing nut retainer head 462. In actuality, the ball bearings 471 are sandwiched between the wing nut retainer head 462 and a ring-shaped race 472 disposed around the bottommost Bellville washer 470. Ball bearings 471 facilitate the rotation of the wing nut 448 and Bellville washers 470 around the wing nut retainer 450.

In some versions of the invention, the ball bearings 471 are disposed between the topmost Bellville washer 470 and the adjacent annular surface of the wing nut 458 that defines bore 468.

A cam 474 is slidably disposed over the coupling rod main body 434 between the front inner housing nose 342 and the wing nut boss 454. As seen in FIGS. 39, 40 and 41, cam 474 has a sleeve shaped main body 476. A head 478, also sleeve shaped, projects above main body 476. Cam head 478 has an outer diameter less than that of the main body 476. Two diametrically opposed, spaced apart teeth 479 extend upwardly from the annular exposed face of the head. The outer surfaces of teeth 479 are flush with and have the same radius of curvature of the head 478. Collectively, cam main body 476 and head 478 define a common constant diameter through bore 477.

Cam 474 is further shaped to define at the base of the main body diametrically opposed cam surfaces. Each cam surface is shaped to have a concave notch 480. The notch 480-defining surfaces define a radius marginally greater that the radius of curvature of wing nut tabs 460. On one side of each notch 480, the cam surface defines a vertical wall 482. On the opposed side of the notch 480, the cam surface is shaped to define a small indentation 484 followed by a downwardly directed sloping wall 486. From the sloping wall 486, each cam surface defines a detent 488. Beyond detent 488, each cam surface defines a notch 490. For each cam surface, notch 490 is, relative to the notch 480, spaced further away from the cam head 478. The portion of the cam surface that defines notch 490 is the end portion of the cam surface. Notches 490, like notches 480, are dimensioned to receive the wing nut tabs 460. The portion of cam main body 476 that forms the vertical wall 482 of a first cam surface defines a similar vertical wall 491 of the second cam surface.

Upon assembly of the saw 50, cam 474 is fit over the coupling rod main body 434. The cam 474 is positioned so that the cam teeth 479 are disposed in nose slot 348 of the front inner housing 310. The seating of the cam teeth in slot 348 blocks rotation of the cam 474. Each wing nut tab 460 seats against a separate one of the cam surfaces. When the coupling assembly is positioned to hold the blade assembly, the run or locked position, each wing nut tab 460 is seated in the notch 490 of the associated cam surface. When the coupling assembly is in the load or unlocked state, in which the blade can be removed and replaced, the wing nut 448 is rotated so nut tabs 460 are positioned in the complementary notches 480.

Figure 42:
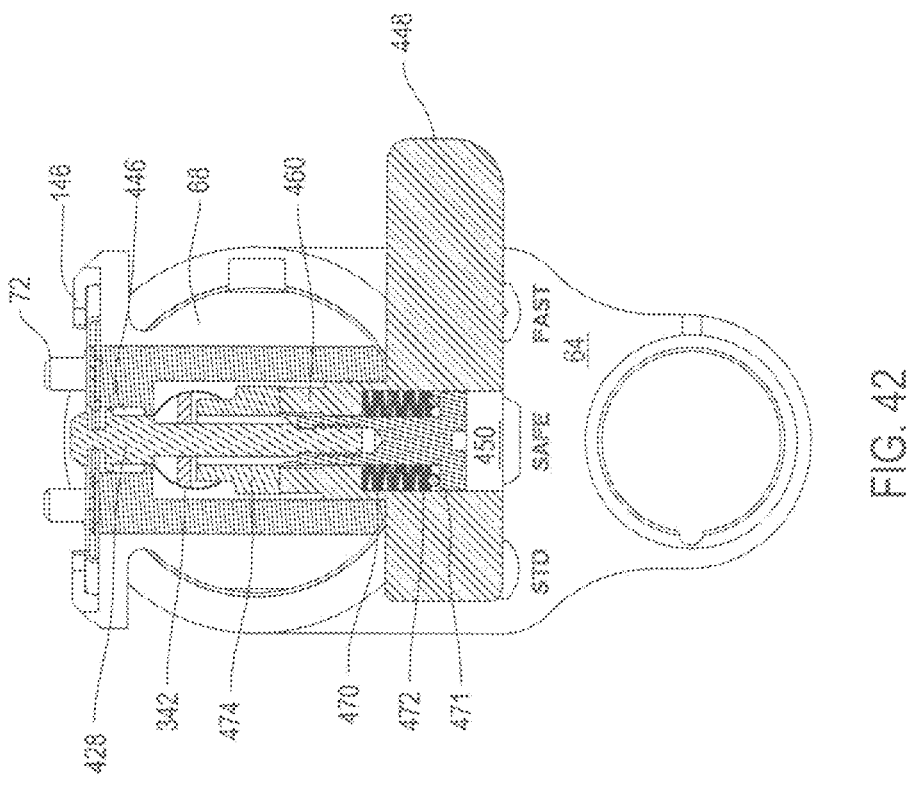
FIG. 42 is a cross sectional view of the blade coupling assembly depicting the position of the components when the assembly is in the blade load, unlocked, state.

As seen in FIG. 42, when the coupling assembly is in the load state, cam 474 is positioned so that the arcuate top faces of the face of the cam head 478 are spaced away from the undersurface of the front inner housing nose 342. Owing to the force placed on the coupling rod 428 by spring 446, the rod is positioned so that the rod head 442 above the saw head top surface 138.

V. Blade Assembly

Figure 43:
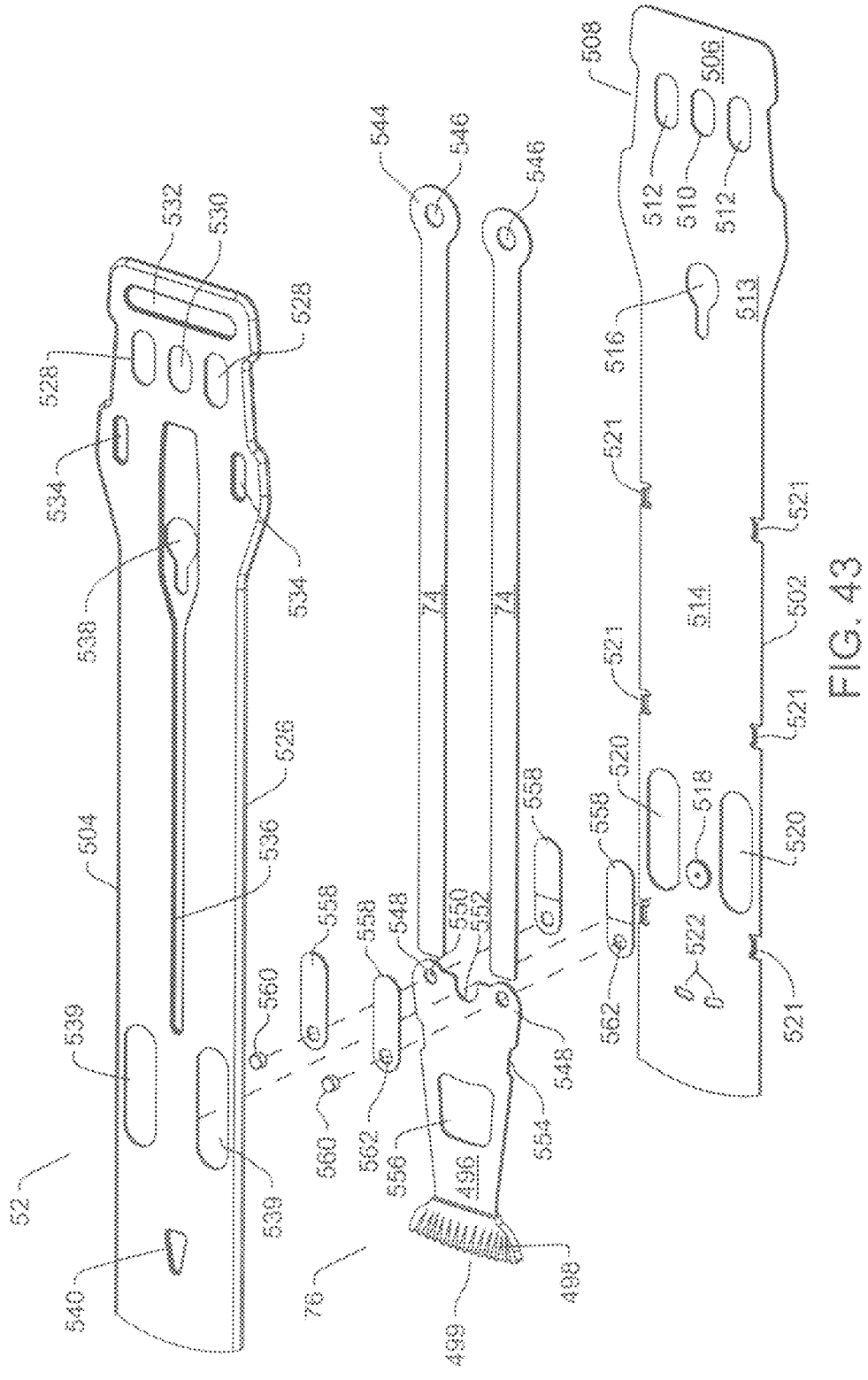
FIG. 43 is an exploded view of the blade assembly.

The construction of the blade assembly 52 of this invention is now explained by reference to FIGS. 1 and 43. Specifically, the blade assembly 52 includes an elongated, flat static bar 494. The proximal end of bar 494 is the component of the blade assembly 52 mounted to the saw head top surface 138. Blade head 76 has a proximal end base 496 that is disposed in the distal end of bar 494. A crown 498, integral with and extending forward from the base 496, is the most distal portion of the blade head 76. The crown 498 projects forward beyond the distal end of the bar 494. The outer distal edge of the crown is formed with the blade teeth 150 (shown schematically) that perform the actual cutting action.

Blade bar 494 is formed from lower and upper plates 502 and 504, respectively. The lower plate 502 has a proximally located base 506, generally in the form of trapezoid, wherein the opposed lateral side edges are symmetric and taper inwardly towards the proximal end edge of the plate 502. The lower bar base 506 is further formed to define opposed notches 508 that extend inwardly from the side edges of the base. Within the section of the base 506 between notches 508, lower plate base 506 is further formed to have an oval shaped opening 510 and two oval shaped openings 512. Opening 510 is centered along the longitudinal axis of the lower plate 502. The openings 512 are located on the opposed sides of and are adjacent to opening 510. The longitudinal axes of openings 512 are parallel with the longitudinal axis of opening 510. Openings 512 are longer than opening 510.

Forward of the base 506, the lower plate 502 is formed to have an intermediate section 513. The side edges of the intermediate section taper inwardly as they extend forward. Plate intermediate section 513 transitions into a constant width blade proximal section 514. The lower plate 502 is further formed so as to define a keyhole-shaped opening 516 that extends from the intermediate section 512 to the distal section 514. Opening 516 is dimensioned so that the coupling rod head 440 can extend into the wide diameter distal portion of the opening. The opening 516 is further shaped so that the narrow portion thereof has a width less than the coupling rod head 442 and greater than that of rod neck 440.

The forward portion of the bar lower plate distal section 514 is formed with a circular, upwardly extending boss 518. On either side of boss 518, lower plate 502 defines an oval-shaped opening 520. Each opening 520 is longitudinally aligned with a separate one of the openings 512. Lower plate 502 is also formed to have three pairs of L-shaped tabs 521. Each tab 521 is located immediately inward of the adjacent longitudinal side of the plate 502. Each tab 521 extends upwardly towards the upper plate 504. The tabs 521 are arranged in pairs such that one tab of each pair is diametrically opposed to the second tab of the pair. A first pair of tabs 521 is located along a line that is slightly proximal to the mid line between opening 516 and openings 520. A second pair of tabs 521 is located slightly proximal to openings 520. The third set of tabs 521 is located distal from openings 521.

Forward of openings 520, the lower plate 502 is formed with two additional openings, discharge ports 522. More particularly, the discharge ports 522 open from a section of the surface of the lower plate that is subtended by the blade head base 496. Each discharge port 522 is approximately in the shape of an oval. Lower plate 502 is further formed so that the discharge ports are centered on a common non-linear longitudinal axis. More particularly this axis is curved. The radius of curvature of this axis is center in which the section of the blade head 46 disposed underneath the ports oscillates. Discharge ports 522 are symmetrically located around the longitudinal axis of the lower plate 502.

The upper plate 504 is shaped to have the same general perimeter profile of the lower plate 502; the description of this profile is not repeated. Upper plate 504 is further formed to have a lip 526 that extends downwardly from the edges of the plate. Collectively, the plates 502 and 504 are dimensioned so that when the upper plate 504 is disposed over the lower plate 502, the upper plate lip 526 extends around the adjacent edges of the lower plate 502. The upper plate 504 is formed so that lip 526 extends around the proximal end of the lower 502 plate and the opposed longitudinally extending side edges of the lower plate 502. Thus, upon assembly, blade bar 494 has a distal end opening between the lower plate 502 and the upper plate 504 (opening not identified).

Upper plate 504 is further formed to have two oval-shaped openings 528. Each opening 528 is identical in shape with and positioned to be aligned directly over one of the lower plate openings 512. An oval shaped opening 530 is also formed in upper plate 504. Opening 530 is identical in shape with and positioned to be aligned directly over lower plate opening 510. Located proximally rearward of openings 528 and 530, the upper plate 504 is further formed to have a downwardly extending gusset 532. Gusset 532 extends laterally across lower plate 504 at a location immediately forward of the proximal end of the plate.

Forward of openings 528 and 530, the upper plate 504 is formed with two gussets 534 and a single gusset 536. Gussets 534 are symmetrically located around the longitudinal axis of the upper plate 504. The gussets 534 are located in the lateral slice section of the upper plate 504 that has greatest width along the plate. Each gusset 534 is located immediately inside the outer perimeter section of the upper plate 504 that transitions into lip 526. The gussets 534 are oval shaped.

Upper plate 504 is formed so that gusset 536 is centered and extends along the longitudinal axis of the plate. Gusset 536 extends from a position slightly proximal to the proximal ends of gussets 534 to a position approximately equal to the proximal ends of below discussed openings 539. The upper plate 504 is shaped so that, adjacent gussets 534, gusset 536 has a relatively wide depth. Forward of the proximal end of the gusset 536, a key hole shaped opening 538 is formed in gusset 536. Opening 538 is identical in size and is positioned to be aligned with lower plate opening 516. Distally forward of opening 538, the upper plate 504 is formed so that gusset 536 has a constant, narrow width.

A pair of additional oval-shaped openings 539 extends through the distal end of the upper plate 504. Each opening 539 has the same shape and is aligned with a complementary underling lower plate opening 520. Forward of openings 520, upper plate 504 is further formed to have a triangularly shaped gusset 540. Gusset 540 is centered on the longitudinal center line of the top plate. Gusset 540 is further positioned to extend from an interior surface of the top plate within the area of the surface that is subtended by the blade head base 496.

Drive rods 74 are disposed between the blade bar lower and upper plates 502 and 504, respectively. Each drive rod 74 is in the form of an elongated flat strip of metal. The drive rods 74 are formed so that, at the proximal end of each rod, there is a circular foot 544. Each foot 544 is formed to have a center located through hole 546. Through holes 546 are dimensioned so that the associated drive rod feet 544 can be fitted over the oscillating head drive pins 72.

While not seen in the Figures, each drive rod 74 may be shaped to form a reinforcing ring around the lower and upper faces of the drive rod foot 544 that defines the hole 546. In some versions of the invention, the basic thickness of the drive rod is approximately 0.015 inches; the reinforcing rings around the hole 546 provide this section with the rod with a thickness of approximately 0.045 inches. In some versions of the invention, the drive rod 74 is so shaped by the selectively grinding of the workpiece from which the drive rod is formed.

Blade head base 496 is dimensioned to oscillate in the gap between lower and upper plates 502 and 504, respectively. In one version of the invention, the blade head base has a thickness approximately 0.001 inches less than the width of the gap between the opposed faces of the lower and upper plates 502 and 504, respectively. Blade head base 496 is shaped so to have a relatively wide proximal end. The proximal end is further formed to have, adjacent each side edge a foot 548. Each foot 548 is arcuately shaped. Diametrically opposed through holes 550 are further formed in blade head base 496 immediately forward of the proximal end. Each through hole 550 is centered on axis around which the adjacent foot 548 is centered. The distal end of the blade head base 496 blade head base is further formed to define a concave semi-circular notch 552. Notch 552 is centered along the longitudinal axis of the blade head 76. More particularly, notch 552 is dimensioned so that when blade 52 is assembled, lower plate boss 518 seats in the notch and blade head 76 is able to pivot around the boss.

Forward of the proximal end, the blade head base 496 has two side edges (not identified) that, extending distally along the blade head, taper inwardly. The side edges define laterally opposed notches 554. Notches 554 function as the void spaces in which the opposed the forwardmost tabs 521 seat when the blade head 76 oscillates. Blade head base 496 is further formed to define a through window 556. Window 556 is positioned so that when the blade 52 is assembled, upper plate gusset 540 extends through the window.

The blade head crown 498 has a thickness greater than that of the associated base 496. More particularly the blade head crown is formed so that the kerf cut by the blade head is sufficiently wide to allow the insertion of the blade bar 494 into the kerf. The exact geometry of the blade head crown 498 is a function of the particular kerf geometry and not otherwise relevant to this invention.

Fingers 558 and pins 560 pivotally hold the blade head 76 to the drive rods 74. A pair of fingers 558 is welded over the opposed distal end surfaces of each drive rod 74. Fingers 558 are welded to each drive rod 74 so that one finger is attached to and extends forward from each surface. Thus, the individual fingers 558 of each pair of fingers overlap. Each finger 558 is formed with a hole 562. Finger holes 562 are formed so that the holes of each pair of fingers overlap in the section of the fingers that extend forward beyond the drive rods 74.

Blade head 76 is fitted to the rest of the blade assembly 52 so that each base foot 548 is seated in the gap between a separate pair of fingers 558. When the blade head 76 is so positioned, each blade head hole 550 aligns with a separate pair of finger holes 562. A pin 560 is fitted in each set of aligned blade head and finger holes 550 and 562, respectively, to hold the blade head to the associated drive rod 74. Each pin 560 is welded or otherwise secured to the opposed finger holes 562 in which the pin is seated.

Once the blade head and drive rod sub-assembly is fabricated, this sub assembly is placed against the inner surface of the upper plate 504. The lower plate 502 is fitted within the upper plate lip 526. As a result of this arrangement, the reinforced rings at the proximal end of the drive rods seat in lower and upper plate openings 512 and 528, respectively. Fingers 558 and pins 560 seat in lower and upper plate openings 520 and 539.

Once the lower bar 502 is fitted over the upper bar, the outer perimeter of the lower bar 502 is spot welded to the adjacent upper bar lip 526. This spot welding generally occurs around the outer perimeter of the lower bar. There is no spot welding adjacent the lower bar tabs 521. Thus, windows (not identified) are formed in the blade bar 494 between each lower bar tab 521 and upper bar lip 526. Once spot welding is complete, projection welding is employed to weld boss 518 to the adjacent inner surface of the upper plate 504. Projection welding is also used to weld gussets 536 and 540 to the adjacent inner surface of the lower plate 502.

VI. Use of Saw

Saw 50 of this invention is prepared for use by first indexing, rotating, the head 68 so that it will be in an angular orientation relative to the longitudinal axis of the saw barrel section 56 that is most ergonomic for the procedure to be performed. To index saw head 68, button 232 is depressed. The depression of button 232 overcomes the force of spring 234 and forces lock link 224 inwardly. The inward movement of the lock link 224 retracts tongue 228 out of the race opening 210 in which the tongue is seated. As a result of this displacement, saw head 68 is freely rotatable relative to the motor housing 80. It should be appreciated that when the indexing lock assembly is in this state, the release state, the free end of lock link tongue 228 is disposed within saw head opening 130. This prevents the lock link 224 from laterally shifting position.

Once the saw head 68 is in the selected angular orientation, the manual force imposed on the lock link 224 through button 232 is released. Spring 234 pushes the lock link 224 laterally outwardly relative to the longitudinal axis of the saw head 68. Consequently, the force imposed by spring 234 causes the lock link tongue 228 to extend through the saw head opening 130 and seat in the adjacent race opening 210. This rescating of the lock link tongue 228 locks the saw head 68 in the new fixed angular orientation around the center axis of the motor housing 80.

Assuming that the blade coupling assembly is in the load state, a blade assembly 52 is then coupled to the saw head 68. This process starts with the position of the blade assembly 52 over the saw head top surface top surface 138 so that drive head pins 72 seat in the proximal located holes 546 formed in the drive rods 74 and the neck of the coupling rod neck 440 seats in the wide diameter section of blade bar openings 516 and 536. At this time, the proximal end of the blade bar 494 is disposed over the saw head brackets 146 and 148.

Blade assembly 52 is manually pulled distally forward. This force is transferred through the oscillating head drive head pins 72 to the other components internal to the saw head 68, namely, the rear and front inner housings 268 and 310, respectively, and the components attached to these housings. This force overcomes the force spring 422 imposes on the front housing 310 that holds it in the proximal position. Blade assembly 52 is pulled forward, until the proximal end edge surfaces of the blade bar 494 is forward of the saw head brackets 146 and 148. Once the blade assembly 52 is in this position the proximal end of the blade bar 494 is pushed down against the saw head top surface 138. The manual forward pulling force on the blade assembly 52 is released. Once the manual force is released, spring 422 pushes front inner housing 310 and components attached thereto rearwardly. These components include the pins 72 integral with oscillating head 70. This rearward movement of the drive pins 72 causes a like displacement of the blade assembly 52. This proximal movement of the blade assembly draws the proximal end longitudinal side surfaces of the blade bar 496 against the saw head brackets 146 and 148. The rearward displacement of the blade assembly 52 also causes the blade bar 496 to move so that the bar portion that defines the narrow width portions of the bar openings 516 and 536 seat around the coupling rod neck 440.

The blade coupling assembly is then actuated to releasably clamp, lock, the blade assembly 52 to the saw head 68. This action is performed by rotating the wing nut 448 so that the nut bar 452 is longitudinally parallel with the longitudinal axis of the saw head 68. As a consequence of this motion, wing nut boss 454 and tabs 460 rotate around both the coupling rod 428 and the cam 474. More particularly, tabs 460 are initially disposed in the individual notches 480 defined by the cam 474. The tabs 460 move against the cam sloping walls 486. This action urges cam 474 upward relative to the saw head 68. As a consequence of being forced upwardly, the upwardly directed exposed arcuate faces of the cam head 478 are pushed against the adjacent downwardly directed surface of the inner housing nose 342 as seen in FIG. 44. The continued upward motion of the cam 474 causes the cam to flex the inner housing nose upwardly. Eventually this action causes the opposed nose side edges 346 to press against the adjacent inner circular wall of the saw head that defines saw head bore 166. This action locks the front inner housing 310 and components attached thereto against rotation relative to the longitudinal axis of the saw head 68.

The abutment of the front inner housing nose 342 against an inner wall of the saw housing 68 also prevents further upwardly movement of the cam 474. Wing nut tabs 460 continue to rotate along the cam sloping wall 486. As a result of this continued movement of the wing nut 448, the wing nut is forced downwardly, away from the front inner housing nose 342. The downward movement of wing nut 448 results in a like downward displacement of the Bellville washers 470 located internal to the wing nut. The movement of the Bellville washers 470 causes the washers to increase the force they impose of on the wing nut retainer 450. This force is greater than the opposite force spring 446 imposes on the coupling rod-wing nut retainer sub-assembly. Thus, the downward movement of the Bellville washers 470 urges the coupling rod and wing nut retaining sub-assembly in a like downward motion. The downward movement of coupling rod 428 results in the pressing of the undersurface of the rod head 442 against the adjacent exposed face of the blade bar upper plate that defines opening 538. Once the rotation of the wing nut 448 results in wing nut tabs 460 seating in notches 490, the coupling assembly is locked in the run state, no further force is needed to hold the wing nut so that the coupling assembly holds the blade assembly 52 to the saw 50.

Once blade assembly 52 is in the locked in position, saw 50 is ready for use. The depression of the trigger 66 results in the actuation of the motor 66. The rotational moment of the motor rotor 68 is transferred through the drive coupler 296 to the output shaft 240. Due to the shape of the drive coupler 296, the output shaft 240 remains rotatably connected to the motor rotor 68 as the output shaft is pulled forward in order to attach the blade assembly 52.

The rotation of the output shaft 240 results in the off center rotation of the shaft head 256 and nose 264, respectively. The coupling of the wobble ring 406 to the oscillating shaft 242 prevents the wobble ring from rotating. Consequently, as a result of the rotation of shaft head 256, the wobble ring head 414 oscillates back and forth in an arcuate path of travel. The motion is captured by the oscillating shaft center section 352. Oscillating shaft 242 is thus forced into an oscillating motion. The oscillating motion of shaft 242 is output by the oscillating head pins 72 as reciprocal motion.

The reciprocal motion of the oscillating head pins 72 is transferred to the blade assembly drive rods 74. The reciprocation of the drive rods 74, in turn, causes the blade head 76 to pivot about boss 518. The pivotal movement of the blade head 76 enables the blade head to cut the tissue to which the head is applied.

During the course of using saw 50 and blade assembly 52 of this invention. Small bits of severed tissue may enter the open distal end of the blade bar 496. This debris may enter the small spaces between the face of the blade head base 496 and the adjacent inner surface of the lower or upper bar 502 or 504, respectively. In the event tissue becomes entrained in this space, it will migrate into the moving space of window 556. From window 556, the debris is discharged out of the blade bar through the lower plate discharge ports 522.

Saw 50 and saw blade 52 of this invention are constructed so that only component that oscillates is the distally located blade head 76. Thus, the system of this invention has the benefits provided by other sagittal saw assemblies where only a relatively short length blade head located distally forward of the saw head 68 pivots.

The saw 50 of this invention is further constructed so that the saw head 68 is able to index relative to the saw housing 54. The indexing assembly is constructed so that a first biasing member, wave spring 181, holds the saw head 68 and components internal to the saw head to the motor housing 80 while a second biasing member, spring 234, holds the saw head in a locked index state. Consequently, when surgical personnel reset the index position of the saw head 68 only a first minor force, the force exerted by spring 234, needs to be exerted in order to unlock the saw head from the lock state so it can be rotated. Surgical personnel thus do not have to apply significant force, in order to overcome a single biasing member that both holds the saw head in fixed longitudinal position and prevents head rotation.

The coupling assembly of the saw of this invention to make it relatively simple to both remove and attach new blades to the saw head 68. It should further be appreciated that the coupling assembly is keyless. One does not require an additional tool separate from the saw that needs to be sterilized and accounted for when in the operating room.

It should be appreciated that gussets 536 and 550, since they extend between the lower and upper plates 502 and 504 respectively, provide structural strength to the blade bar 496.

This strength prevents the blade bar from flexing when exposed to unbalanced top and bottom loading.

Still another feature of the blade assembly of this invention is the discharge ports 522 located in the distal section of the blade bar 494, the section in which the blade head is seated. Discharge ports 522 provide a discharge path through which cut tissue and other debris entrained in the blade bar 494 are ejected from the blade 52. This prevents this material from being trapped in the blade where it can impede the movement of the blade head and/or stress the components of the blade assembly to a level at which there is the potential for component failure.

VII. Alternative Embodiments

It should be recognized that the above description is directed to a specific version of the saw 50 and blade assembly 52 of this invention. Other versions of the invention may have features and benefits different from what has been described.

Figure 45:
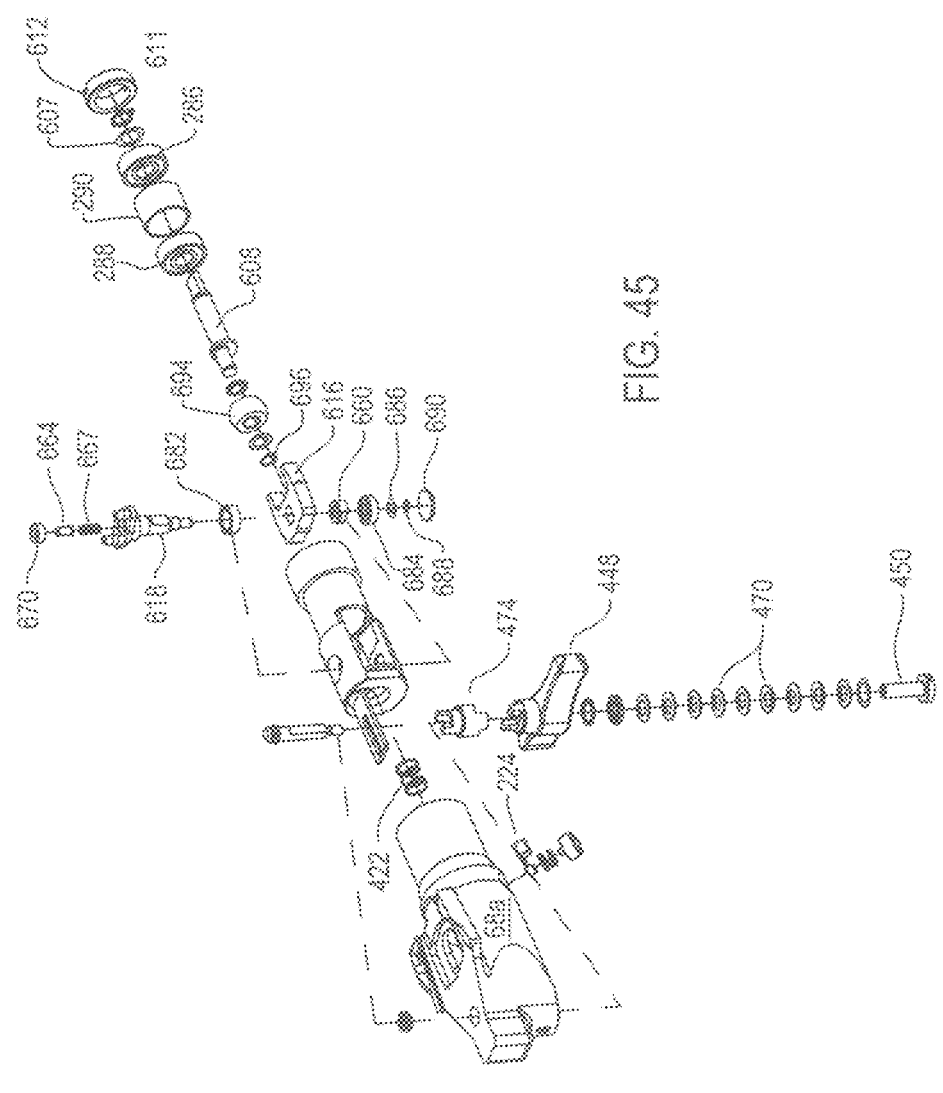
FIG. 45 is an exploded view of an alternative saw head assembly of this invention.
Figure 46:
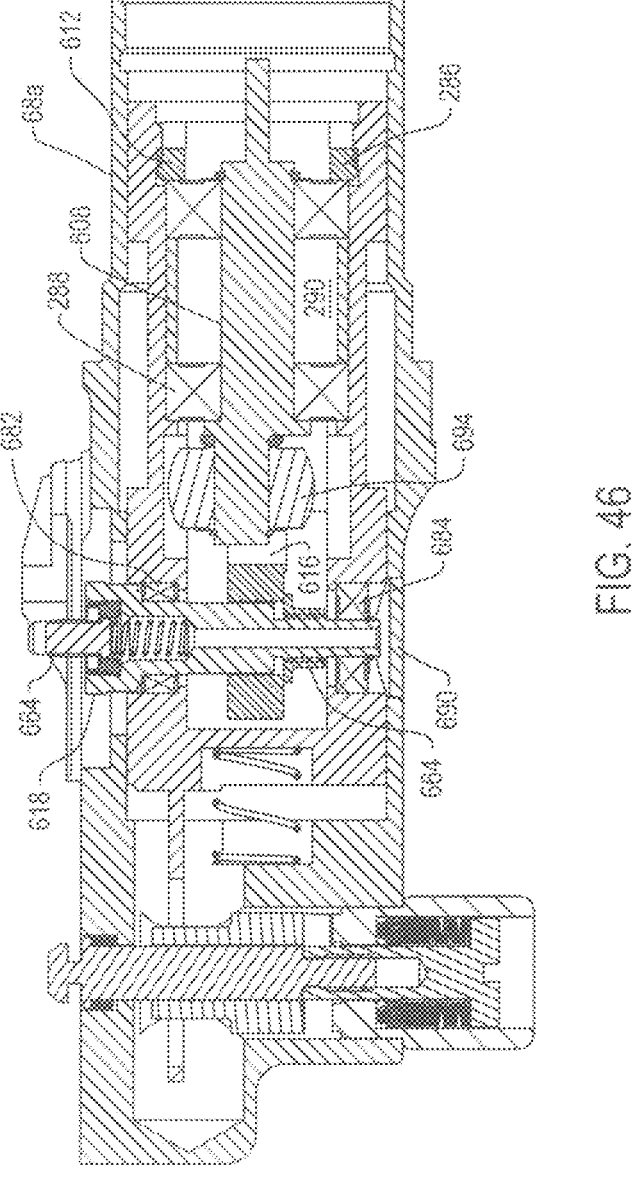
FIG. 46 is a cross sectional view of the saw head assembly of claim 45.

FIGS. 45 and 46 are overviews of an alternative saw head assembly of this invention. This saw head assembly includes a saw head 68a in which a single inner housing 570 is rotatably mounted.

Figure 47:
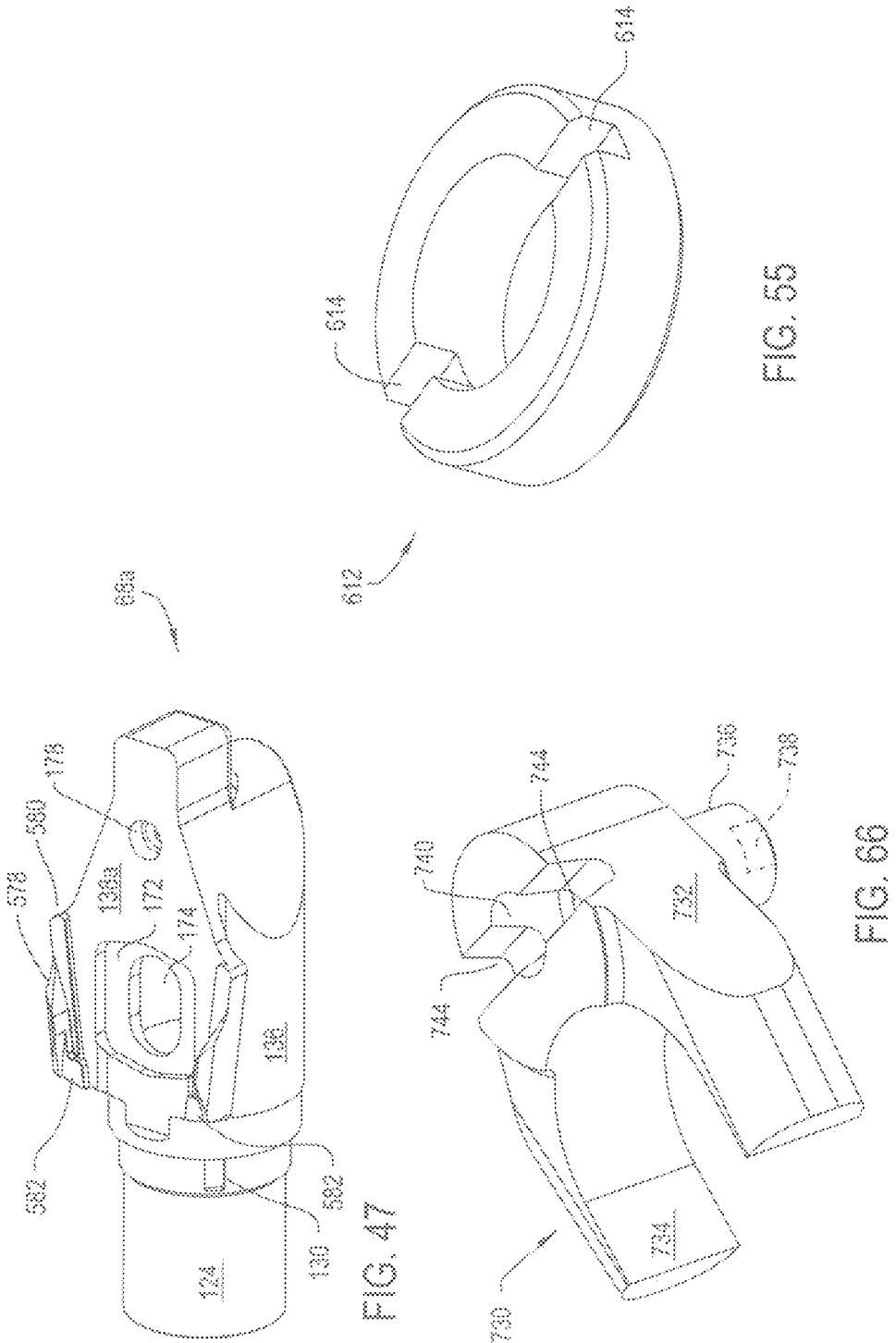
FIG. 47 is a perspective view of the saw head of the alternative saw head assembly.
Figures 48, 49:
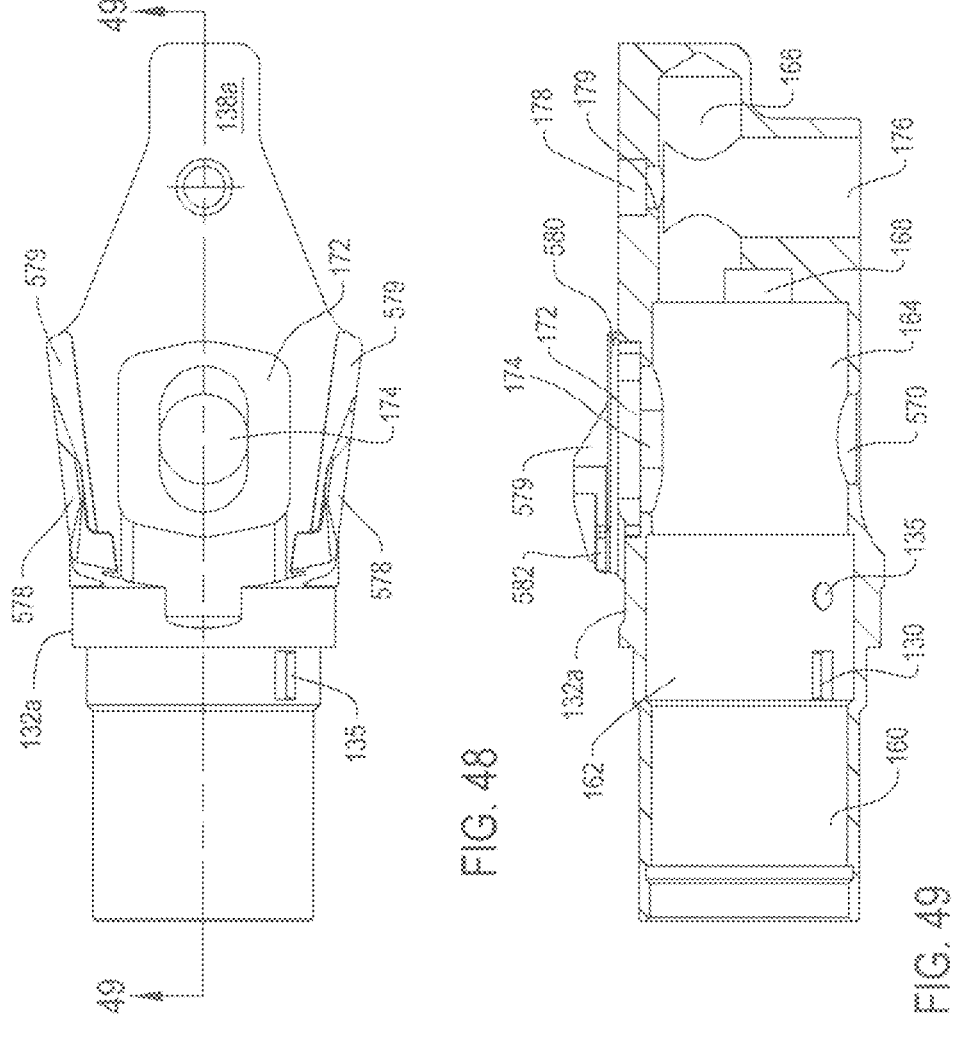
FIG. 48 is a top view of the alternative saw head.
FIG. 49 is a cross sectional view of the alternative saw head taken along line 49-49 of FIG. 48.

Turning to FIGS. 47, 48 and 49, it can be seen that saw head 68a has the same basic proximal end section 124, tapered section 126, first intermediate section 128 and distal end section 136 of the first described saw head 68, (FIGS. 7 and 8). Saw head 68a also has the previously described openings 130, 135, 172 and 174 and bores 133, 160, 162, 164, 166, 168, 176 and 178 of saw head 68. Saw head 68a has a distal end portion 136a that is slightly different than the similar portion 136 of saw head 68. Specifically, distal end portion 136a is formed with an opening 576 into bore 164. Opening 576 is concentric with opening 174.

Saw head 68a has a top surface 138a with the same basic geometric profile of top surface 138 of saw head 68. Only a single pair of brackets 578 extend upwardly from the top of the saw head 68a to partially extend over the proximal end of the top surface 138a. Each bracket 578 has a wall 579 that extends upwardly from the associated side of the saw head 68a that runs along the outwardly tapering proximal side edge of the top surface 138a. A rectangular step 580 extends along the corner where the saw head top surface 138a and the bracket side wall 579 meet. A tab 582 extends perpendicularly inwardly from the top of the side wall 579. Each tab 582 extends both over the underlying step 580 and a short distance over the saw head top surface 138a. Brackets 578 are further formed so that tabs 582 only subtend portions of the top surface 138a immediately forward of the proximal end of the top surface.

Figures 50, 51, 52:
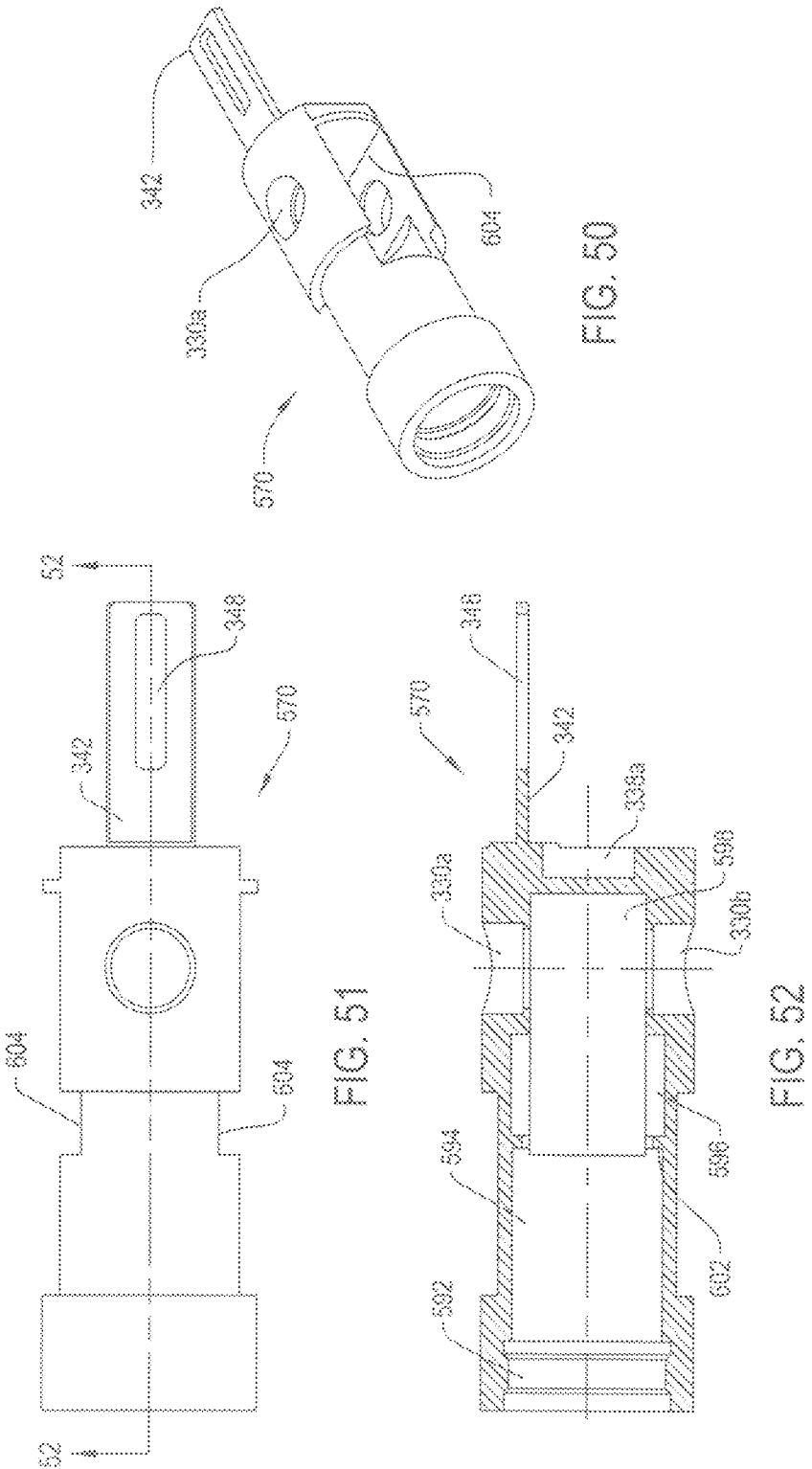
FIG. 50 is a perspective view of the inner housing of the alternative saw head.
FIG. 51 is a top view of the alternative inner housing.
FIG. 52 is a cross sectional view of the inner housing taken along line 52-52 of FIG. 51.

Inner housing 570 substitutes for the combined front and rear inner housings of the first embodiment of the invention. The inner housing 570, best seen in FIGS. 50, 51 and 52 is formed with first, second and third bores 592, 594 and 596, respectively, that extend coaxially forward from the proximal end of the housing. Bore 592 forms the proximal end opening into the inner housing. Bore 594, which is immediately forward of bore 592, has a diameter slightly less than that of bore 592. It should further be appreciated that the section of the inner wall of the inner housing 570 that defines the distal end of bore 592 is formed with threading (not identified). Also not identified is the cut out present for manufacturing purposes between the threaded distal end of the first bore 592 and the second bore 594.

Third bore 596 is located forward of second bore 594. The third bore 596 has a diameter slightly greater than that of second bore 594. The inner housing 570 is further formed to define an annular, inwardly extending lip 602. Lip 602 is located between the second and third bores 594 and 596, respectively, so as to define the distal end base of the second bore 594. Inner housing 570 is further formed to have side window 604. Window 604 extends laterally through the inner housing. Internal to the inner housing, side window 604 is defined by two planar parallel spaced apart interior walls. The side window is primarily located forward of third bore 596. However, it should be further appreciated that side window 604 also intersects both the whole of third bore 596, the void space defined by lip 602 and the distal portion of the second bore 594 adjacent the lip.

Inner housing 570 is further formed to have top and bottom openings 330a and 332a, respectively into the third bore 596. An annular lip 599 extends around the base of top opening 330a. An annular lip 601 extends around the base of bottom opening 332a. A nose 342a extends forward from the front face of the inner housing 570. A bore 338a extends inwardly proximal from the housing front face. The inner housing 570 is also shaped to have two longitudinally extending diametrically opposed side windows 604 (one shown).

An output shaft 608 is rotatably disposed inside inner housing 570. Output shaft 608, now described by reference to FIGS. 53 and 54, has a stem 244a, a main section 246a and a collar 252a that correspond to these features of the first described output shaft 240. Immediately forward of the proximal end of shaft main section 246a, an annular groove 609 is present in this portion of the shaft 608. Forward of the collar 252a, shaft 608 has a cylindrical head 610. Head 610 extends forward from the collar 252a along an axis parallel to and laterally offset from the common longitudinal axis of the shaft stem 244a, main section 246a and collar 252a. Shaft 608 is further formed so there is an annular groove 611 in the head 610 immediately proximal to the distal end of the head.

Bearing assemblies 286 and 288 rotatably hold output shaft 608 in the inner housing second bore 594. The inner races of both bearing assemblies 286 and 288 are disposed over the shaft main section 246a. The forward facing round face of bearing assembly 288 seats against shaft collar 252a. The distally directed outer face of the outer race of bearing assembly 288 seats against inner housing interior lip 602. The distally directed outer face of the inner race of bearing assembly 288 seats against the radially outwardly directed proximally facing face of the shaft collar 252a.

A bearing retainer 612 holds the proximal-located bearing assembly 286 in the inner housing first bore 592. Best seen in FIG. 55, bearing retainer 612 is generally ring shaped. The outer circumferential wall of the bearing retainer 612 is provided with threading, (not illustrated). Diametrically opposed, longitudinally aligned notches 614 extend inwardly from the proximally directed annular face of the bearing retainer 612. Notches 614 are dimensioned to receive a tool (not illustrated) used to insert and remove the bearing retainer.

When this blade drive assembly is put together, the bearing retainer 612 is screw fitted into the threaded section of inner housing first bore 592. The retainer 612 abuts the proximally directed annular face of the outer race of bearing assembly 286. A C-shaped snap ring 609 seats in shaft groove 611. Snap ring 611 is disposed against the proximally directed face of the inner race of bearing assembly 286 to limit forward movement of the output shaft 608. A washer 607 is disposed between bearing assembly 286 and snap ring 611.

The rotational movement of output shaft 608 is output as oscillating motion by an oscillating yoke 616 and oscillating head 618 coaxially mounted to the inner housing 570 to rotate. The oscillating yoke 616, best seen in FIGS. 55 and 56, is formed from a single piece of metal shaped to have a main body 620 that is generally trapezoidal in shape. At the distal end, main body 620 is of short length; at the proximal end, longer in length. Opposed fingers 622 extend proximally rearwardly from the opposed proximal end corners of the main body 620.

Yoke 616 is further formed to have a bore 624 that extends laterally through the main body 620, top to bottom. Bore 624 has a generally oval shape. While the cross sectional geometry of bore 624 is constant, the bore does taper inwardly. More specifically the planar surfaces that define the sides of the bore 624 taper inwardly. At the top of the main body 620, the distance between these surfaces is wider than at that the bottom of the main body. The curved walls that define the opposed ends of the bore have a constant radius of curvature along the length of the bore.

The oscillating head 618, now described by reference to FIGS. 58 and 59, is seated in yoke bore 624. Starting at the lower end, oscillating head 618 has a cylindrically shaped foot 628. Immediately above the base of the foot 628, the foot is formed with groove 629 that extends circumferentially around the foot. Located above foot 628, the oscillating head 618 has a cylindrical leg 630. Leg 630 has a larger outer diameter than foot 628. Threading is formed around the outer circumference of leg 630 (threading not illustrated.) A trunk 632 extends above leg 630. Trunk 632 has a cylindrical structure. While the trunk 632 is generally circular in shape, it is formed so as to have two diametrically opposed flats 634. The flats 634 extend upwardly from the bottom of the trunk 632 at approximately 90% of the length of the trunk. The flats 634 taper outwardly relative to the longitudinal axis of the head 620 when moving from bottom to top along the head.

Above the trunk 632, oscillating head 620 is formed to have a collar 636. The collar 636 is cylindrical in shape and has a diameter slightly greater than that of the adjacent portion of the trunk 632. Above collar 636 oscillating head 620 has a neck 640. The neck 640 is cylindrical in shape and has a diameter greater than that of the collar 636. A small step 638 is located around and below the base of the neck 640. Step 638 thus surrounds the top of the collar 636.

A top plate 642 similar to top plate 370 (FIG. 28) projects outwardly beyond oscillating head neck 640. Drive pins 72 extend upwardly from holes 644 in the opposed ends of the drive plate. In FIG. 58 a braze ring 646 is located in the base of each hole 644. The braze rings 646 become dispersed in the brazing process so as to secure the drive pins 72 to the oscillating head 618.

A bore having a plurality of different sections extends axially through the oscillating head 620 from the foot 628 to the neck 640. The bore has a first section 648 that extends through the foot 628, leg 630 and trunk 632. A second section 652 has a wider diameter than the first section 648 extends through the collar 636 and into the base of the head. Between the first and second bore sections 648 and 652, respectively, there is a tapered transition section 650. Above the second section 652, the bore has a third section 654 that opens out into the top plate 642. The top of the oscillating head collar 636 that defines the bore third section 654 is provided with threading (not illustrated). Not identified is the tapered transition section between the second and third sections 652 and 654, respectively.

When saw head 68*a* is assembled, the oscillating head 618 is fitted in the yoke bore 624 so that trunk 632 is seated in the yoke bore. A nut 660, seen best in FIGS. 60 and 60*a*, is threaded over the oscillating head leg 630 to hold the head 618 in the yoke bore 624. Nut 660 while generally circular, is shaped to have a washer shaped head 661 from which a base 662 extends. While base 662 is generally circular in shape, it is formed with two opposed flats 663 (one shown). The flats 663 receive a tool for fastening and loosening the nut 660.

When the saw head is assembled, the nut head 661 abuts the yoke 618. Nut 660 thus presses the yoke 618 upwardly so that the inner walls that define the tapered sides of bore 624 press against the tapered head flats 634. A torque wrench is used in this process to ensure that the yoke 616 is not over compressed around the oscillating head 618.

Owing to the compression of the yoke 616 around the oscillating head 618, these components, for practical purposes, are a single unit. Thus, when the saw is actuated the oscillating head does not move relative to the yoke. Also, since a torque wrench is used to fit nut 660 in place, the amount of outward expansion stress to which the material defining the yoke bore 624 is exposed can be set. Collectively, these features substantially reduce the likelihood of the material forming the yoke 616 will crack and/or suffer stress failure.

Figures 61, 62, 73:
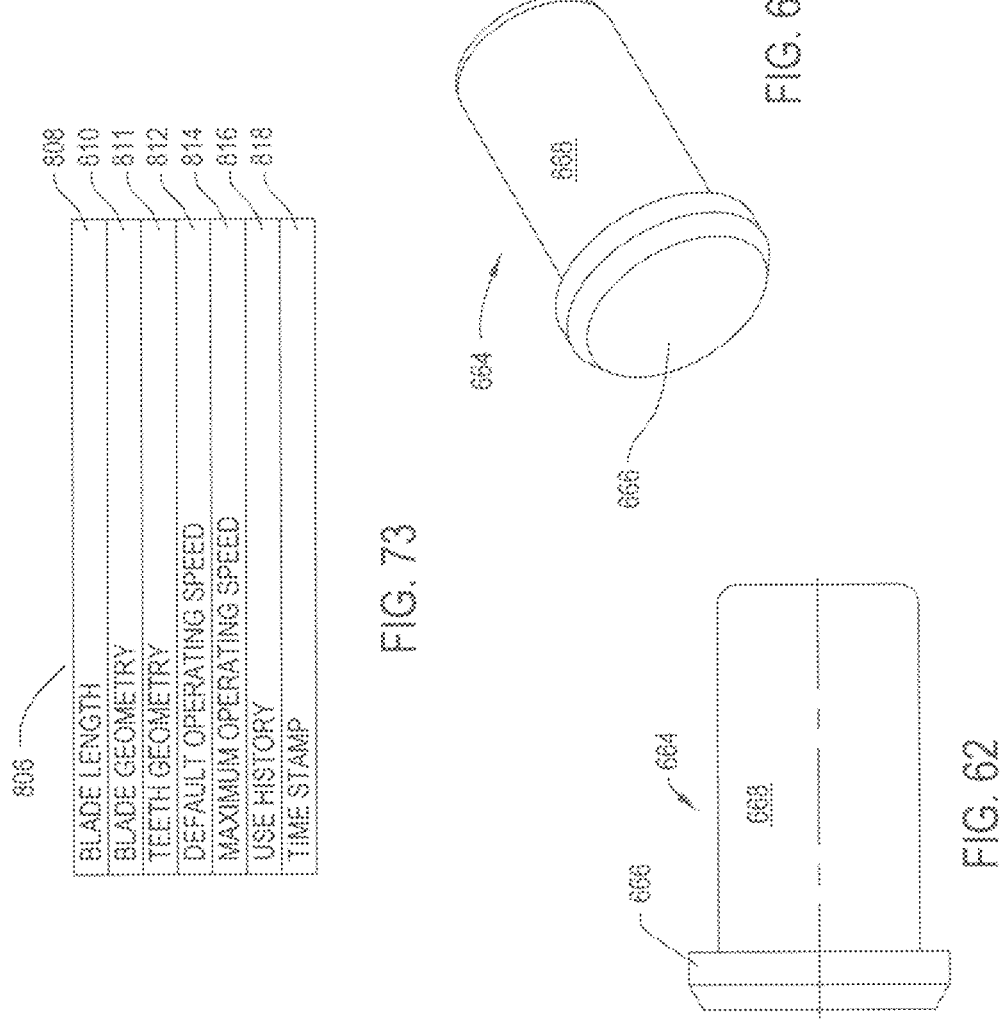
FIG. 61 is a perspective view of the plunger.
FIG. 62 is a side view of the plunger.
FIG. 73 is a block diagram representative of the memory of the RFID and, more particularly, the types of data stored in the memory.

A spring biased plunger 664, described with respect to FIGS. 61 and 62, is disposed in the oscillating head 620. The plunger 664 has a disk shaped base 666. A cylindrical stem 668 extends upwardly from base 666.

Plunger 664, when in the retracted state, is disposed in oscillating head second bore section 652. A washer shaped plunger retainer 670, shown in FIGS. 63 and 64, holds the plunger 664 in the oscillating head bore. While not shown it should be understood that the outer cylindrical surface of the plunger retainer is provided with threading. This threading facilitates the screw securement of the plunger retainer to the complementary threading around the oscillating head bore third section 654. The plunger retainer 670 has a center through hole 672 through which the plunger stem 668 extends. A counterbore 674 opens into through bore 672 from the concealed face of the plunger retainer 670. Two opposed closed end bores 676 are located on opposed sides of the outer face of the plunger retainer 670. Bores 676 receive a fastening tool that facilitates the insertion and removal of the plunger retainer 670 from the oscillating head bore third section 654.

When saw head 68*a* is assembled, a spring 677 is disposed in the oscillating head bore second section 652. Spring 677 extends between the static surface of the oscillating head that defines the bore tapered section 650 and the plunger base 666. The spring 677 thus pushes the plunger outwardly so the plunger stem 668, if unopposed, projects above the oscillating head top plate 642. Thus, during removal of the saw blade 702 (FIG. 65) plunger 664 exerts an upward force on the blade bar to force the bar away from the saw head 68*a*.

When the plunger 664 is so extended the plunger head 668 seats against the annular step between the bore 672 and counterbore 674 internal to the retainer 670. Thus, retainer 670 holds the plunger to the oscillating head 618.

Oscillating head 618 extends through the inner housing top opening 330*a*, window 604 and the bottom opening 332*a*. In the top opening 330*a*, a bearing assembly 682 rotatably holds the oscillating head 618 in place. More particularly, bearing assembly 682 extends between the inner cylindrical wall of the inner housing 570 that defines opening 330*a* and oscillating head collar 636. The bottom surface of the outer race of the bearing assembly 682 rests on the annular lip 599 that defines the base of opening 330*a*.

Foot 628 is the portion of oscillating head 618 that is disposed in inner housing bottom opening 332*a*. A bearing assembly 684 rotatably holds the oscillating head foot 628 to the inner housing. More particularly, bearing assembly 684 extends between the internal cylindrical wall of the inner housing 570 that defines the bottom opening 332*a* and the oscillating head foot 628. The upwardly directed face of the outer race of the bearing assembly 684 presses against lip 601 that defines the base of the bottom opening 332*a*. A snap ring 688 disposed around the end of the foot 628 holds the bearing assembly 684 to the oscillating head. Snap ring 688 is seated in annular groove 629 formed in the foot 628. A washer 686 is disposed between the inner race of bearing assembly 684 and snap ring 688.

For purposes of assembly and disassembly, oscillating head 618 is accessible through saw head opening 576. A plug 690 removably covers opening 576.

A bearing assembly 694 is disposed over the head 610 of the output shaft 608. A snap ring 696 seated in shaft groove 611 holds the bearing assembly 694 to the shaft head 610. It will further be appreciated that bearing assembly 694 is formed to have an outer race with a cross sectional profile equal to that of a center slice through a sphere. A spacer (not identified) is located on either side of the inner race of bearing assembly 694.

Bearing assembly 694 is positioned so as to be disposed within the opposed fingers 622 of oscillating yoke 616. More particularly, the outer race of the bearing assembly 694 bears against the opposed planar surfaces of the yoke fingers 622. Thus, the rotation of the output shaft 608 is transferred by the bearing assembly 694 into a motion that causes yoke 618 and, by extension, oscillating head 618 to oscillate.

Figure 65:
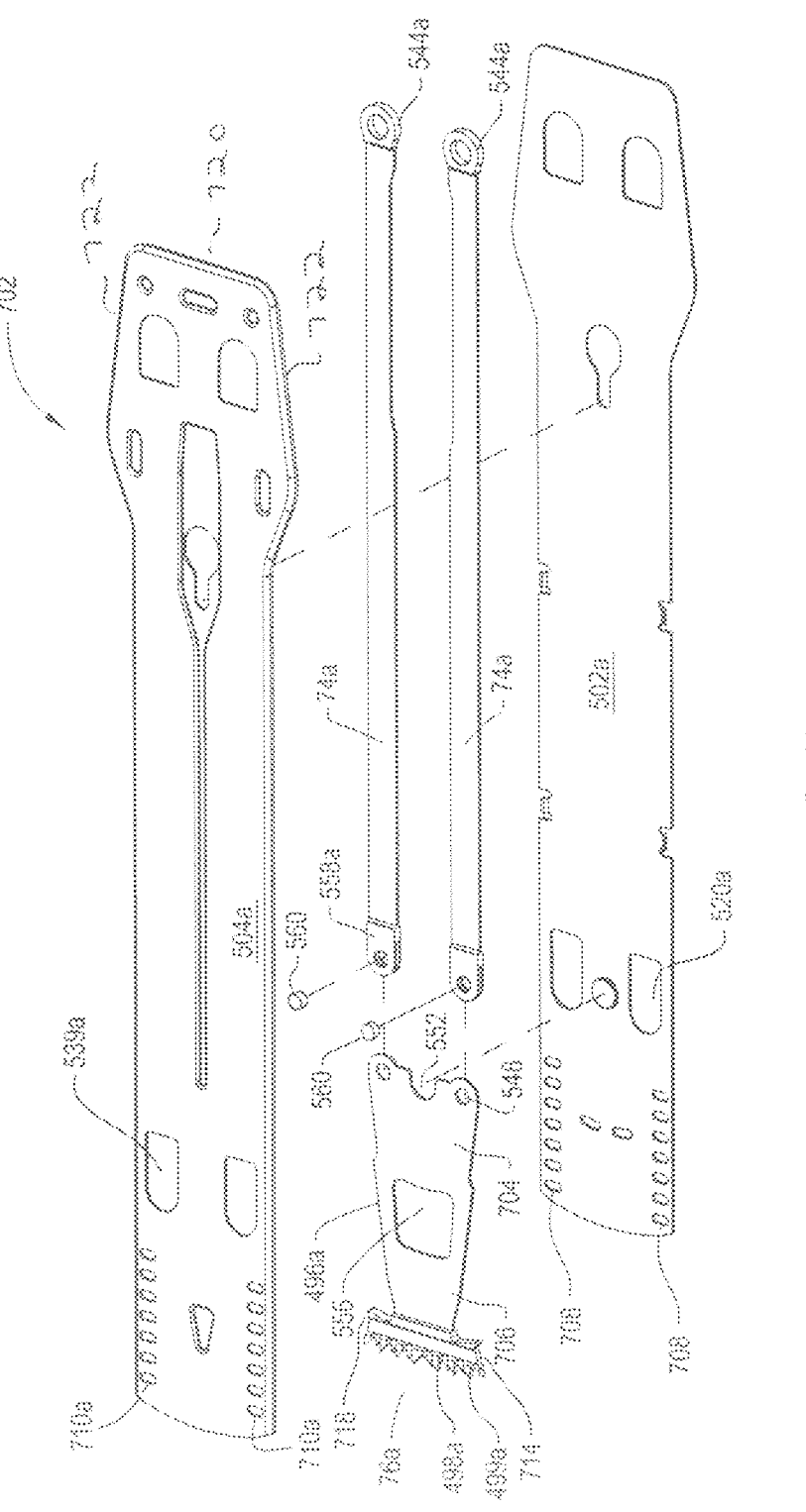
FIG. 65 is an exploded view of an alternative blade assembly of this invention.

FIG. 65 illustrates a blade assembly 702 designed for use with saw head 68*a*. Blade assembly 702 has a blade bar 494*a* from which a moveable blade head 76*a* extends. The blade head 76*a* is generally the same shape as the initially described blade head 76. However blade head 76*a* has base 496*a* with contiguous proximal and distal sections 704 and 706, respectively. The proximal section 704 is the portion of the blade base 496*a* in which openings 548 and notch 552 are formed. Forward of the portion of the proximal section 704 through which openings 548 are formed, the section tapers inwardly. The base distal section 706 extends out forward and laterally beyond the relatively narrow most forward portion of the proximal section 704. Window 556 is formed in the blade base distal section 706. The teeth defining crown 498 of the blade head 76*a* extends forward from the base distal section 706.

Blade bar 494*a* is formed from lower and upper plates 502*a* and 504*a*, respectively. Plates 502*a* and 504 are generally similarly to the initially described plates 502 and 504. However, at the proximal end of the blade bar 494*a*, the plates do not have indentations similar to the previously described indentations 508 (FIG. 43).

At the distal end of the blade bar 494*a*, plates 502*a* and 504*a* are formed to have oval shaped openings 708 and 710, respectively. Each plate 502*a* and 504*a* has two rows of linearly aligned openings. The openings 708 and 710 are located immediately inward of the longitudinal side edges of the plates 502*a*, 504*a*, forward of openings 520*a* and 539*a*, respectively. In one version of the invention, plates 502*a* and 504*a* are formed so that, when assembled together, openings 708 and 710 are not in registration. This is to facilitate final manufacture of blade assembly 702. Specifically, at this time, the upper plate 504a is positioned on a fixture so its inner surface is facing upwardly, is exposed. More particularly the fixture has fingers that extent through the upper plate openings 710. Once all the other components are assembled in the upper plate 504a, the lower plate 502a is placed over the upper plate 504a. Since openings 708 are not in registration with the upper plate openings 710, the fixture fingers abut the inner surface of the lower plate 502a. Thus during the welding process used to secure the plates 502a and 504a together, the fingers hold the distal end of plate 502a off the underlying plate 504a.

During use actuation of the blade assembly 702, windows 708 and 710 function as ports through which bone chips and other matter entrained in the distal open end of the blade bar 494a is ejected from the blade bar.

Blade assembly 702 includes drive rods 74a. D Each drive rod 74a is shaped so that the opposed fingers 558a are integrally formed with the drive rod. Specifically, the drive rod is surface ground to form the narrow thickness elongated body and a relatively wider distal end. A cutting process such as a wire electrical discharge machining process is used to form the finger-separating kerf in which the blade head base 496a is slip fitted. During the surface grinding process, each drive rod 74a is further formed so that the proximal end foot 544 has a greater thickness than the distally adjacent elongated body.

Blade assembly 702 is fitted to saw head 68a in a manner similar to that in which blade assembly 52 is fitted to saw head 68. The proximal end of the blade bar seats between the steps 580 integral with brackets 578. It should be appreciated that blade assembly 702 is relatively thin. This facilitates the insertion of the blade assembly in the narrow slots of a cutting guide (jigs) used to position the blade to ensure the blade makes an appropriately shaped cut. In many versions of the invention, the bar of the blade assembly has an overall thickness of less than 0.080 inches. In some preferred versions of the invention this thickness is 0.065 inches or less. In still other preferred versions of the invention, this thickness is 0.055 inches or less. It is further understood that the thickness of the teeth that extend forward from the blade head should be marginally greater than the width of the blade bar. A minimal difference in these two dimensions is 0.001 inches. The relative dimensions of these components substantially eliminates the likelihood the blade bar will become lodged in the kerf formed in the tissue.

Also, as soon as the blade assembly 702 is pulled beyond tabs 582, the force of the plunger 664 and spring 696 pushes proximal end of the blade bar 494a off the saw head top surface 138a. This further reduces the effort required to remove the blade assembly 702.

From FIG. 65 it can further be seen that blade head crown 498a is formed with laterally side edges 714 that are tapered. More specifically the side edges 714 are tapered so that going forward, distally, along the crow, the edges taper outwardly. The opposed ends of the base of the crown 498a are each provided with a laterally extending finger 718. These structural features are provided so that the longitudinal side edges of the crown 498a proximal to the teeth function as plows. These plows push debris laterally away from the crown 498a. This debris displacement reduces the volume of the debris that then becomes entrained in the blade bar.

FIG. 66 illustrates an alternative oscillating yoke 730 that can be employed with saw head 68a. Yoke 730 is formed to have a U-shaped main body 732. More particularly, the yoke main body 732 is further formed so as to have an inner, U-shaped wall with two parallel spaced apart surfaces 734.

Below the base of the center of the base of the main body 732, yoke 730 is further formed to have a circular boss 736. A threaded bore 738 (shown in phantom) extends upwardly through boss 736 partially into the main body. A smooth walled counterbore 740 extends coaxially upward from bore 738 through the rest of the yoke main body 732.

Oscillating yoke 730 is further formed to have two longitudinally diametrically opposed generally U-shaped notches 744. Notches 744 are located in the top of the yoke main body 732 such that each notch opens into counterbore 740.

Figures 63, 64, 67, 68:
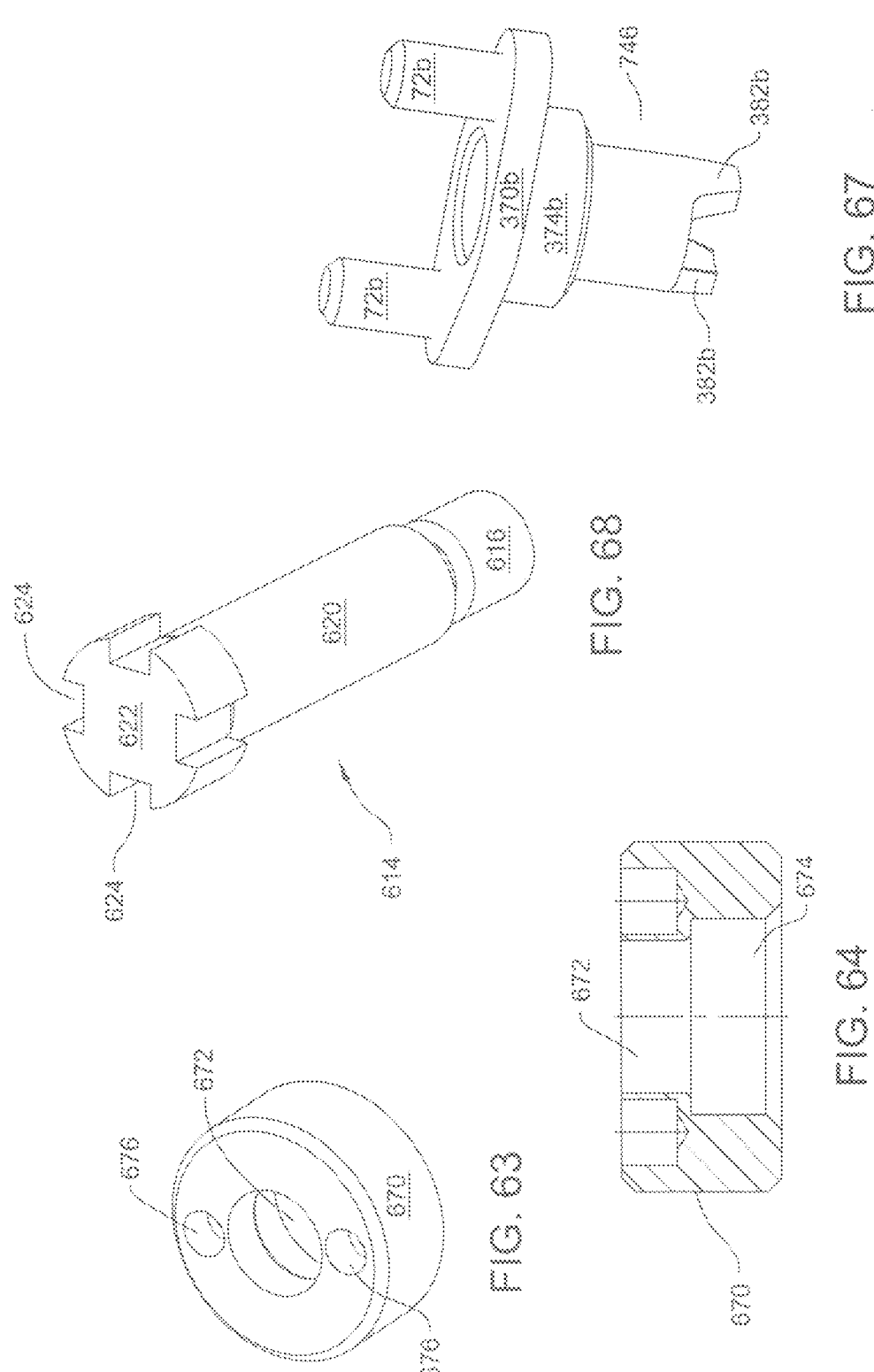
FIG. 63 is a perspective view of the plunger retainer.
FIG. 64 is a cross sectional view of the plunger retainer.
FIG. 67 is a perspective view of another oscillating head.
FIG. 68 is a perspective view of the oscillating assembly retaining screw for use with oscillating yoke of FIG. 66 and the oscillating head of FIG. 67.

An oscillating head 746, shown in detain in FIG. 67, is attached to and extends above oscillating yoke 730. Oscillating head 746 is generally similar in design to the previously described oscillating head 70. Thus, oscillating head 746 includes a top plate 370b from which two drive pins 72b extend. A multi-section boss 374b extends below the top plate 370b. Two opposed feet 382b project below the bottom face of boss 374b. A set of bores (not identified) extend through the components forming the oscillating head 746.

Oscillating yoke boss 736 is rotatably mounted in inner housing bore 332a. Oscillating head boss 374a is rotatably mounted in inner housing bore 330a. When the blade drive assembly is so assembled, feet 382a integral with head 746 seat in yoke notches 744. A retaining screw 750 holds the oscillating head 746 to the oscillating yoke 730. As seen in FIG. 68, retaining screw 750 has a cylindrical, bottom located stem 752. The outer surface of stem 752 is formed with threading (not illustrated) designed to engage the threading of oscillating yoke bore 738. Above stem 752, retaining screw 750 has a smooth walled main body 754 and a head 756. Head 756 has a diameter larger than that of the main body 754. Notches 758 extend inwardly from the outer perimeter of the head to receive a fastening/removal tool (not illustrated).

When the components forming the drive assembly are put together, the screw main body 754 extends through counterbore 740 of the oscillating yoke 730. Screw stem 752 is screw fitted in the top of yoke bore 738. The head 756 of the retaining screw 750 thus bears against the annular internal step into which oscillating head bore 384a opens. Screw 750 is fitted into the open bottom end of oscillating yoke bore 738.

When yoke 730 and oscillating head 746 are fitted to saw head 68a bearing assembly 654 is positioned so as to be disposed within the opposed fingers of the yoke. More particularly, the outer race of the bearing assembly 630 bears against the opposed planar surfaces 734 of the yoke 730. Thus, the rotation of the output shaft 584 is transferred by the bearing assembly 630 into a motion that causes yoke 730 and, by extension, head 746 to oscillate.

Figure 69:
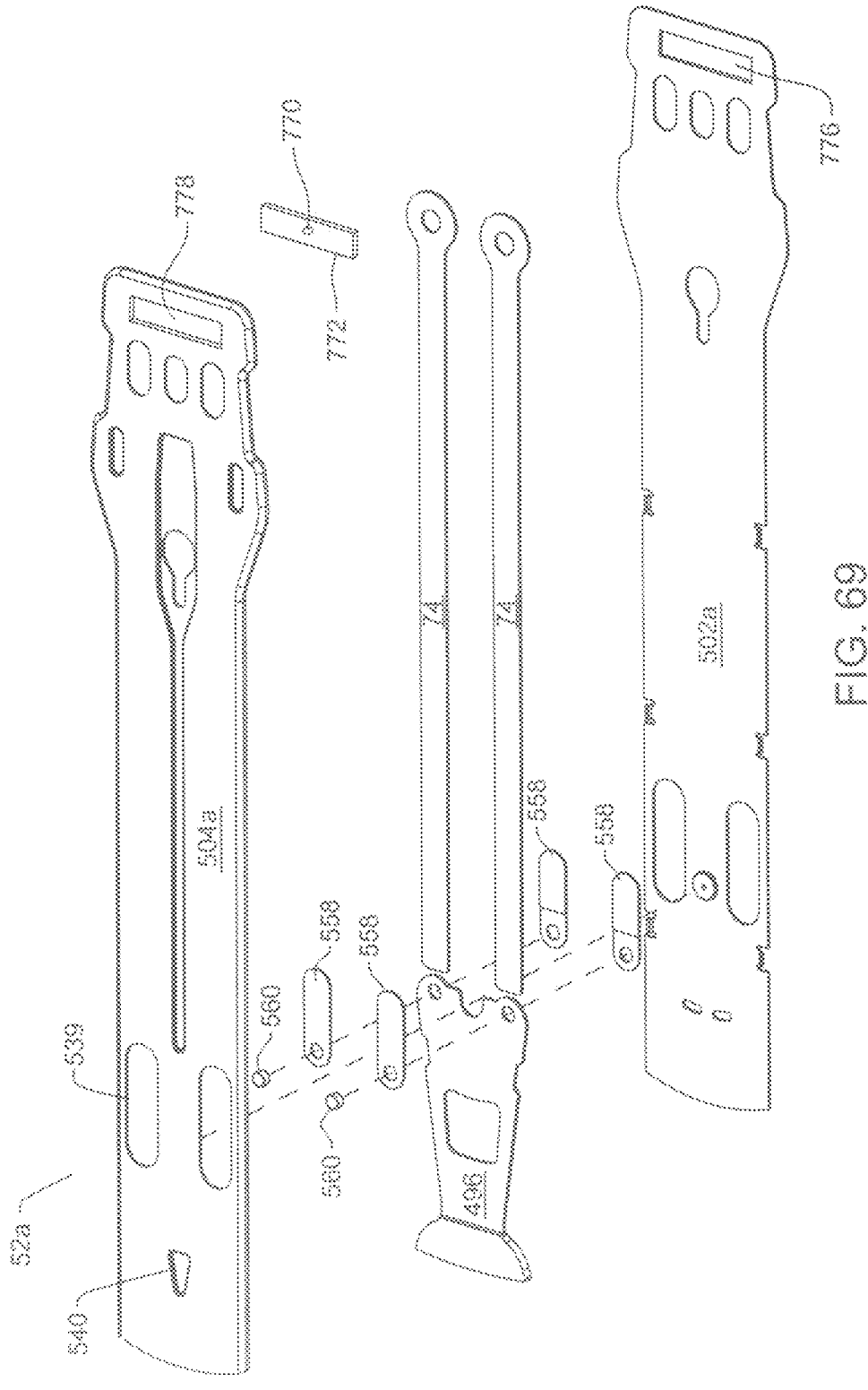
FIG. 69 is an exploded view of an alternative blade assembly of this invention.
Figures 70, 71:
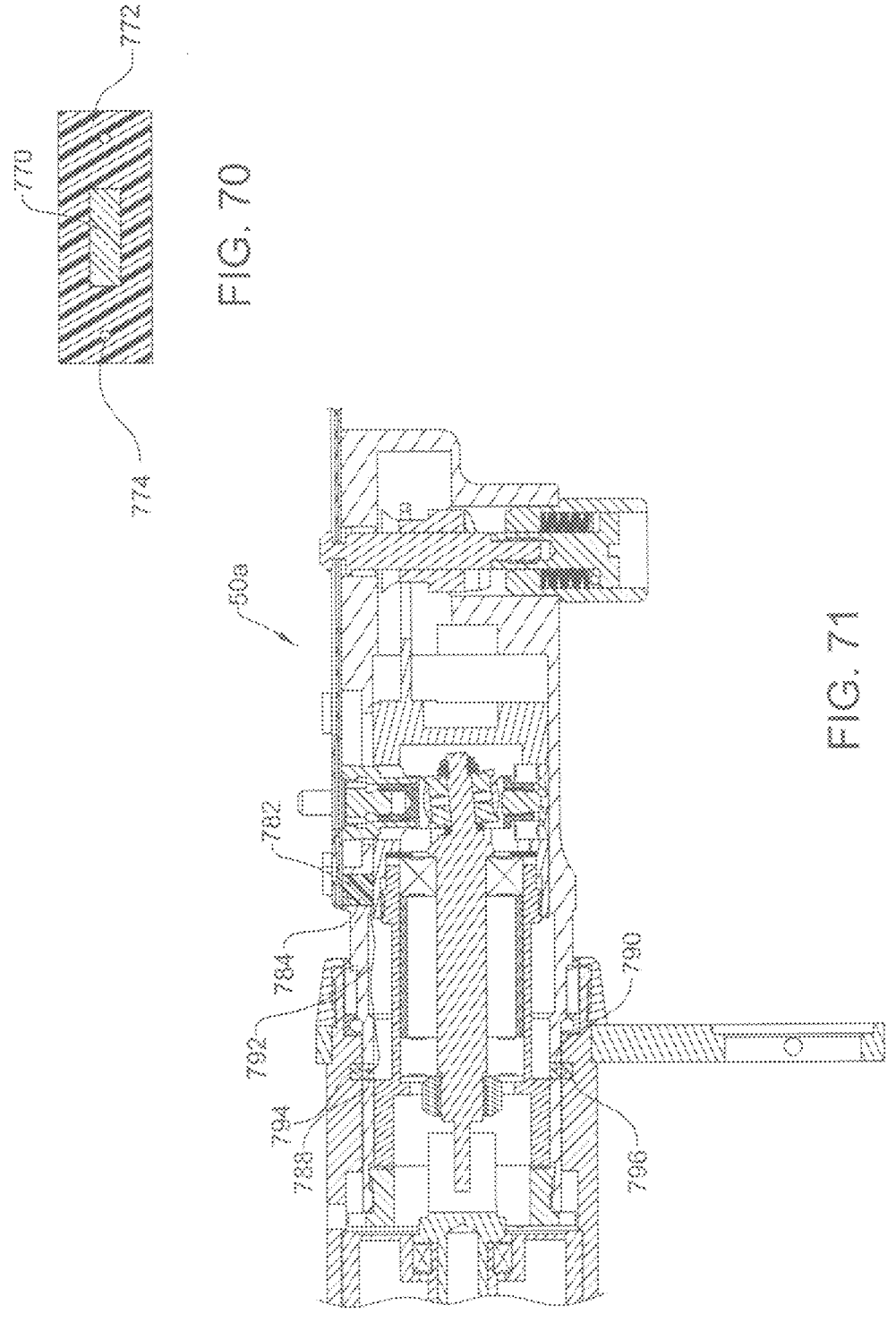
FIG. 70 is a cross sectional view of the module internal to the blade assembly of FIG. 54 that contains an RFID.
FIG. 71 is a cross sectional view of the saw head used with the alternative blade assembly of FIG. 54.
Figure 72:
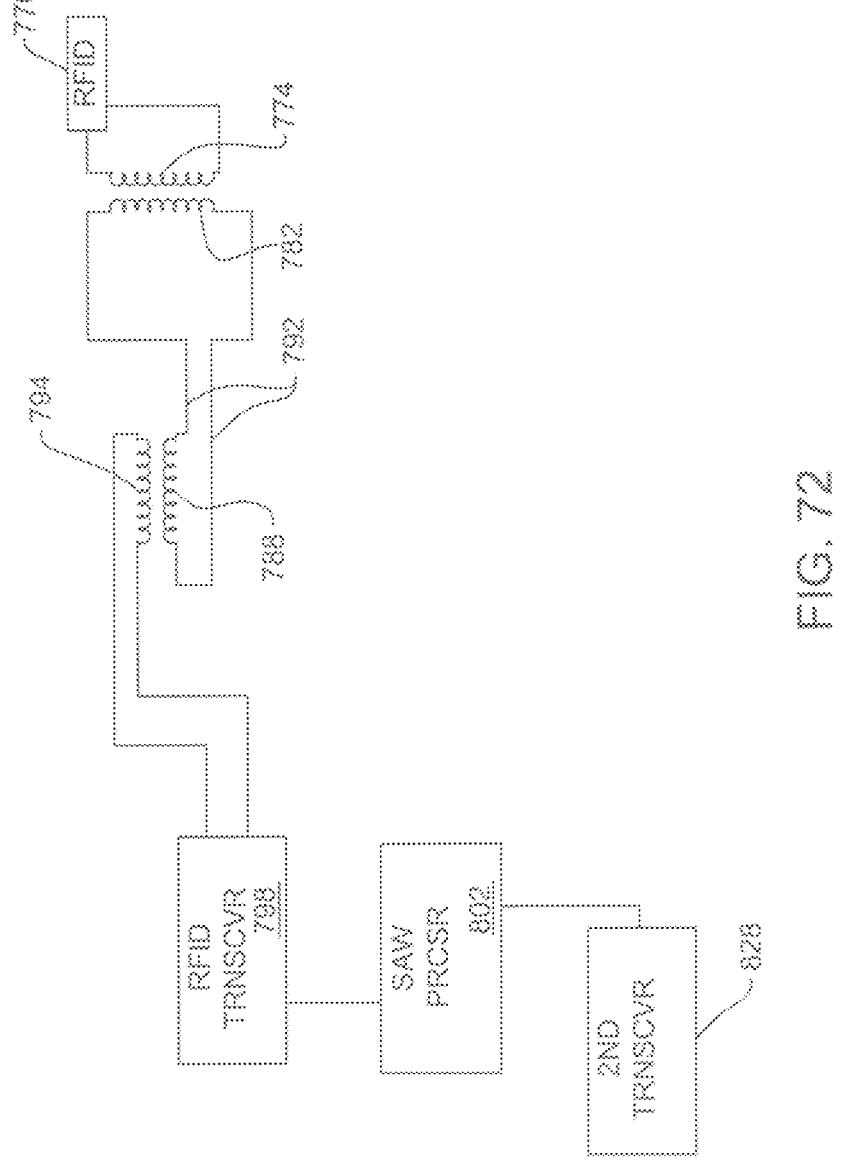
FIG. 72 is a combined schematic and block diagram of the circuit that reads the data stored in the RFID and that regulates the actuation of the saw based on the data.

FIG. 69 is an exploded view of an alternative blade assembly 52a constructed in accordance with this invention. Blade assembly 52a has the same basic structural components as the first described blade assembly 52. Blade assembly 52a is also provided with an RFID tag 770 best seen in FIG. 70. The RFID tag 770 is encased within a plastic block 772. Also disposed within block 772 is a coil 774 represented by the cross section of a single wire. Coil 774 is connected to the RFID and functions as the component through which signals are exchanged with the RFID.

Block 772 is mounted to the blade bar of blade assembly 52a. More particularly, blade assembly 52a includes lower and upper plates 502a and 504a which are generally similar in structure to the first described blade bar-forming plates 502 and 504. Lower plate 502a is further formed to have a distal end through window 776. Upper plate 504 is formed to have a distal end through window 778. Plates 502a and 504a are formed so that when they are assembled together to form the blade bar, windows 776 and 778 are in registration. When the components forming blade assembly 52a are assembled together, block 772 is mounted in plate windows 776 and 778.

In some versions of the invention, block 772 is formed so as to have a flange or lip that extends outwardly from the lateral side walls of the block. This flange has a depth less than that of the block 772. The flange seats in the interstitial space between the opposed, inwardly directed faces of the plates 520a and 504 that define the perimeters of windows 776 and 778, respectively. The flange thus holds block 772 to the blade bar.

FIG. 56 illustrates the saw 50a with which blade assembly 52a is used. Saw 50a contains the same basic components of the first described saw 50. Saw head 68a of saw 50a is further provided with a coil 782 positioned to inductively exchange signals with blade assembly coil 774. More particularly, coil 782 is mounted to the saw head 68a so as to be in a plane parallel and slightly below the head top surface 138a. Coil 782 is located below the top surface section 144a. The coil 782 is disposed in a block 784 an outer face of which forms a portion of top surface section 144a. In some versions of the invention, block 784 is formed from plastic that can withstand the rigors of autoclave sterilization. In other versions of the invention, block 784 is metal.

Coil 782 is connected by conductors 792 to a coil 788. Coil 788 is disposed around the saw head proximal end section 124a. More particularly, coil 788 is encased in a ring 790 fitted disposed around the saw head proximal end section 124a. The ring 790 is seated in a groove formed in the saw head proximal end section 124 (groove not identified). The outer surface of ring 790 is flush with the adjacent outer surface of the saw head proximal end section 124a.

Conductors 792, for the purposes of illustration, are shown as spaced inwardly from the saw head intermediate sections 128a and 132a. In some versions of the invention, conductors 792 are disposed against the inner wall of the saw head 68a. In other versions of the invention, conductors 792 are seated in a groove or a bore that extends longitudinally through the saw head 68a.

Integral with the motor housing 80a is a coil 794 that surrounds coil 788. Coil 794 is contained in a ring 796. The ring 796 is seated in a groove formed in the inner wall of housing 80a that defines the housing third bore (groove not identified).

As seen in FIG. 57, coil 794 is connected to an RFID transceiver 798 internal to the saw 50a. As described in the Applicant's Assignees' U.S. Patent Application No. 60/694,592, POWERED SURGICAL TOOL WITH SEALED CONTROL MODULE, filed 28 Jun. 2005 the contents of which are published in US Pat. Pub. No. 2007/0085496 A1, now U.S. Pat. No. 7,638,958, the contents of which is incorporated herein by reference, it is known to provide a powered surgical tool with a processor 802 capable of regulating the operation of the tool. A data transceiver internal to the tool reads data used to regulate tool operation. RFID transceiver 798 integral with saw of this invention functions as such a data transceiver.

It should be appreciated that when RFID transceiver outputs signals to the RFID tag 770, the signals are first inductively transferred from coil 794 to coil 788. The signals are then inductively transferred from coil 782 to blade assembly coil 774 from where they are forwarded to the RFID tag 770. Signals generated by the RFID tag 770 for the saw RFID transceiver 798 are forwarded to the transceiver over the reverse path.

Static coil 794 surrounds saw head coil 788. Therefore, there is always inductive signal exchange between coils 788 and 794 independent of the index position of the saw head 68a.

Internal to the blade assembly RFID tag 770 is a memory represented by block 806 of FIG. 58. The RFID memory contains data that identifies the blade assembly 52a. For example, in a blade length field 808 data are stored that indicates this length of the blade assembly 52a. In some versions of this invention, this length is the longitudinal distance along the blade from the center of the drive rod foot hole 546 to the apex of the blade head crown 498 when the blade head is centered on the blade bar. One or mode blade geometry data fields 810 contain data that describes the profile of the blade head crown. These data describe: the radius of curvature of the crown; the arc subtended by the distal end of the crown; and the thickness of the crown. A teeth geometry data field 811 contains data that describes the profile of the teeth formed in the blade crown.

The RFID tag memory also contains data that are used to regulate the actuation of the blade assembly 52a. These data are, for example, stored in a default and maximum operating speed data fields 812 and 814. The data in the default operating speed field 812 indicates a standard initial cycle rate at which the blade head should be oscillated back and forth. The data in the maximum operating speed data field 814 contains data indicating the maximum speed at which the blade head should be oscillated.

The RFID tag memory also contains fields in which data are written after the blade assembly 52a is attached to the saw. A use history data field 816 is used to store data indicating if the blade assembly has been used and/or the number of times the blade assembly has been used. In some versions of the invention, the use history data field 816 may be a single bit flag field. There is also a time stamp field. The time stamp field 818 is used to store data indicating the first or last time the blade assembly 52a was attached to a saw.

Figure 74:
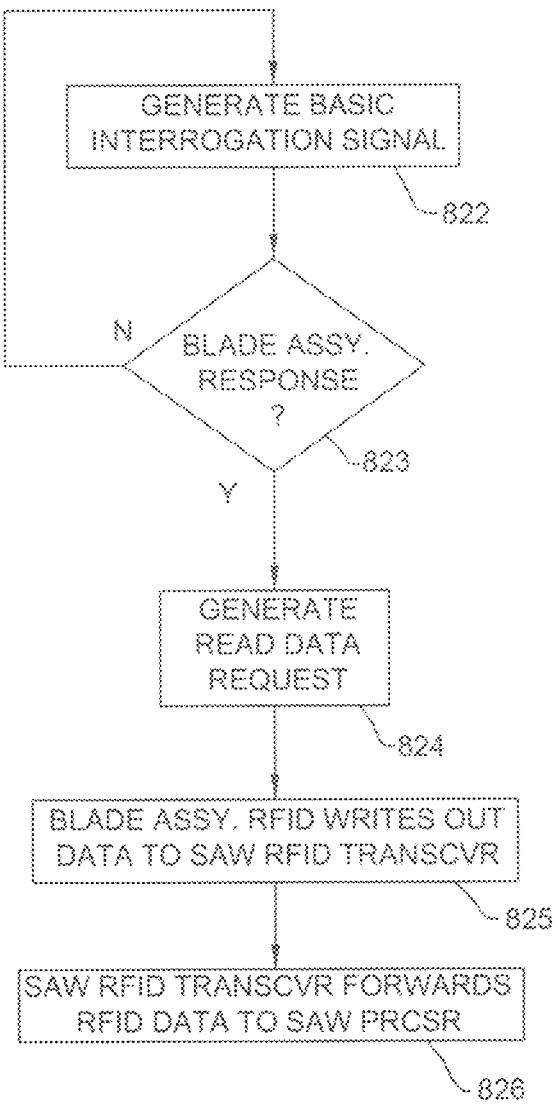
FIG. 74 is a flow chart of the process steps executed in order to read the data in blade assembly RFID.

When saw 50a and blade assembly 52a of this version of the invention are used, the blade assembly is attached to the saw head 68a is in the first described embodiment. The data in the RFID tag 770 are read more. More particularly, the RFID transceiver 798 integral with the saw 50a periodically generates a basic interrogation signal, step 822 of FIG. 74. This signal is continually periodically output by transceiver 798. If a blade assembly 52a is not attached to the saw 50a, there is no response to this signal.

When a blade assembly 52a with an RFID tag 770 is attached to the saw head 68b, in response to the basic interrogation signal, the RFID tag outputs a short acknowledgment signal, step 823. Upon receipt of this acknowledgement signal, the RFID transceiver 798 outputs a read data request to the RFID tag 770, step 824. In response to this request, in step 713, the RFID tag 770 outputs all the stored data to the RFID transceiver 798, step 825. The RFID transceiver, in turn, forwards the data to the saw processor 802, step 826. Saw processor 802 then regulates the actuation of the saw based on these data.

Saw processor 802 may also cause the data describing the characteristics of the blade assembly 52a to be forwarded to a remote unit through a second transceiver 828. These data are then received by other equipment in the operating room in which the surgical procedure in which saw 50a and blade assembly 52a are being used.

Figure 75:
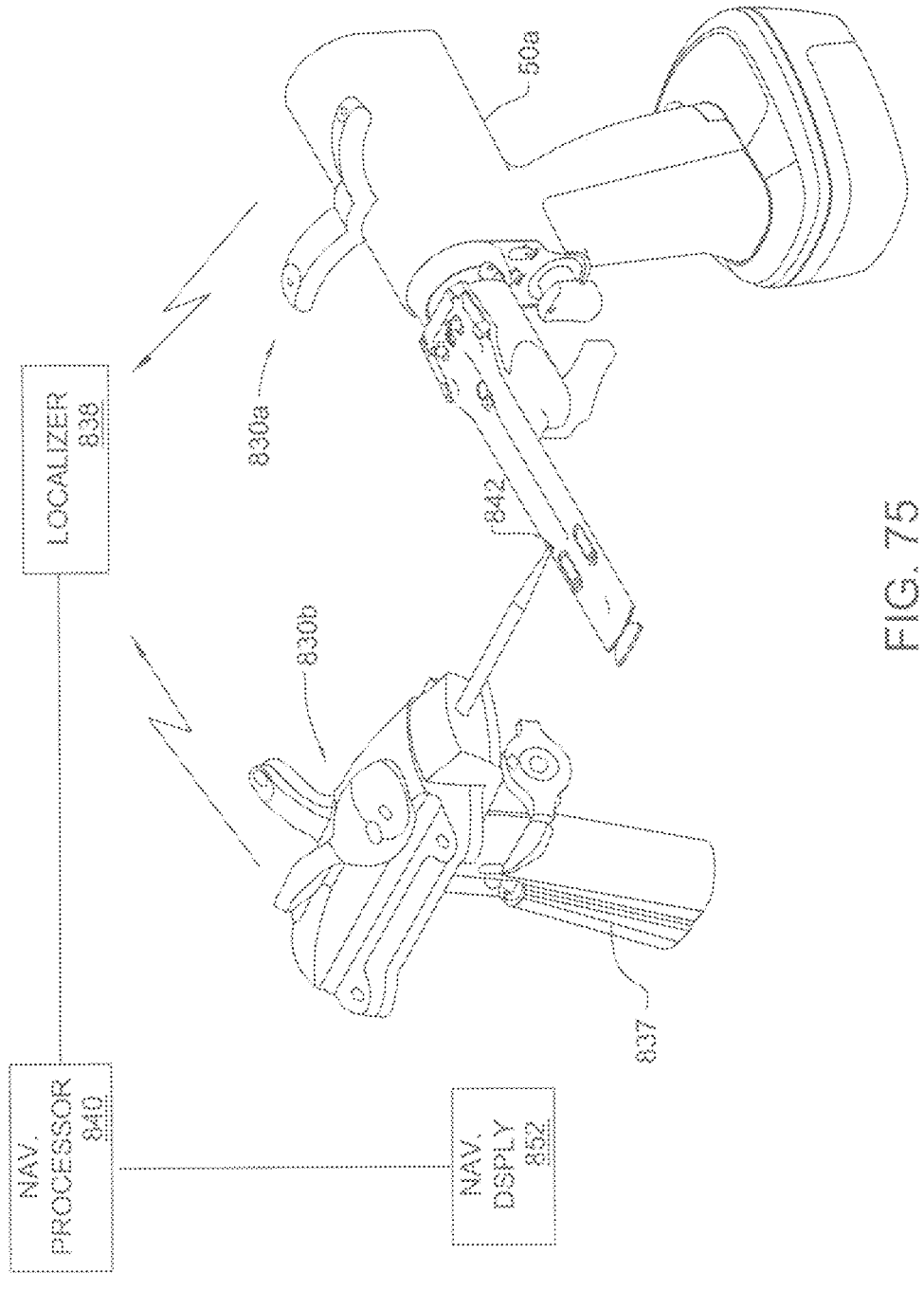
FIG. 75 is a diagrammatic illustration of how the surgical saw of this invention is used with a surgical navigation system.

One such piece of equipment is a surgical navigation system. This system, as generally illustrated in FIG. 75 includes a number of trackers 830*a* and 830*b*. Each tracker 830*a* and 830*b* is attached to a separate one of the surgical tools; tracker 830*a* is attached to saw 50*a*. A localizer 838 receives signals emitted by the trackers 830 and generates basic signals based on the position and orientation of each tracker 830*a* and 830*b*. The localizer generated signals are forwarded to a navigation processor 840. The navigation processor 840, based on the localizer-generated signals, determines the position and orientation of the surgical tools to which the trackers 830*a* and 830*b* are attached. Based on these data, an image is generated indicating the position and orientation of the surgical tools relative to the surgical site.

Figure 76:
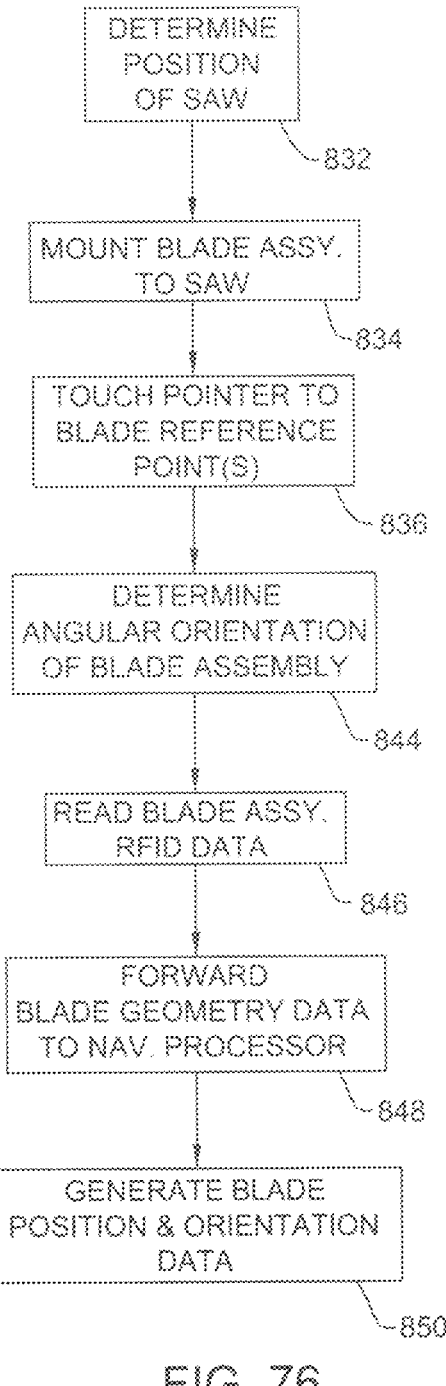
FIG. 76 is a flow chart of the process steps executed in order to employ a surgical navigation system to determine the position of the blade head of a saw blade according to this invention.

As indicated in step 832 of FIG. 76, in a method of surgical navigation using saw 50*a* of this invention, based on signals emitted by tracker 830*a*, the position and orientation of saw 50*a* is determined. In After the saw head 68*a* is indexed, (step not shown,) blade assembly 52*a* is mounted to saw 50*a*, step 834.

Then, in a step 836 a surgical tool known is a pointer 837 is touched to a reference point or points formed on the blade bar. These points may be one or more divots 842 (one shown) or a groove formed on the blade bar. A separate tracker, tracker 830*b*, is attached to pointer 837. Therefore, as a consequence of the execution of step 836, navigation processor 840 generates data indicating the position and orientation of the blade bar head reference point(s). The navigation processor 840 therefore has data indicating both the position and orientation of the saw 50*a* and of the reference point(s). Based on these data, in a step 844, the navigation processor 840 determines the angular orientation, the index position, of the blade assembly 52*a*.

In a step 846, the data in the blade assembly RFID tag 680 are read. In a step 848 at least the data descriptive of blade length and crown geometry are forwarded to the navigation processor 840. Owing to the proximally-directed biasing force imposed by spring 422 on the blade assembly 52*a*, the proximal ends of the blade bar 496 regularly seat in a known position relative to a fixed reference point on the blade head top surface. Thus, the navigation processor 840 contains the following data: the position and orientation of the saw 50*a*; the angular orientation of the blade bar around a known axis of the saw; and the length of the blade assembly 52*a*. Based on these data, in step 850, the navigation processor generates data indicating the position and orientation of the distal end of the blade assembly 52*a*, crown 498. The navigation processor 840 is then able to generate an image on a display 852 indicating the position of the blade assembly crown 498 relative to the surgical site on the patient.

In an alternative version of the method of the invention, after the saw head 68*a* is indexed, pointer 837 is touched to a divot 746 or other reference marker formed on the saw head 68*a*. Based on the position of this divot, navigation processor 840 determines the orientation, indexed position, of the saw head 68*a*. The blade bar is static relative to the saw head. The position of the saw head 68*a* is then used to determine the index orientation of the blade assembly relative to the saw 52*a*.

Figures 77, 78:
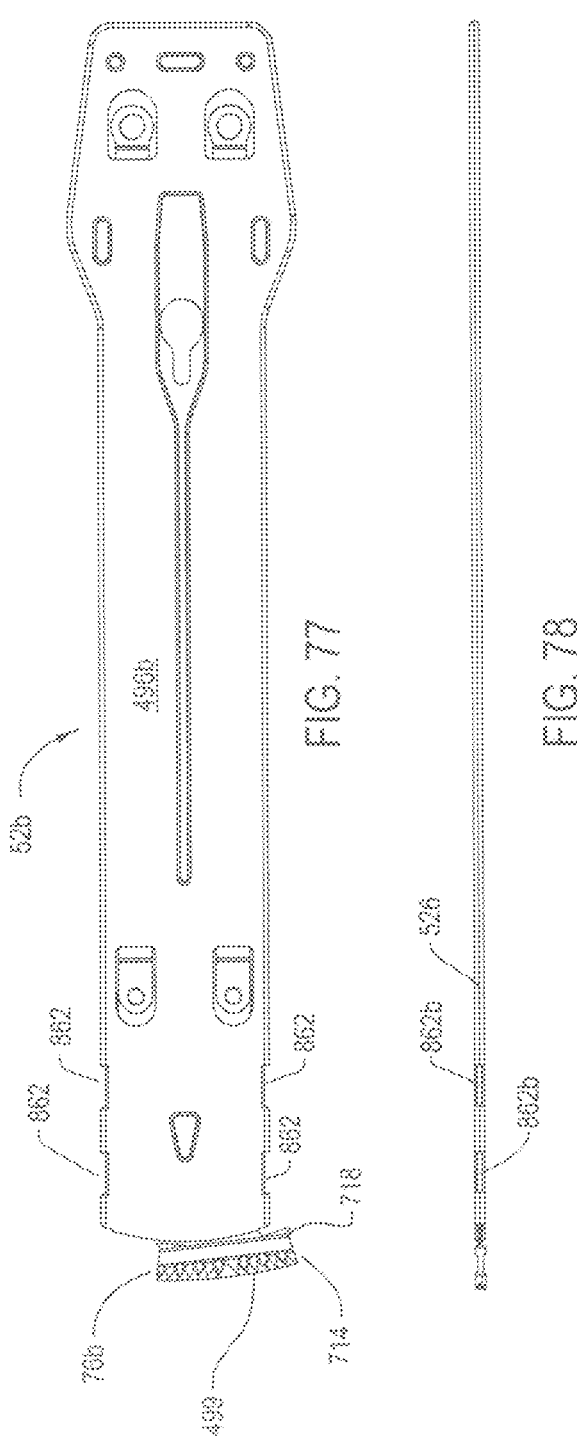
FIG. 77 is a plan view of another alternative blade assembly of this invention.
FIG. 78 is a side view of the blade assembly of FIG. 77.

FIGS. 77 and 78 illustrate an alternative blade assembly 52*b*. Blade assembly 52*b* has the same basic blade bar and blade head of the previously described blade assemblies. However, blade assembly 52*b* has a blade bar 494*b* where the opposed side walls at distal end section in which the blade head base is seated are formed with ports 862. Ports 862 are created by first forming slots (not illustrated) in the upper plate lip 526. As a consequence of the attachment of the lower and upper plates 502 and 504, respectively, together, the slots become blade ports 862.

While not illustrated, it should be understood that blade assembly 52*b* includes an appropriate blade head. The blade head is formed with a base from which fingers 868 extend outwardly from the opposed longitudinal side edges. The blade head s formed so that when the blade head pivots back and forth, each set of fingers on one side of the head extend a short distance through the associated blade bar side-wall located ports 862.

When blade assembly 52*b* of this version of the invention cuts bone or other tissue, at least some of the tissue enters the distal end opening of the bar 494*b* through which blade head 76*b* extends. As the blade head pivots back and forth, the fingers force the entrained tissue out through the bar assembly side wall ports 862.

Moreover, the saw of this invention may be used to oscillate saw blades that have different structures from what has been disclosed. For example, in some versions of the invention, the oscillating shaft may oscillate a single pin or a cap designed to receive the proximal end of a conventional saw blade formed out of a single piece of metal. In versions of the invention wherein there is a single pin, it is anticipated that the pin will have an opening with a noncircular profile. The saw blade would have an opening with a similar profile such that when the blade is seated over the pin, the two components rotate together. If the oscillating head contains a cap, internal to the cap is an assembly for holding the blade in the cap.

There is no reason that, in all versions of the invention, the oscillating drive assembly be mounted to saw head so that the oscillating head is biased towards the proximal end of the saw head. In alternative versions of the invention, the oscillating drive assembly may be configured so that the biasing member normally urges the exposed oscillating head components to the forward, distal end of the saw head.

Alternative means to index the saw head relative to the rest of the saw may be employed. For example, in some versions of the invention, the link mechanism that controls indexing may be moveably attached to the saw housing not the rotating saw head. In some versions of the invention, a single biasing member may both press the saw head against the static saw housing and inhibit rotation of the saw head.

The blade coupling assembly may likewise vary. Thus, there is no requirement that in all versions of the invention the blade coupling assembly simultaneously function as a device that clamps the inner housing assembly to the saw head to prevent relative motion of these components. There may be reasons in some versions of the invention wherein removable components are used to releasably secure the blade assembly to the saw head.

The blade assembly may similarly vary from what has been described. For example, in some versions of the invention, a single drive rod may be all that is needed to pivot the blade head. Similarly, alternative means may be employed to pivotally connect the drive rod(s) to the blade head. Alternative means may also be employed to pivotally mount the blade head to the blade assembly bar. These include the alternative assemblies employed in the incorporated-by-reference U.S. patent application Ser. No. 10/887, 642.

Further the openings in the distal section of the blade bar in which the blade head is disposed and through which entrained tissue is discharged may vary from what is illustrated.

Therefore, it is an object of the appended claims to cover all such variations and modifications that come within the true spirit and scope of the invention.

What is claimed is:

1. A method of navigating a surgical saw with a navigation system having a navigation processor, said method comprising:

attaching a saw blade to a head of the surgical saw;

touching a tracked pointer to one or more reference points on the saw blade;

determining a position and orientation of the surgical saw;

tracking the position and orientation of the tracked pointer as the tracked pointer is touched to the one or more reference points on the saw blade;

determining an angular orientation of the saw blade based on the position and orientation of the tracked pointer when touching the one or more reference points on the saw blade; and determining the position and orientation of a distal end of the saw blade relative to surgical saw using the navigation processor based on the position and orientation of the surgical saw, the angular orientation of the saw blade, and a characteristic of the saw blade.

2. The method of claim 1, wherein the surgical saw includes a saw processor, said method further comprising the step of reading a tag on the saw blade, the tag comprising data related to the characteristic of the saw blade; and modifying operation of the surgical saw based on the characteristic of the saw blade using the saw processor.

3. The method of claim 1, further comprising the step of reading a tag on the saw blade, the tag comprising data related to the characteristic of the saw blade, the characteristic including a length of the saw blade.

4. The method of claim 1, further comprising the step of displaying the position of the saw blade relative to the surgical site.

5. The method of claim 1, wherein the one or more reference points comprise one or more divots formed on the saw blade.

6. The method of claim 1, wherein the one or more reference points comprise a groove formed on the saw blade.

7. The method of claim 1, wherein the step of determining a position and orientation of the surgical saw comprises tracking the surgical saw with a first tracking device to determine the position and orientation of the surgical saw.

8. The method of claim 1, wherein the head of the surgical saw includes a divot, wherein the step of determining a position and orientation of the surgical saw comprises touching the tracked pointer to the divot of the head of the surgical saw.

9. The method of claim 1, said method further comprising the step of indexing the head of a surgical saw about a longitudinal axis of the surgical saw before the step of determining a position and orientation of the surgical saw.

10. The method of claim 1, further comprising the step of communicating data from the surgical saw to the navigation system.

11. A method of navigating a surgical saw with a navigation system having a navigation processor, said method comprising:

indexing a head of a surgical saw about a longitudinal axis of the surgical saw;

attaching a saw blade assembly to the indexed head of the surgical saw;

touching a tracked pointer to one or more reference points on the saw blade assembly;

determining a position and orientation of the surgical saw;

tracking the position and orientation of the tracked pointer as the tracked pointer is touched to the one or more reference points on the saw blade assembly;

determining an angular orientation of the saw blade assembly based on the position and orientation of the tracked pointer when touching the one or more reference points on the saw blade assembly; and determining the position and orientation of a distal end of the saw blade relative to surgical saw using the navigation processor based on the position and orientation of the saw, the angular orientation of the saw blade assembly, and a length of the saw blade assembly.

12. The method of claim 11, wherein the surgical saw includes a saw processor, said method further comprising the steps of:

reading a tag on the saw blade, the tag comprising data related to the length of the saw blade assembly; and modifying operation of the surgical saw based on the length of the saw blade assembly using the saw processor.

13. The method of claim 11, further comprising the step of communicating data from the surgical saw to the navigation system.

14. The method of claim 11, further comprising the step of displaying the position of the saw blade assembly relative to the surgical site.

15. The method of claim 11, wherein the one or more reference points comprise one or more divots formed on the saw blade assembly.

16. The method of claim 11, wherein the one or more reference points comprise a groove formed on the saw blade assembly.

17. The method of claim 11, wherein the step of determining a position and orientation of the surgical saw comprises tracking the surgical saw with a first tracking device to determine the position and orientation of the surgical saw.

18. The method of claim 11, further comprising the step of communicating data from the surgical saw to the navigation system.

* * * * *